US007364745B2

(12) United States Patent
Bandara et al.

(10) Patent No.: US 7,364,745 B2
(45) **Date of Patent: *Apr. 29, 2008**

(54) DEVELOPMENT OF A LIVE, ATTENUATED, RECOMBINANT VACCINE FOR BRUCELLOSIS

(75) Inventors: Aloka B. Bandara, Blacksburg, VA (US); Stephen M. Boyle, Blacksburg, VA (US); Nammalwar Sriranganathan, Blacksburg, VA (US); Gerhardt G. Schurig, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 111 days.

This patent is subject to a terminal disclaimer.

(21) Appl. No.: 11/246,957

(22) Filed: Oct. 11, 2005

(65) Prior Publication Data

US 2006/0093621 A1 May 4, 2006

Related U.S. Application Data

(63) Continuation-in-part of application No. 11/050,429, filed on Feb. 4, 2005.

(60) Provisional application No. 60/541,954, filed on Feb. 6, 2004.

(51) Int. Cl.
*A61K 39/10* (2006.01)
*C12N 15/74* (2006.01)

(52) U.S. Cl. .................... 424/252.1; 435/471; 435/477

(58) Field of Classification Search .................... None
See application file for complete search history.

(56) References Cited

U.S. PATENT DOCUMENTS

| | | | | |
|---|---|---|---|---|
| 5,718,903 | A * | 2/1998 | Adams et al. | 424/235.1 |
| 5,851,519 | A * | 12/1998 | Dougan et al. | 424/93.2 |
| 5,939,075 | A * | 8/1999 | Houng et al. | 424/252.1 |
| 6,149,920 | A * | 11/2000 | Boyle et al. | 424/252.1 |
| 6,296,855 | B1 * | 10/2001 | Hemmen et al. | 424/252.1 |
| 6,444,445 | B2 * | 9/2002 | Nikolich et al. | 435/69.3 |
| 6,582,699 | B2 * | 6/2003 | Cherwonogrodzky | 424/184.1 |

(Continued)

FOREIGN PATENT DOCUMENTS

ES 2140336 * 2/2000

(Continued)

OTHER PUBLICATIONS

DelVecchio et al., 2002, "The genome sequence of the facultative intracellular pathogen *Brucella melitensis*", Proceedings of the National Academy of Sciences, USA, vol. 99, No. 1, pp. 443-448.*

(Continued)

*Primary Examiner*—Nashaat T. Nashed
*Assistant Examiner*—William W. Moore
(74) *Attorney, Agent, or Firm*—Whitham Curtis Christofferson & Cook, PC

(57) ABSTRACT

A recombinant, attenuated strain of *Brucella suis* or *Brucella melitensis* with a deficiency in carboxyl-terminal protease activity or tail-specific protease activity can be used as a vaccine for the prevention or treatment of Brucellosis. Prior exposure to the *Brucella* species is identified by detecting a genetic sequence for carboxyl-terminal (i.e. tail-specific) protease activity in a biological sample.

7 Claims, 16 Drawing Sheets

U.S. PATENT DOCUMENTS

| | | | | |
|---|---|---|---|---|
| 6,811,787 | B1 * | 11/2004 | Boyle et al. | 424/252.1 |
| 2003/0044431 | A1 * | 3/2003 | Schurig et al. | 424/252.1 |
| 2005/0142151 | A1 * | 6/2005 | Nikolich et al. | 424/252.1 |
| 2005/0249755 | A1 * | 11/2005 | Nikolich et al. | 424/252.1 |
| 2006/0153868 | A1 * | 7/2006 | Ugalde et al. | 424/200.1 |

FOREIGN PATENT DOCUMENTS

| | | | |
|---|---|---|---|
| WO | WO 88/07374 | * | 10/1988 |
| WO | WO 98/08951 | * | 3/1998 |

OTHER PUBLICATIONS

Paulsen et al., 2002. "The *Brucella suis* genome reveals fundamental similarities between animal and plant pathogens and symbionts", Proceedings of the National Academy of Sciences, USA, vol. 99, No. 20, pp. 13148-13153.*

* cited by examiner tcagtt cagcacgccc tttttcgggt ccggcgggaa agcggcattg ggcacttcgc cccgcagaag
cttcagtgcc tcattgagct ggagatcatc cttcggatca ggcggaacat aagccgacga
accggagccg ctcgcatctt cggcattgcc cttgatatgg cccttgagtt cggattcgcc
gcgaacaacg tcctcgcctt taagttccgg cggcagcggc tgatccacct tgatgtccgg
cgtaatgccc ttgccctgga tcgacttgcc agacggcgtg taataaagcg ccgtcgtcag
acgcagcgaa ccgttttcgc caagcgggat gattgtctgc acagagccct tgccgaagga
ctgcgtaccg agcaccgtgg cgcggcgatg atcctgaagc gcaccggcaa cgatttccga
ggcactggcc gaaccgccat tgatcagaac gatcagcggc ttgccattcg tcaggtcacc
cttacgggca tcgaaacggg tcacatcctg cggatcgcgg ccacgggtgg aaacgatctc
gcccttgtcg aggaaggcat cggaaacggc aaccgcctga tccagaaggc cgccccggatt
gagacgaagg tcgagcacat agcccttgag cttgtcagcg ggaacctttt cctgaatgtc
cttgatcgcc ttcttgaggt cttcagaggt ctgttcggta aacgagatga tacgcagata gccaacatca
ttctcaacgc gcgagcgaac cgccttcacc ttgataatgg cgcgattgat cttgagcgtg atcggcttgt
cggcgcccctt gcgcaggatc gtcagttcga ttggcgcacc aacctcgccg cgcatcttgt
ccacagcgtc ggtcagcgaa aggccgcgca cttcctgtcc gtcgatcttg gtgatcaggt
cgcccgacag cacaccggcc ttcgaggcgg gcgtatcgtc gatcggcgcg atgaccttca
cgagatcatt gtccatggtg acttcgatgc caaggccgcc aaactcaccc ttggtctgca
cacgcatgtc ctgcgcggct tccgggttga gataggacga atggggatca agagaagtca
gcatgccatt gatggcgctc tcgatcagct tcttgtcgtc gggcggcgtc acatattgcg
cgcgtacacg ctcgaaaata tcgccgaaaa gagccagctc cttatagaca tcgctgtctt
ttcctgccgc aaaagcggtg gaagctggtg cgccctggac catcaccat

*Figure 1A*

MVMVQGAPASTAFAAGKDSDVYKELALFGDIFERVRAQYVTPPDDK
KLIESAINGMLTSLDPHSSYLNPEAAQDMRVQTKGEFGGLGIEVTMD
NDLVKVIAPIDDTPASKAGVLSGDLITKIDGQEVRGLSLTDAVDKMR
GEVGAPIELTILRKGADKPITLKINRAIIKVKAVRSRVENDVGYLRIISF
TEQTSEDLKKAIKDIQEKVPADKLKGYVLDLRLNPGGLLDQAVAVSD
AFLDKGEIVSTRGRDPQDVTRFDARKGDLTNGKPLIVLINGGSASASE
IVAGALQDHRRATVLGTQSFGKGSVQTIIPLGENGSLRLTTALYYTPS
GKSIQGKGITPDIKVDQPLPPELKGEDVVRGESELKGHIKGNAEDAS
GSGSSAYVPPDP KDDLQLNEALKLLRGEVPNAAFPPDPKKGVLN

*Figure 1B* atcagaac gatcagcggc ttgccattcg tcaggtcacc cttacgggca tcgaaacggg tcacatcctg cggatcgcgg ccacgggtgg aaacgatctc gcccttgtcg aggaaggcat cggaaacggc aaccgcctga tccagaaggc cgcccggatt gagacgaagg tcgagcacat agcccttgag cttgtcagcg ggaacctttt cctgaatgtc cttgatcgcc ttcttgaggt cttcagaggt ctgttcggta aacgagatga tacgcagata gccaacatca ttctcaacgc gcgagcgaac cgccttcacc ttgataatgg cgcgattgat cttgagcgtg atcggcttgt cggcgccctt gcgcaggatc gtcagttcga ttggcgcacc aacctcgccg cgcatcttgt ccacagcgtc ggtcagcgaa aggccgcgca cttcctgtcc gtcgatcttg gtg

Figure 2 tcagtt cagcacgccc tttttcgggt ccggcgggaa agcggcattg ggcacttcgc cccgcagaag cttcagtgcc tcattgagct ggagatcatc cttcggatca ggcggaacat aagccgacga accggagccg ctcgcatctt cggcattgcc cttgatatgg cccttgagtt cggattcgcc gcgaacaacg tcctcgcctt taagttccgg cggcagcggc tgatccacct tgatgtccgg cgtaatgccc ttgccctgga tcgacttgcc agacggcgtg taataaagcg ccgtcgtcag acgcagcgaa ccgttttcgc caagcgggat gattgtctgc acagagccct tgccgaagga ctgcgtaccg agcaccgtgg cgcggcgatg atcctgaagc gcaccggcaa cgatttccga ggcactggcc gaaccgccat tg=========deletion*========= atcaggt cgcccgacag cacaccggcc ttcgaggcgg gcgtatcgtc gatcggcgcg atgaccttca cgagatcatt gtccatggtg acttcgatgc caaggccgcc aaactcaccc ttggtctgca cacgcatgtc ctgcgcggct tccgggttga gataggacga atggggatca agagaagtca gcatgccatt gatggcgctc tcgatcagct tcttgtcgtc gggcggcgtc acatattgcg cgcgtacacg ctcgaaaata tcgccgaaaa gagccagctc cttatagaca tcgctgtctt ttcctgccgc aaaagcggtg gaagctggtg cgccctggac catcaccat

* A gene encoding resistance to antibiotic Kanamycin was incorporated to this deleted region.

Figure 3 atgatacgtaaactgtcgctgctgttcgccggggcccttctgggggcatccgccatggtgatggtccagggcgcaccagc
ttccaccgcttttgcggcaggaaaagacagcgatgtctataaggagctggctcttttcggcgatattttcgagcgtgtac
gcgcgcaatatgtgacgccgcccgacgacaagaagctgatcgagagcgccatcaatggcatgctgacttctcttgatccc
cattcgtcctatctcaacccggaagccgcgcaggacatgcgtgtgcagaccaagggtgagtttggcggccttggcatcga
agtcaccatggacaacgatctcgtgaaggtcatcgcgccgatcgacgatacgcccgcctcgaaggccggtgtgctgtcgg
gcgacctgatcaccaagatcgacggacaggaagtgcgcggcctttcgctgaccgacgctgtggacaagatgcgcggcgag
gttggtgcgccaatcgaactgacgatcctgcgcaagggcgccgacaagccgatcacgctcaagatcaatcgcgccattat
caaggtgaaggcggttcgctcgcgcgttgagaatgatgttggctatctgcgtatcatctcgtttaccgaacagacctctg
aagacctcaagaaggcgatcaaggacattcaggaaaaggttcccgctgacaagctcaagggctatgtgctcgaccttcgt
ctcaatccgggcggccttctggatcaggcggttgccgtttccgatgccttcctcgacaagggcgagatcgtttccacccg
tggccgcgatccgcaggatgtgacccgtttcgatgtccgtaagggtgacctgacgaatggcaagccgctgatcgttctga
tcaatggcggttcggccagtgcctcggaaatcgttgccggtgcgcttcaggatcatcgccgcgccacggtgctcggtacg
cagtccttcggcaagggctctgtgcagacaatcatcccgcttggcgaaaacggttcgctgcgtctgacgacggcgcttta
ttacacgccgtctggcaagtcgatccagggcaagggcattacgccggacatcaaggtggatcagccgctgccgccggaac
ttaaaggcgaggacgttgttcgcggcgaatccgaactcaagggccatatcaagggcaatgccgaagatgcgagcggctcc
ggttcgtcggcttatgttccgcctgatccgaaggatgatctccagctcaatgaggcactgaagcttctgcggggcgaagt
ggccaatgccgctttcccgccggacccgaaaaagggcgtgctgaactga

*Figure 12A*

MIRKLSLLFAGALLGASAMVMVQGAPASTAFAAGKDSDVYKELALFGDIFERVR
AQYVTPPDDKKLIESAINGMLTSLDPHSSYLNPEAAQDMRVQTKGEFGGLGIEVT
MDNDLVKVIAPIDDTPASKAGVLSGDLITKIDGQEVRGLSLTDAVDKMRGEVGA
PIELTILRKGADKPITLKINRAIIKVKAVRSRVENDVGYLRIISFTEQTSEDLKKAIK
DIQEKVPADKLKGYVLDLRLNPGGLLDQAVAVSDAFLDKGEIVSTRGRDPQDVT
RFDVRKGDLTNGKPLIVLINGGSASASEIVAGALQDHRRATVLGTQSFGKGSVQT
IIPLGENGSLRLTTALYYTPSGKSIQGKGITPDIKVDQPLPPELKGEDVVRGESELK
GHIKGNAEDASGSGSSAYVPPDPKDDLQLNEALKLLRGEVANAAFPPDPKKGVL
N

*Figure 12B*

Figure 13:
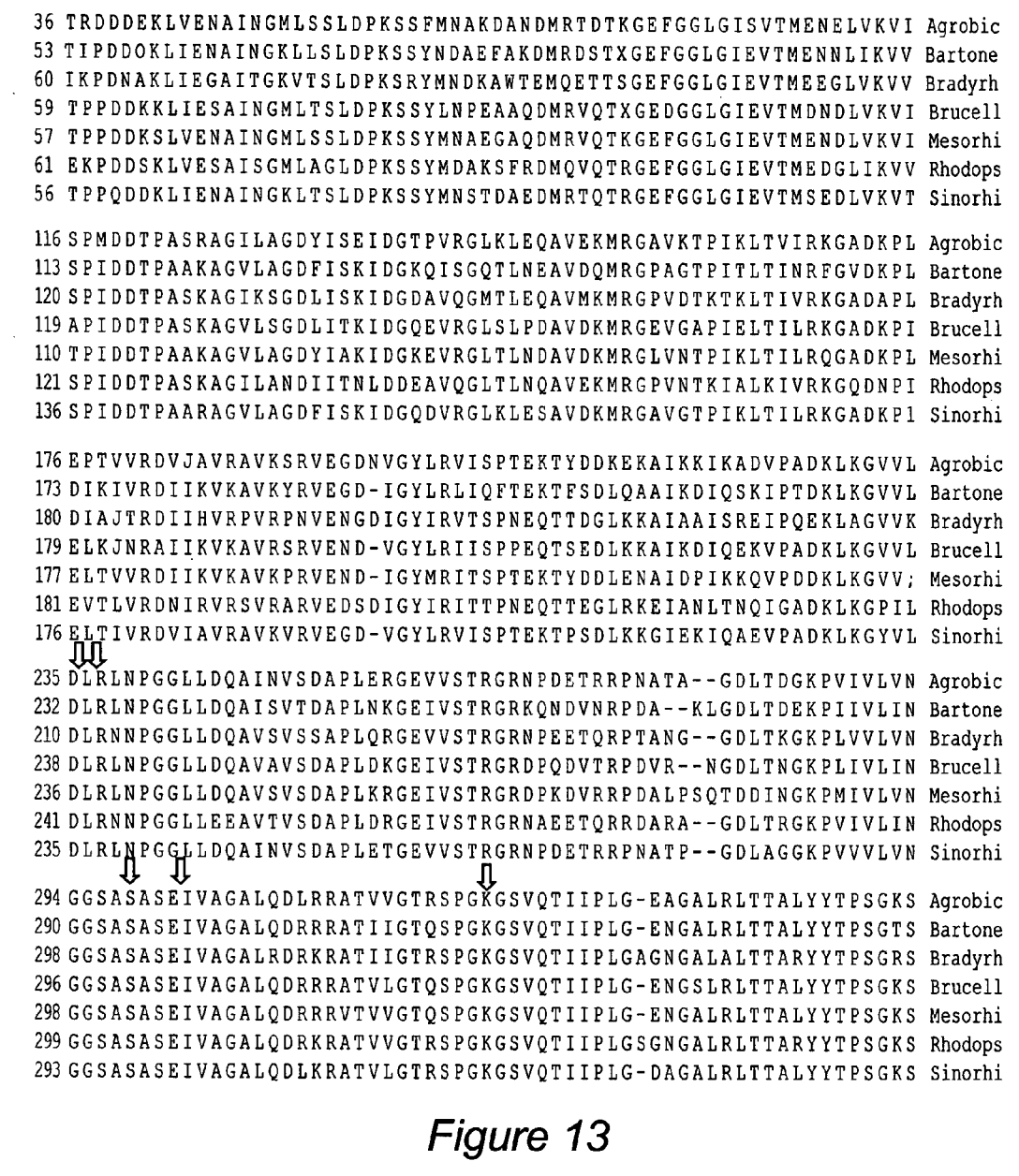

36 TRDDDEKLVENAINGMLSSLDPKSSFMNAKDANDMRTDTKGEFGGLGISVTMENELVKVI Agrobic
53 TIPDDOKLIENAINGKLLSLDPKSSYNDAEFAKDMRDSTXGEFGGLGIEVTMENNLIKVV Bartone
60 IKPDNAKLIEGAITGKVTSLDPKSRYMNDKAWTEMQETTSGEFGGLGIEVTMEEGLVKVV Bradyrh
59 TPPDDKKLIESAINGMLTSLDPKSSYLNPEAAQDMRVQTXGEDGGLGIEVTMDNDLVKVI Brucell
57 TPPDDKSLVENAINGMLSSLDPKSSYMNAEGAQDMRVQTKGEFGGLGIEVTMENDLVKVI Mesorhi
61 EKPDDSKLVESAISGMLAGLDPKSSYMDAKSFRDMQVQTRGEFGGLGIEVTMEDGLIKVV Rhodops
56 TPPQDDKLIENAINGKLTSLDPKSSYMNSTDAEDMRTQTRGEFGGLGIEVTMSEDLVKVT Sinorhi 116 SPMDDTPASRAGILAGDYISEIDGTPVRGLKLEQAVEKMRGAVKTPIKLTVIRKGADKPL Agrobic
113 SPIDDTPAAKAGVLAGDFISKIDGKQISGQTLNEAVDQMRGPAGTPITLTINRFGVDKPL Bartone
120 SPIDDTPASKAGIKSGDLISKIDGDAVQGMTLEQAVMKMRGPVDTKTKLTIVRKGADAPL Bradyrh
119 APIDDTPASKAGVLSGDLITKIDGQEVRGLSLPDAVDKMRGEVGAPIELTILRKGADKPI Brucell
110 TPIDDTPAAKAGVLAGDYIAKIDGKEVRGLTLNDAVDKMRGLVNTPIKLTILRQGADKPL Mesorhi
121 SPIDDTPASKAGILANDIITNLDDEAVQGLTLNQAVEKMRGPVNTKIALKIVRKGQDNPI Rhodops
136 SPIDDTPAARAGVLAGDFISKIDGQDVRGLKLESAVDKMRGAVGTPIKLTILRKGADKPl Sinorhi 176 EPTVVRDVJAVRAVKSRVEGDNVGYLRVISPTEKTYDDKEKAIKKIKADVPADKLKGVVL Agrobic
173 DIKIVRDIIKVKAVKYRVEGD-IGYLRLIQFTEKTFSDLQAAIKDIQSKIPTDKLKGVVL Bartone
180 DIAJTRDIIHVRPVRPNVENGDIGYIRVTSPNEQTTDGLKKAIAAISREIPQEKLAGVVK Bradyrh
179 ELKJNRAIIKVKAVRSRVEND-VGYLRIISPPEQTSEDLKKAIKDIQEKVPADKLKGVVL Brucell
177 ELTVVRDIIKVKAVKPRVEND-IGYMRITSPTEKTYDDLENAIDPIKKQVPDDKLKGVV; Mesorhi
181 EVTLVRDNIRVRSVRARVEDSDIGYIRITTPNEQTTEGLRKEIANLTNQIGADKLKGPIL Rhodops
176 ELTIVRDVIAVRAVKVRVEGD-VGYLRVISPTEKTPSDLKKGIEKIQAEVPADKLKGYVL Sinorhi 235 DLRLNPGGLLDQAINVSDAPLERGEVVSTRGRNPDETRRPNATA--GDLTDGKPVIVLVN Agrobic
232 DLRLNPGGLLDQAISVTDAPLNKGEIVSTRGRKQNDVNRPDA--KLGDLTDEKPIIVLIN Bartone
210 DLRNNPGGLLDQAVSVSSAPLQRGEVVSTRGRNPEETQRPTANG--GDLTKGKPLVVLVN Bradyrh
238 DLRLNPGGLLDQAVAVSDAPLDKGEIVSTRGRDPQDVTRPDVR--NGDLTNGKPLIVLIN Brucell
236 DLRLNPGGLLDQAVSVSDAPLKRGEIVSTRGRDPKDVRRPDALPSQTDDINGKPMIVLVN Mesorhi
241 DLRNNPGGLLEEAVTVSDAPLDRGEIVSTRGRNAEETQRRDARA--GDLTRGKPVIVLIN Rhodops
235 DLRLNPGGLLDQAINVSDAPLETGEVVSTRGRNPDETRRPNATP--GDLAGGKPVVVLVN Sinorhi 294 GGSASASEIVAGALQDLRRATVVGTRSPGKGSVQTIIPLG-EAGALRLTTALYYTPSGKS Agrobic
290 GGSASASEIVAGALQDRRRATIIGTQSPGKGSVQTIIPLG-ENGALRLTTALYYTPSGTS Bartone
298 GGSASASEIVAGALRDRKRATIIGTRSPGKGSVQTIIPLGAGNGALALTTARYYTPSGRS Bradyrh
296 GGSASASEIVAGALQDRRRATVLGTQSPGKGSVQTIIPLG-ENGSLRLTTALYYTPSGKS Brucell
298 GGSASASEIVAGALQDRRRVTVVGTQSPGKGSVQTIIPLG-ENGALRLTTALYYTPSGKS Mesorhi
299 GGSASASEIVAGALQDRKRATVVGTRSPGKGSVQTIIPLGSGNGALRLTTARYYTPSGKS Rhodops
293 GGSASASEIVAGALQDLKRATVLGTRSPGKGSVQTIIPLG-DAGALRLTTALYYTPSGKS Sinorhi

*Figure 13* atgat acgtaaactg tcgctgctgttcgccggggc ccttctgggg gcatccgcca tggtgatggt ccagggcgca
ccagcttccaccgcttttgc ggcaggaaaa gacagcgatg tctataagga gctggctctt ttcggcgatattttcgagcg
tgtacgcgcg caatatgtga cgccgcccga cgacaagaag ctgatcgagagcgccatcaa tggcatgctg acttctcttg
atccccattc gtcctatctc aacccggaagccgcgcagga catgcgtgtg cagaccaagg gtgagtttgg cggccttggc
atcgaagtcaccatggacaa cgatctcgtg aaggtcatcg cgccgatcga cgatacgccc gcctcgaaggccggtgtgct
gtcgggcgac ct=======Deleted region========gatcaat ggcggttcgg ccagtgcctc
ggaaatcgtt gccggtgcgcttcaggatca tcgccgcgcc acggtgctcg gtacgcagtc cttcggcaag ggctctgtgc
agacaatcat cccgcttggc gaaaacggtt cgctgcgtct gacgacggcg ctttattacacgccgtctgg caagtcgatc
cagggcaagg gcattacgcc ggacatcaag gtggatcagccgctgccgcc ggaacttaaa ggcgaggacg
ttgttcgcgg cgaatccgaa ctcaagggccatatcaaggg caatgccgaa gatgcgagcg gctccggttc gtcggcttat
gttccgcctgatccgaagga tgatctccag ctcaatgagg cactgaagct tctgcggggc gaagtggccaatgccgcttt
cccgccggac ccgaaaaagg gcgtgctgaa ctga

*Figure 14A*

MIRKLSLLFAGALLGASAMVMVQGAPASTAFAAGKDSDVYKELALFGDIFERVR
AQYVTPPDDKKLIESAINGMLTSLDPHSSYLNPEAAQDMRVQTKGEFGGLGIEVT
MDNDLVKVIAPIDDTPASKAGVLSGD===Deleted region ====
INGGSASASEIVAGALQDHRRATVLGTQSFGKGSVQTIIPLGENGSLRLTTALYYT
PSGKSIQGKGITPDIKVDQPLPPELKGEDVVRGESELKGHIKGNAEDASGSGSSAY
VPPDPKDDLQLNEALKLLRGEVANAAFPPDPKKGVLN

*Figure 14B* gatcacca agatcgacgg acaggaagtg cgcggccttt cgctgaccga cgctgtggac aagatgcgcg
gcgaggttgg tgcgccaatc gaactgacga tcctgcgcaa gggcgccgac aagccgatca cgctcaagat
caatcgcgcc attatcaagg tgaaggcggt tcgctcgcgc gttgagaatg atgttggcta tctgcgtatc atctcgttta
ccgaacagac ctctgaagac ctcaagaagg cgatcaagga cattcaggaa aaggttcccg ctgacaagct
caagggctat gtgctcgacc ttcgtctcaa tccgggcggc cttctggatc aggcggttgc cgtttccgat gccttcctcg
acaagggcga gatcgtttcc acccgtggcc gcgatccgca ggatgtgacc cgtttcgatg tccgtaaggg
tgacctgacg aatggcaagc cgctgatcgt tct

*Figure 14C*

SEQUENCE LISTING

```
<160> NUMBER OF SEQ ID NOS: 20

<210> SEQ ID NO 1
<211> LENGTH: 1275
<212> TYPE: DNA
<213> ORGANISM: Brucella suis

<400> SEQUENCE: 1

tcagttcagc acgccctttt tcgggtccgg cgggaaagcg gcattgggca cttcgccccg      60
```

-continued

```
cagaagcttc agtgcctcat tgagctggag atcatccttc ggatcaggcg gaacataagc    120

cgacgaaccg gagccgctcg catcttcggc attgcccttg atatggccct tgagttcgga    180

ttcgccgcga acaacgtcct cgcctttaag ttccggcggc agcggctgat ccaccttgat    240

gtccggcgta atgcccttgc cctggatcga cttgccagac ggcgtgtaat aaagcgccgt    300

cgtcagacgc agcgaaccgt tttcgccaag cgggatgatt gtctgcacag agcccttgcc    360

gaaggactgc gtaccgagca ccgtggcgcg gcgatgatcc tgaagcgcac cggcaacgat    420

ttccgaggca ctggccgaac cgccattgat cagaacgatc agcggcttgc cattcgtcag    480

gtcaccctta cgggcatcga aacgggtcac atcctgcgga tcgcggccac gggtggaaac    540

gatctcgccc ttgtcgagga aggcatcgga aacggcaacc gcctgatcca gaaggccgcc    600

cggattgaga cgaaggtcga gcacatagcc cttgagcttg tcagcgggaa ccttttcctg    660

aatgtccttg atcgccttct tgaggtcttc agaggtctgt tcggtaaacg agatgatacg    720

cagatagcca acatcattct caacgcgcga gcgaaccgcc ttcaccttga taatggcgcg    780

attgatcttg agcgtgatcg gcttgtcggc gcccttgcgc aggatcgtca gttcgattgg    840

cgcaccaacc tcgccgcgca tcttgtccac agcgtcggtc agcgaaaggc cgcgcacttc    900

ctgtccgtcg atcttggtga tcaggtcgcc cgacagcaca ccggccttcg aggcgggcgt    960

atcgtcgatc ggcgcgatga ccttcacgag atcattgtcc atggtgactt cgatgccaag   1020

gccgccaaac tcacccttgg tctgcacacg catgtcctgc gcggcttccg ggttgagata   1080

ggacgaatgg ggatcaagag aagtcagcat gccattgatg gcgctctcga tcagcttctt   1140

gtcgtcgggc ggcgtcacat attgcgcgcg tacacgctcg aaaatatcgc cgaaaagagc   1200

cagctcctta tagacatcgc tgtcttttcc tgccgcaaaa gcggtggaag ctggtgcgcc   1260

ctggaccatc accat                                                    1275
```

<210> SEQ ID NO 2
<211> LENGTH: 424
<212> TYPE: PRT
<213> ORGANISM: Brucella suis

<400> SEQUENCE: 2

```
Met Val Met Val Gln Gly Ala Pro Ala Ser Thr Ala Phe Ala Ala Gly
1               5                   10                  15

Lys Asp Ser Asp Val Tyr Lys Glu Leu Ala Leu Phe Gly Asp Ile Phe
            20                  25                  30

Glu Arg Val Arg Ala Gln Tyr Val Thr Pro Pro Asp Asp Lys Lys Leu
        35                  40                  45

Ile Glu Ser Ala Ile Asn Gly Met Leu Thr Ser Leu Asp Pro His Ser
    50                  55                  60

Ser Tyr Leu Asn Pro Glu Ala Ala Gln Asp Met Arg Val Gln Thr Lys
65                  70                  75                  80

Gly Glu Phe Gly Gly Leu Gly Ile Glu Val Thr Met Asp Asn Asp Leu
                85                  90                  95

Val Lys Val Ile Ala Pro Ile Asp Asp Thr Pro Ala Ser Lys Ala Gly
            100                 105                 110

Val Leu Ser Gly Asp Leu Ile Thr Lys Ile Asp Gly Gln Glu Val Arg
        115                 120                 125

Gly Leu Ser Leu Thr Asp Ala Val Asp Lys Met Arg Gly Glu Val Gly
    130                 135                 140

Ala Pro Ile Glu Leu Thr Ile Leu Arg Lys Gly Ala Asp Lys Pro Ile
```

-continued

```
145                 150                 155                 160

Thr Leu Lys Ile Asn Arg Ala Ile Ile Lys Val Lys Ala Val Arg Ser
                165                 170                 175

Arg Val Glu Asn Asp Val Gly Tyr Leu Arg Ile Ile Ser Phe Thr Glu
            180                 185                 190

Gln Thr Ser Glu Asp Leu Lys Lys Ala Ile Lys Asp Ile Gln Glu Lys
        195                 200                 205

Val Pro Ala Asp Lys Leu Lys Gly Tyr Val Leu Asp Leu Arg Leu Asn
    210                 215                 220

Pro Gly Gly Leu Leu Asp Gln Ala Val Ala Val Ser Asp Ala Phe Leu
225                 230                 235                 240

Asp Lys Gly Glu Ile Val Ser Thr Arg Gly Arg Asp Pro Gln Asp Val
                245                 250                 255

Thr Arg Phe Asp Ala Arg Lys Gly Asp Leu Thr Asn Gly Lys Pro Leu
            260                 265                 270

Ile Val Leu Ile Asn Gly Gly Ser Ala Ser Ala Ser Glu Ile Val Ala
        275                 280                 285

Gly Ala Leu Gln Asp His Arg Arg Ala Thr Val Leu Gly Thr Gln Ser
    290                 295                 300

Phe Gly Lys Gly Ser Val Gln Thr Ile Ile Pro Leu Gly Glu Asn Gly
305                 310                 315                 320

Ser Leu Arg Leu Thr Thr Ala Leu Tyr Tyr Thr Pro Ser Gly Lys Ser
                325                 330                 335

Ile Gln Gly Lys Gly Ile Thr Pro Asp Ile Lys Val Asp Gln Pro Leu
            340                 345                 350

Pro Pro Glu Leu Lys Gly Glu Asp Val Val Arg Gly Glu Ser Glu Leu
        355                 360                 365

Lys Gly His Ile Lys Gly Asn Ala Glu Asp Ala Ser Gly Ser Gly Ser
    370                 375                 380

Ser Ala Tyr Val Pro Pro Asp Pro Lys Asp Asp Leu Gln Leu Asn Glu
385                 390                 395                 400

Ala Leu Lys Leu Leu Arg Gly Glu Val Pro Asn Ala Ala Phe Pro Pro
                405                 410                 415

Asp Pro Lys Lys Gly Val Leu Asn
            420
```

<210> SEQ ID NO 3
<211> LENGTH: 471
<212> TYPE: DNA
<213> ORGANISM: Brucella suis

<400> SEQUENCE: 3

```
atcagaacga tcagcggctt gccattcgtc aggtcaccct tacgggcatc gaaacgggtc      60

acatcctgcg gatcgcggcc acgggtggaa acgatctcgc ccttgtcgag gaaggcatcg     120

gaaacggcaa ccgcctgatc cagaaggccg cccggattga gacgaaggtc gagcacatag     180

cccttgagct tgtcagcggg aaccttttcc tgaatgtcct tgatcgcctt cttgaggtct     240

tcagaggtct gttcggtaaa cgagatgata cgcagatagc caacatcatt ctcaacgcgc     300

gagcgaaccg ccttcacctt gataatggcg cgattgatct tgagcgtgat cggcttgtcg     360

gcgcccttgc gcaggatcgt cagttcgatt ggcgcaccaa cctcgccgcg catcttgtcc     420

acagcgtcgg tcagcgaaag gccgcgcact tcctgtccgt cgatcttggt g              471
```

<210> SEQ ID NO 4

-continued

<211> LENGTH: 804
<212> TYPE: DNA
<213> ORGANISM: Brucella suis

<400> SEQUENCE: 4
tcagttcagc acgccctttt tcgggtccgg cgggaaagcg gcattgggca cttcgccccg 60
cagaagcttc agtgcctcat tgagctggag atcatccttc ggatcaggcg gaacataagc 120
cgacgaaccg gagccgctcg catcttcggc attgcccttg atatggccct tgagttcgga 180
ttcgccgcga acaacgtcct cgcctttaag ttccggcggc agcggctgat ccaccttgat 240
gtccggcgta atgcccttgc cctggatcga cttgccagac ggcgtgtaat aaagcgccgt 300
cgtcagacgc agcgaaccgt tttcgccaag cgggatgatt gtctgcacag agcccttgcc 360
gaaggactgc gtaccgagca ccgtggcgcg gcgatgatcc tgaagcgcac cggcaacgat 420
ttccgaggca ctggccgaac cgccattgat caggtcgccc gacagcacac cggccttcga 480
ggcgggcgta tcgtcgatcg gcgcgatgac cttcacgaga tcattgtcca tggtgacttc 540
gatgccaagg ccgccaaact cacccttggt ctgcacacgc atgtcctgcg cggcttccgg 600
gttgagatag gacgaatggg gatcaagaga agtcagcatg ccattgatgg cgctctcgat 660
cagcttcttg tcgtcgggcg gcgtcacata ttgcgcgcgt acacgctcga aaatatcgcc 720
gaaaagagcc agctccttat agacatcgct gtcttttcct gccgcaaaag cggtggaagc 780
tggtgcgccc tggaccatca ccat 804

<210> SEQ ID NO 5
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 5
ggggtaccgt ggtggactga 20

<210> SEQ ID NO 6
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 6
ggctgcagtc ccgcgttttt gtctt 25

<210> SEQ ID NO 7
<211> LENGTH: 1329
<212> TYPE: DNA
<213> ORGANISM: Brucella melitensis

<400> SEQUENCE: 7
atgatacgta aactgtcgct gctgttcgcc ggggcccttc tgggggcatc cgccatggtg 60
atggtccagg gcgcaccagc ttccaccgct tttgcggcag gaaaagacag cgatgtctat 120
aaggagctgg ctcttttcgg cgatattttc gagcgtgtac gcgcgcaata tgtgacgccg 180
cccgacgaca agaagctgat cgagagcgcc atcaatggca tgctgacttc tcttgatccc 240
cattcgtcct atctcaaccc ggaagccgcg caggacatgc gtgtgcagac caagggtgag 300
tttggcggcc ttggcatcga agtcaccatg gacaacgatc tcgtgaaggt catcgcgccg 360
atcgacgata cgcccgcctc gaaggccggt gtgctgtcgg gcgacctgat caccaagatc 420

-continued

```
gacggacagg aagtgcgcgg cctttcgctg accgacgctg tggacaagat gcgcggcgag    480

gttggtgcgc caatcgaact gacgatcctg cgcaagggcg ccgacaagcc gatcacgctc    540

aagatcaatc gcgccattat caaggtgaag gcggttcgct cgcgcgttga gaatgatgtt    600

ggctatctgc gtatcatctc gtttaccgaa cagacctctg aagacctcaa gaaggcgatc    660

aaggacattc aggaaaaggt tcccgctgac aagctcaagg gctatgtgct cgaccttcgt    720

ctcaatccgg gcggccttct ggatcaggcg gttgccgttt ccgatgcctt cctcgacaag    780

ggcgagatcg tttccacccg tggccgcgat ccgcaggatg tgacccgttt cgatgtccgt    840

aagggtgacc tgacgaatgg caagccgctg atcgttctga tcaatggcgg ttcggccagt    900

gcctcggaaa tcgttgccgg tgcgcttcag gatcatcgcc gcgccacggt gctcggtacg    960

cagtccttcg gcaagggctc tgtgcagaca atcatcccgc ttggcgaaaa cggttcgctg   1020

cgtctgacga cggcgcttta ttacacgccg tctggcaagt cgatccaggg caagggcatt   1080

acgccggaca tcaaggtgga tcagccgctg ccgccggaac ttaaaggcga ggacgttgtt   1140

cgcggcgaat ccgaactcaa gggccatatc aagggcaatg ccgaagatgc gagcggctcc   1200

ggttcgtcgg cttatgttcc gcctgatccg aaggatgatc tccagctcaa tgaggcactg   1260

aagcttctgc ggggcgaagt ggccaatgcc gctttcccgc cggacccgaa aaagggcgtg   1320

ctgaactga                                                           1329


<210> SEQ ID NO 8
<211> LENGTH: 442
<212> TYPE: PRT
<213> ORGANISM: Brucella melitensis

<400> SEQUENCE: 8

Met Ile Arg Lys Leu Ser Leu Leu Phe Ala Gly Ala Leu Leu Gly Ala
1               5                   10                  15

Ser Ala Met Val Met Val Gln Gly Ala Pro Ala Ser Thr Ala Phe Ala
            20                  25                  30

Ala Gly Lys Asp Ser Asp Val Tyr Lys Glu Leu Ala Leu Phe Gly Asp
        35                  40                  45

Ile Phe Glu Arg Val Arg Ala Gln Tyr Val Thr Pro Pro Asp Asp Lys
    50                  55                  60

Lys Leu Ile Glu Ser Ala Ile Asn Gly Met Leu Thr Ser Leu Asp Pro
65                  70                  75                  80

His Ser Ser Tyr Leu Asn Pro Glu Ala Ala Gln Asp Met Arg Val Gln
                85                  90                  95

Thr Lys Gly Glu Phe Gly Gly Leu Gly Ile Glu Val Thr Met Asp Asn
            100                 105                 110

Asp Leu Val Lys Val Ile Ala Pro Ile Asp Asp Thr Pro Ala Ser Lys
        115                 120                 125

Ala Gly Val Leu Ser Gly Asp Leu Ile Thr Lys Ile Asp Gly Gln Glu
    130                 135                 140

Val Arg Gly Leu Ser Leu Thr Asp Ala Val Asp Lys Met Arg Gly Glu
145                 150                 155                 160

Val Gly Ala Pro Ile Glu Leu Thr Ile Leu Arg Lys Gly Ala Asp Lys
                165                 170                 175

Pro Ile Thr Leu Lys Ile Asn Arg Ala Ile Ile Lys Val Lys Ala Val
            180                 185                 190

Arg Ser Arg Val Glu Asn Asp Val Gly Tyr Leu Arg Ile Ile Ser Phe
        195                 200                 205
```

-continued

Thr Glu Gln Thr Ser Glu Asp Leu Lys Lys Ala Ile Lys Asp Ile Gln
    210                 215                 220

Glu Lys Val Pro Ala Asp Lys Leu Lys Gly Tyr Val Leu Asp Leu Arg
225                 230                 235                 240

Leu Asn Pro Gly Gly Leu Leu Asp Gln Ala Val Ala Val Ser Asp Ala
                245                 250                 255

Phe Leu Asp Lys Gly Glu Ile Val Ser Thr Arg Gly Arg Asp Pro Gln
            260                 265                 270

Asp Val Thr Arg Phe Asp Val Arg Lys Gly Asp Leu Thr Asn Gly Lys
        275                 280                 285

Pro Leu Ile Val Leu Ile Asn Gly Gly Ser Ala Ser Ala Ser Glu Ile
    290                 295                 300

Val Ala Gly Ala Leu Gln Asp His Arg Arg Ala Thr Val Leu Gly Thr
305                 310                 315                 320

Gln Ser Phe Gly Lys Gly Ser Val Gln Thr Ile Ile Pro Leu Gly Glu
                325                 330                 335

Asn Gly Ser Leu Arg Leu Thr Thr Ala Leu Tyr Tyr Thr Pro Ser Gly
            340                 345                 350

Lys Ser Ile Gln Gly Lys Gly Ile Thr Pro Asp Ile Lys Val Asp Gln
        355                 360                 365

Pro Leu Pro Pro Glu Leu Lys Gly Glu Asp Val Val Arg Gly Glu Ser
    370                 375                 380

Glu Leu Lys Gly His Ile Lys Gly Asn Ala Glu Asp Ala Ser Gly Ser
385                 390                 395                 400

Gly Ser Ser Ala Tyr Val Pro Pro Asp Pro Lys Asp Asp Leu Gln Leu
                405                 410                 415

Asn Glu Ala Leu Lys Leu Leu Arg Gly Glu Val Ala Asn Ala Ala Phe
            420                 425                 430

Pro Pro Asp Pro Lys Lys Gly Val Leu Asn
        435                 440

<210> SEQ ID NO 9
<211> LENGTH: 858
<212> TYPE: DNA
<213> ORGANISM: Brucella melitensis

<400> SEQUENCE: 9
atgatacgta aactgtcgct gctgttcgcc ggggcccttc tgggggcatc cgccatggtg 60
atggtccagg gcgcaccagc ttccaccgct tttgcggcag gaaaagacag cgatgtctat 120
aaggagctgg ctcttttcgg cgatattttc gagcgtgtac gcgcgcaata tgtgacgccg 180
cccgacgaca agaagctgat cgagagcgcc atcaatggca tgctgacttc tcttgatccc 240
cattcgtcct atctcaaccc ggaagccgcg caggacatgc gtgtgcagac caagggtgag 300
tttggcggcc ttggcatcga agtcaccatg gacaacgatc tcgtgaaggt catcgcgccg 360
atcgacgata cgcccgcctc gaaggccggt gtgctgtcgg gcgacctgat caatggcggt 420
tcggccagtg cctcggaaat cgttgccggt gcgcttcagg atcatcgccg cgccacggtg 480
ctcggtacgc agtccttcgg caagggctct gtgcagacaa tcatcccgct tggcgaaaac 540
ggttcgctgc gtctgacgac ggcgctttat tacacgccgt ctggcaagtc gatccagggc 600
aagggcatta cgccggacat caaggtggat cagccgctgc cgccggaact taaaggcgag 660
gacgttgttc gcggcgaatc cgaactcaag ggccatatca agggcaatgc cgaagatgcg 720
agcggctccg gttcgtcggc ttatgttccg cctgatccga aggatgatct ccagctcaat 780

-continued gaggcactga agcttctgcg gggcgaagtg gccaatgccg ctttcccgcc ggacccgaaa 840
aagggcgtgc tgaactga 858

<210> SEQ ID NO 10
<211> LENGTH: 284
<212> TYPE: PRT
<213> ORGANISM: Brucella melitensis

<400> SEQUENCE: 10

Met Ile Arg Lys Leu Ser Leu Leu Phe Ala Gly Ala Leu Leu Gly Ala
1 5 10 15

Ser Ala Met Val Met Val Gln Gly Ala Pro Ala Ser Thr Ala Phe Ala
20 25 30

Ala Gly Lys Asp Ser Asp Val Tyr Lys Glu Leu Ala Leu Phe Gly Asp
35 40 45

Ile Phe Glu Arg Val Arg Ala Gln Tyr Val Thr Pro Pro Asp Asp Lys
50 55 60

Lys Leu Ile Glu Ser Ala Ile Asn Gly Met Leu Thr Ser Leu Asp Pro
65 70 75 80

His Ser Ser Tyr Leu Asn Pro Glu Ala Ala Gln Asp Met Arg Val Gln
85 90 95

Thr Lys Gly Glu Phe Gly Gly Leu Gly Ile Glu Val Thr Met Asp Asn
100 105 110

Asp Leu Val Lys Val Ile Ala Pro Ile Asp Asp Thr Pro Ala Ser Lys
115 120 125

Ala Gly Val Leu Ser Gly Asp Ile Asn Gly Gly Ser Ala Ser Ala Ser
130 135 140

Glu Ile Val Ala Gly Ala Leu Gln Asp His Arg Arg Ala Thr Val Leu
145 150 155 160

Gly Thr Gln Ser Phe Gly Lys Gly Ser Val Gln Thr Ile Ile Pro Leu
165 170 175

Gly Glu Asn Gly Ser Leu Arg Leu Thr Thr Ala Leu Tyr Tyr Thr Pro
180 185 190

Ser Gly Lys Ser Ile Gln Gly Lys Gly Ile Thr Pro Asp Ile Lys Val
195 200 205

Asp Gln Pro Leu Pro Pro Glu Leu Lys Gly Glu Asp Val Val Arg Gly
210 215 220

Glu Ser Glu Leu Lys Gly His Ile Lys Gly Asn Ala Glu Asp Ala Ser
225 230 235 240

Gly Ser Gly Ser Ser Ala Tyr Val Pro Pro Asp Pro Lys Asp Asp Leu
245 250 255

Gln Leu Asn Glu Ala Leu Lys Leu Leu Arg Gly Glu Val Ala Asn Ala
260 265 270

Ala Phe Pro Pro Asp Pro Lys Lys Gly Val Leu Asn
275 280

<210> SEQ ID NO 11
<211> LENGTH: 471
<212> TYPE: DNA
<213> ORGANISM: Brucella melitensis

<400> SEQUENCE: 11
gatcaccaag atcgacggac aggaagtgcg cggcctttcg ctgaccgacg ctgtggacaa 60
gatgcgcggc gaggttggtg cgccaatcga actgacgatc ctgcgcaagg gcgccgacaa 120

-continued

```
gccgatcacg ctcaagatca atcgcgccat tatcaaggtg aaggcggttc gctcgcgcgt    180

tgagaatgat gttggctatc tgcgtatcat ctcgtttacc gaacagacct ctgaagacct    240

caagaaggcg atcaaggaca ttcaggaaaa ggttcccgct gacaagctca agggctatgt    300

gctcgacctt cgtctcaatc cgggcggcct tctggatcag gcggttgccg tttccgatgc    360

cttcctcgac aagggcgaga tcgtttccac ccgtggccgc gatccgcagg atgtgacccg    420

tttcgatgtc cgtaagggtg acctgacgaa tggcaagccg ctgatcgttc t             471
```

<210> SEQ ID NO 12
<211> LENGTH: 20
<212> TYPE: DNA
<213> ORGANISM: Artificial
<220> FEATURE:
<223> OTHER INFORMATION: synthetic oligonucleotide forward primer

<400> SEQUENCE: 12

```
ggggtaccgt ggtggactga                                                  20
```

<210> SEQ ID NO 13
<211> LENGTH: 25
<212> TYPE: DNA
<213> ORGANISM: Artificial
<220> FEATURE:
<223> OTHER INFORMATION: synthetic oligonucleotide reverse primer

<400> SEQUENCE: 13

```
ggctgcagtc ccgcgttttt gtctt                                            25
```

<210> SEQ ID NO 14
<211> LENGTH: 297
<212> TYPE: PRT
<213> ORGANISM: Agrobacterium tumefaciens

<400> SEQUENCE: 14

```
Thr Pro Pro Asp Asp Glu Lys Leu Val Glu Asn Ala Ile Asn Gly Met
1               5                   10                  15

Leu Ser Ser Leu Asp Pro His Ser Ser Phe Met Asn Ala Lys Asp Ala
            20                  25                  30

Asn Asp Met Arg Thr Gln Thr Lys Gly Glu Phe Gly Gly Leu Gly Ile
        35                  40                  45

Glu Val Thr Met Glu Asn Glu Leu Val Lys Val Ile Ser Pro Met Asp
    50                  55                  60

Asp Thr Pro Ala Ser Arg Ala Gly Ile Leu Ala Gly Asp Tyr Ile Ser
65                  70                  75                  80

Glu Ile Asp Gly Thr Pro Val Arg Gly Leu Lys Leu Glu Gln Ala Val
                85                  90                  95

Glu Lys Met Arg Gly Ala Val Lys Thr Pro Ile Lys Leu Thr Val Ile
            100                 105                 110

Arg Lys Gly Ala Asp Lys Pro Leu Glu Phe Thr Val Val Arg Asp Val
        115                 120                 125

Ile Ala Val Arg Ala Val Lys Ser Arg Val Glu Gly Asp Asn Val Gly
    130                 135                 140

Tyr Leu Arg Val Ile Ser Phe Thr Glu Lys Thr Tyr Asp Asp Leu Glu
145                 150                 155                 160

Lys Ala Ile Lys Lys Ile Lys Ala Asp Val Pro Ala Asp Lys Leu Lys
                165                 170                 175

Gly Tyr Val Leu Asp Leu Arg Leu Asn Pro Gly Gly Leu Leu Asp Gln
            180                 185                 190
```

-continued

```
Ala Ile Asn Val Ser Asp Ala Phe Leu Glu Arg Gly Glu Val Val Ser
        195                 200                 205

Thr Arg Gly Arg Asn Pro Asp Glu Thr Arg Arg Phe Asn Ala Thr Ala
    210                 215                 220

Gly Asp Leu Thr Asp Gly Lys Pro Val Ile Val Leu Val Asn Gly Gly
225                 230                 235                 240

Ser Ala Ser Ala Ser Glu Ile Val Ala Gly Ala Leu Gln Asp Leu Arg
                245                 250                 255

Arg Ala Thr Val Val Gly Thr Arg Ser Phe Gly Lys Gly Ser Val Gln
            260                 265                 270

Thr Ile Ile Pro Leu Gly Glu Ala Gly Ala Leu Arg Leu Thr Thr Ala
        275                 280                 285

Leu Tyr Tyr Thr Pro Ser Gly Lys Ser
    290                 295


<210> SEQ ID NO 15
<211> LENGTH: 296
<212> TYPE: PRT
<213> ORGANISM: Bartonella quintana

<400> SEQUENCE: 15

Thr Ile Pro Asp Asp Gln Lys Leu Ile Glu Asn Ala Ile Asn Gly Met
1               5                   10                  15

Leu Leu Ser Leu Asp Pro His Ser Ser Tyr Met Asp Ala Glu Lys Ala
            20                  25                  30

Lys Asp Met Arg Asp Ser Thr Lys Gly Glu Phe Gly Gly Leu Gly Ile
        35                  40                  45

Glu Val Thr Met Glu Asn Asn Leu Ile Lys Val Val Ser Pro Ile Asp
    50                  55                  60

Asp Thr Pro Ala Ala Lys Ala Gly Val Leu Ala Gly Asp Phe Ile Ser
65                  70                  75                  80

Lys Ile Asp Gly Lys Gln Ile Ser Gly Gln Thr Leu Asn Glu Ala Val
                85                  90                  95

Asp Gln Met Arg Gly Pro Ala Gly Thr Pro Ile Thr Leu Thr Ile Asn
            100                 105                 110

Arg Phe Gly Val Asp Lys Pro Leu Asp Ile Lys Ile Val Arg Asp Ile
        115                 120                 125

Ile Lys Val Lys Ala Val Lys Tyr Arg Val Glu Gly Asp Ile Gly Tyr
    130                 135                 140

Leu Arg Leu Ile Gln Phe Thr Glu Lys Thr Phe Ser Asp Leu Gln Ala
145                 150                 155                 160

Ala Ile Lys Asp Ile Gln Ser Lys Ile Pro Thr Asp Lys Leu Lys Gly
                165                 170                 175

Tyr Val Leu Asp Leu Arg Leu Asn Pro Gly Gly Leu Leu Asp Gln Ala
            180                 185                 190

Ile Ser Val Thr Asp Ala Phe Leu Asn Lys Gly Glu Ile Val Ser Thr
        195                 200                 205

Arg Gly Arg Lys Gln Asn Asp Val Met Arg Phe Asp Ala Lys Leu Gly
    210                 215                 220

Asp Leu Thr Asp Glu Lys Pro Ile Ile Val Leu Ile Asn Gly Gly Ser
225                 230                 235                 240

Ala Ser Ala Ser Glu Ile Val Ala Gly Ala Leu Gln Asp His Arg Arg
                245                 250                 255

Ala Thr Ile Ile Gly Thr Gln Ser Phe Gly Lys Gly Ser Val Gln Thr
```

-continued

```
            260                 265                 270

Ile Ile Pro Leu Gly Glu Asn Gly Ala Leu Arg Leu Thr Thr Ala Leu
        275                 280                 285

Tyr Tyr Thr Pro Ser Gly Thr Ser
    290                 295


<210> SEQ ID NO 16
<211> LENGTH: 298
<212> TYPE: PRT
<213> ORGANISM: Bradyrhizobium japonicum

<400> SEQUENCE: 16

Glu Lys Pro Asp Asn Ala Lys Leu Ile Glu Gly Ala Ile Thr Gly Met
1               5                   10                  15

Val Thr Ser Leu Asp Pro His Ser Arg Tyr Met Asn Asp Lys Ala Trp
            20                  25                  30

Thr Glu Met Gln Glu Thr Thr Ser Gly Glu Phe Gly Gly Leu Gly Ile
        35                  40                  45

Glu Val Thr Met Glu Glu Gly Leu Val Lys Val Val Ser Pro Ile Asp
    50                  55                  60

Asp Thr Pro Ala Ser Lys Ala Gly Ile Met Ser Gly Asp Leu Ile Ser
65                  70                  75                  80

Lys Ile Asp Gly Asp Ala Val Gln Gly Met Thr Leu Glu Gln Ala Val
                85                  90                  95

Asn Lys Met Lys Gly Pro Val Asp Thr Lys Thr Lys Leu Thr Ile Val
            100                 105                 110

Arg Lys Gly Ala Asp Ala Pro Leu Asp Ile Ala Ile Thr Arg Glu Ile
        115                 120                 125

Ile His Val Arg Pro Val Arg Phe His Val Glu Asn Gly Asp Ile Gly
    130                 135                 140

Tyr Ile Arg Val Thr Ser Phe Asn Glu Gln Thr Thr Asp Gly Leu Lys
145                 150                 155                 160

Lys Ala Ile Ala Ala Ile Ser Arg Glu Ile Pro Gln Glu Lys Leu Ala
                165                 170                 175

Gly Tyr Val Met Asp Leu Arg Asn Asn Pro Gly Gly Leu Leu Asp Gln
            180                 185                 190

Ala Val Ser Val Ser Ser Ala Phe Leu Gln Arg Gly Glu Val Val Ser
        195                 200                 205

Thr Arg Gly Arg Asn Pro Glu Glu Thr Gln Arg Phe Thr Ala His Gly
    210                 215                 220

Gly Asp Leu Thr Lys Gly Lys Pro Leu Val Val Leu Val Asn Gly Gly
225                 230                 235                 240

Ser Ala Ser Ala Ser Glu Ile Val Ala Gly Ala Leu His Asp His Lys
                245                 250                 255

Arg Ala Thr Ile Ile Gly Thr Arg Ser Phe Gly Lys Gly Ser Val Gln
            260                 265                 270

Thr Ile Ile Pro Leu Gly Ala Gly Asn Gly Ala Leu Ala Leu Thr Thr
        275                 280                 285

Ala Arg Tyr Tyr Thr Pro Ser Gly Arg Ser
    290                 295


<210> SEQ ID NO 17
<211> LENGTH: 296
<212> TYPE: PRT
<213> ORGANISM: Brucella melitensis
```

-continued

<400> SEQUENCE: 17

```
Thr Pro Pro Asp Asp Lys Lys Leu Ile Glu Ser Ala Ile Asn Gly Met
1               5                   10                  15

Leu Thr Ser Leu Asp Pro His Ser Ser Tyr Leu Asn Pro Glu Ala Ala
            20                  25                  30

Gln Asp Met Arg Val Gln Thr Lys Gly Glu Phe Gly Gly Leu Gly Ile
        35                  40                  45

Glu Val Thr Met Asp Asn Asp Leu Val Lys Val Ile Ala Pro Ile Asp
    50                  55                  60

Asp Thr Pro Ala Ser Lys Ala Gly Val Leu Ser Gly Asp Leu Ile Thr
65                  70                  75                  80

Lys Ile Asp Gly Gln Glu Val Arg Gly Leu Ser Leu Thr Asp Ala Val
                85                  90                  95

Asp Lys Met Arg Gly Glu Val Gly Ala Pro Ile Glu Leu Thr Ile Leu
            100                 105                 110

Arg Lys Gly Ala Asp Lys Pro Ile Thr Leu Lys Ile Asn Arg Ala Ile
        115                 120                 125

Ile Lys Val Lys Ala Val Arg Ser Arg Val Glu Asn Asp Val Gly Tyr
    130                 135                 140

Leu Arg Ile Ile Ser Phe Thr Glu Gln Thr Ser Glu Asp Leu Lys Lys
145                 150                 155                 160

Ala Ile Lys Asp Ile Gln Glu Lys Val Pro Ala Asp Lys Leu Lys Gly
                165                 170                 175

Tyr Val Leu Asp Leu Arg Leu Asn Pro Gly Gly Leu Leu Asp Gln Ala
            180                 185                 190

Val Ala Val Ser Asp Ala Phe Leu Asp Lys Gly Glu Ile Val Ser Thr
        195                 200                 205

Arg Gly Arg Asp Pro Gln Asp Val Thr Arg Phe Asp Val Arg Lys Gly
    210                 215                 220

Asp Leu Thr Asn Gly Lys Pro Leu Ile Val Leu Ile Asn Gly Gly Ser
225                 230                 235                 240

Ala Ser Ala Ser Glu Ile Val Ala Gly Ala Leu Gln Asp His Arg Arg
                245                 250                 255

Ala Thr Val Leu Gly Thr Gln Ser Phe Gly Lys Gly Ser Val Gln Thr
            260                 265                 270

Ile Ile Pro Leu Gly Glu Asn Gly Ser Leu Arg Leu Thr Thr Ala Leu
        275                 280                 285

Tyr Tyr Thr Pro Ser Gly Lys Ser
    290                 295
```

<210> SEQ ID NO 18
<211> LENGTH: 298
<212> TYPE: PRT
<213> ORGANISM: Mesorhizobium loti

<400> SEQUENCE: 18

```
Thr Pro Pro Asp Asp Lys Ser Leu Val Glu Asn Ala Ile Asn Gly Met
1               5                   10                  15

Leu Ser Ser Leu Asp Pro His Ser Ser Tyr Met Asn Ala Glu Gln Ala
            20                  25                  30

Gln Asp Met Arg Val Gln Thr Lys Gly Glu Phe Gly Gly Leu Gly Ile
        35                  40                  45

Glu Val Thr Met Glu Asn Asp Leu Val Lys Val Ile Thr Pro Ile Asp
    50                  55                  60
```

-continued

Asp Thr Pro Ala Ala Lys Ala Gly Val Leu Ala Gly Asp Tyr Ile Ala
65 70 75 80

Lys Ile Asp Gly Glu Glu Val Arg Gly Leu Thr Leu Asn Asp Ala Val
85 90 95

Asp Lys Met Arg Gly Leu Val Asn Thr Pro Ile Lys Leu Thr Ile Leu
100 105 110

Arg Gln Gly Ala Asp Lys Pro Ile Glu Leu Thr Val Val Arg Asp Ile
115 120 125

Ile Lys Val Lys Ala Val Lys Phe Arg Val Glu Asn Asp Ile Gly Tyr
130 135 140

Met Lys Ile Thr Ser Phe Thr Glu Lys Thr Tyr Asp Asp Leu Glu Asn
145 150 155 160

Ala Ile Asp Thr Ile Lys Lys Gln Val Pro Asp Asp Lys Leu Lys Gly
165 170 175

Tyr Val Leu Asp Leu Arg Leu Asn Pro Gly Gly Leu Leu Asp Gln Ala
180 185 190

Val Ser Val Ser Asp Ala Phe Leu Lys Arg Gly Glu Ile Val Ser Thr
195 200 205

Arg Gly Arg Asp Pro Lys Asp Val Thr Arg Phe Asp Ala Lys Pro Lys
210 215 220

Gln Thr Asp Asp Ile Asn Gly Lys Pro Met Ile Val Leu Val Asn Gly
225 230 235 240

Gly Ser Ala Ser Ala Ser Glu Ile Val Ala Gly Ala Leu Gln Asp Leu
245 250 255

Arg Arg Val Thr Val Val Gly Thr Gln Ser Phe Gly Lys Gly Ser Val
260 265 270

Gln Thr Ile Ile Pro Leu Gly Glu Asn Gly Ala Leu Arg Leu Thr Thr
275 280 285

Ala Leu Tyr Tyr Thr Pro Ser Gly Lys Ser
290 295

<210> SEQ ID NO 19
<211> LENGTH: 298
<212> TYPE: PRT
<213> ORGANISM: Rhodopseudomonas palustris

<400> SEQUENCE: 19

Glu Lys Pro Asp Asp Ser Lys Leu Val Glu Ser Ala Ile Ser Gly Met
1 5 10 15

Leu Ala Gly Leu Asp Pro His Ser Ser Tyr Met Asp Ala Lys Ser Phe
20 25 30

Arg Asp Met Gln Val Gln Thr Arg Gly Glu Phe Gly Gly Leu Gly Ile
35 40 45

Glu Val Thr Met Glu Asp Gly Leu Ile Lys Val Val Ser Pro Ile Asp
50 55 60

Asp Thr Pro Ala Ser Lys Ala Gly Ile Leu Ala Asn Asp Ile Ile Thr
65 70 75 80

Asn Leu Asp Asp Glu Ala Val Gln Gly Leu Thr Leu Asn Gln Ala Val
85 90 95

Glu Lys Met Arg Gly Pro Val Asn Thr Lys Ile Arg Leu Lys Ile Val
100 105 110

Arg Lys Gly Gln Asp Asn Pro Ile Glu Val Thr Leu Val Arg Asp Asn
115 120 125

Ile Arg Val Arg Ser Val Arg Ala Arg Val Glu Asp Ser Asp Ile Gly
130 135 140

-continued

```
Tyr Ile Arg Ile Thr Thr Phe Asn Glu Gln Thr Thr Glu Gly Leu Lys
145                 150                 155                 160

Lys Glu Ile Ala Asn Leu Thr Asn Gln Ile Gly Ala Asp Lys Leu Lys
                165                 170                 175

Gly Phe Ile Leu Asp Leu Arg Asn Asn Pro Gly Gly Leu Leu Glu Glu
            180                 185                 190

Ala Val Thr Val Ser Asp Ala Phe Leu Asp Arg Gly Glu Ile Val Ser
        195                 200                 205

Thr Arg Gly Arg Asn Ala Glu Glu Thr Gln Arg Arg Ser Ala His Ala
    210                 215                 220

Gly Asp Leu Thr Lys Gly Lys Pro Val Ile Val Leu Ile Asn Gly Gly
225                 230                 235                 240

Ser Ala Ser Ala Ser Glu Ile Val Ala Gly Ala Leu Gln Asp His Lys
                245                 250                 255

Arg Ala Thr Val Val Gly Thr Arg Ser Phe Gly Lys Gly Ser Val Gln
            260                 265                 270

Thr Ile Ile Pro Leu Gly Ser Gly Asn Gly Ala Leu Arg Leu Thr Thr
        275                 280                 285

Ala Arg Tyr Tyr Thr Pro Ser Gly Lys Ser
    290                 295


<210> SEQ ID NO 20
<211> LENGTH: 296
<212> TYPE: PRT
<213> ORGANISM: Sinorhizobium meliloti

<400> SEQUENCE: 20

Thr Pro Pro Gln Asp Asp Lys Leu Ile Glu Asn Ala Ile Asn Gly Met
1               5                   10                  15

Leu Thr Ser Leu Asp Pro His Ser Ser Tyr Met Asn Ser Thr Asp Ala
            20                  25                  30

Glu Asp Met Arg Thr Gln Thr Arg Gly Glu Phe Gly Gly Leu Gly Ile
        35                  40                  45

Glu Val Thr Met Glu Glu Asp Leu Val Lys Val Thr Ser Pro Ile Asp
    50                  55                  60

Asp Thr Pro Ala Ala Arg Ala Gly Val Leu Ala Gly Asp Phe Ile Ser
65                  70                  75                  80

Lys Ile Asp Gly Gln Asp Val Arg Gly Leu Lys Leu Glu Glu Ala Val
                85                  90                  95

Asp Lys Met Arg Gly Ala Val Gly Thr Pro Ile Lys Leu Thr Ile Leu
            100                 105                 110

Arg Lys Gly Ala Glu Lys Pro Ile Glu Leu Thr Ile Val Arg Asp Val
        115                 120                 125

Ile Ala Val Arg Ala Val Lys Val Arg Val Glu Gly Asp Val Gly Tyr
    130                 135                 140

Leu Arg Val Ile Ser Phe Thr Glu Lys Thr Phe Glu Asp Leu Lys Lys
145                 150                 155                 160

Gly Ile Glu Lys Ile Gln Ala Glu Val Pro Ala Asp Lys Leu Lys Gly
                165                 170                 175

Tyr Val Leu Asp Leu Arg Leu Asn Pro Gly Gly Leu Leu Asp Gln Ala
            180                 185                 190

Ile Asn Val Ser Asp Ala Phe Leu Glu Arg Gly Glu Val Val Ser Thr
        195                 200                 205

Arg Gly Arg Asn Pro Asp Glu Thr Arg Arg Phe Asn Ala Thr Pro Gly
```

-continued

```
    210                 215                 220

Asp Leu Ala Gly Gly Lys Pro Val Val Val Leu Val Asn Gly Gly Ser
225                 230                 235                 240

Ala Ser Ala Ser Glu Ile Val Ala Gly Ala Leu Gln Asp Leu Lys Arg
                245                 250                 255

Ala Thr Val Leu Gly Thr Arg Ser Phe Gly Lys Gly Ser Val Gln Thr
            260                 265                 270

Ile Ile Pro Leu Gly Asp Ala Gly Ala Leu Arg Leu Thr Thr Ala Leu
        275                 280                 285

Tyr Tyr Thr Pro Ser Gly Lys Ser
    290                 295
```

DEVELOPMENT OF A LIVE, ATTENUATED, RECOMBINANT VACCINE FOR BRUCELLOSIS

This application claims benefit of U.S. provisional patent application U.S. 60/541,954, filed Feb. 6, 2004, and is a continuation-in-part of U.S. patent application Ser. No. 11/050,429, filed Feb. 4, 2005, the complete contents of each of which are hereby incorporated by reference.

This invention was made using funds from grants from the United States Department of Agriculture having grant number 1-37181. The United States government may have certain rights in this invention.

BACKGROUND OF THE INVENTION

1. Field of the Invention

The invention generally relates to a vaccine for Brucellosis. In particular, the invention provides an antigenic composition comprising a recombinant, attenuated strain of *Brucella suis* with a deficiency in carboxyl-terminal protease (CtpA) activity.

2. Background of the Invention

Animal brucellosis is a disease affecting many domestic and wild life species. In male animals, this disease causes orchitis (inflammation of the testicles) and may eventually lead to sterility. In female animals, brucellosis causes abortion during the last trimester, retained afterbirth (retaining placenta in the uterus) and weakness in calves at birth. Brucellosis results from infection with bacteria belonging to the genus *Brucella*. On the basis of observed differences in host preference, which have been associated with certain phenotypic characteristics, this genus has been classified for convenience into six nomen species. These are associated with different principal hosts: *B. abortus* (cattle), *B. canis* (dogs), *B. melitensis* (sheep, goats), *B. neotomae* (desert wood rat), *B. ovis* (sheep) and *B. suis* (swine, reindeer). However, *Brucella* species typically can infect a wide variety of hosts, including humans.

Human brucellosis is a zoonotic disease, that is, it is readily passed to humans from other species. Infection in humans is normally acquired either through consumption of contaminated dairy and meat products or by contact with infected animal secretions. Human beings are susceptible to *B. melitensis, B. suis, B. abortus* and *B. canis* in a decreasing order. Brucellosis in humans is characterized by undulant fever, headache, cold sweats and general malaise. The disease can last from a few weeks to several years. If untreated, serious complications leading to death can occur.

Brucellosis among domestic livestock in North America has been largely controlled by using a combination of reliable and accurate diagnostic tests, removal of infected animals, and efficacious vaccines. However, this disease still exists among free-ranging wild life including feral swine (*Sus scrofa*). Infected wild life populations are the most likely source of transmission of brucellosis to humans, and for the possible reintroduction of this disease into domestic livestock. Feral swine populations are present in many regions of the world. Approximately 2 to 3 million feral swine are estimated to be present in the US alone, and feral swine populations in the southern portion of the US are known to be infected with *B. suis*.

Brucellosis among US domestic pig populations is currently controlled by depopulation procedures, a less than ideal strategy. Further, swine brucellosis is recognized as a major threat to domestic pig production in other parts of world. So far, no vaccine has been extensively used or clearly been proven useful against this disease in swine. Therefore, it would be beneficial to have available a vaccine effective against brucellosis in feral and domestic swine.

*B. suis* was the first pathogenic organism weaponized by the U.S. military during the 1950 s. Today it constitutes a potential bioterrorism threat that could be targeted against military personnel, civilians, or food supplies. Early diagnosis of brucellosis is problematic, and the treatment regiment is prolonged antibiotic therapy. However, antibiotic-resistant strains of *Brucella* can be generated easily, and if such strains are used in bio-warfare, use of antibiotics to control brucellosis may not be effective. The Centers for Disease Control and Prevention has listed *Brucella* as a category-B biothreat-agent. Currently, there is no licensed vaccine against brucellosis in humans. Due to its highly infectious nature and the increased likelihood of illegitimate use, it would be beneficial to have available a vaccine that protects humans against this pathogen.

Several animal vaccines against different strains of *Brucella* currently exist.

Cattle vaccine strain RB51: This is an attenuated (less capable of surviving in animals, and less capable of causing disease in animals), rough (incapable of producing the cell-surface antigen called O-side-chain) strain of *B. abortus*. Strain RB51 induces strong cell-mediated immune (CMI) responses and provides protection against brucellosis in bovine and several other animal species. It is the official vaccine approved by USDA to protect cattle against infection with *B. abortus*.

Although very effective in immunizing cattle against *B. abortus*, it is less effective against *B. melitensis* and *B. suis* infections, suggesting that strain RB51 would not be a suitable vaccine for humans, where *B. melitensis* and *B. suis* cause the most severe symptoms. The induction of O-side chain antibodies, in addition to strong CMI, appears to be important for protection against brucellosis in humans. Strain RB51 is rough, and therefore expresses only minimal amounts of O-side chain antigen and does not induce O-side chain antibodies.

In addition, strain RB51 was developed through natural selection procedures, and therefore, its genetic make up is not filly known. Further, strain RB51 is resistant to rifampicin, one of the very few antibiotics available for treatment of humans against brucellosis. Thus, if a human vaccinated with RB51 did become infected, (e.g. an immuno-compromised individual), it would not be possible to treat the infection with standard antibiotic therapy with rifampicin. For these reasons, strain RB51 is not considered a suitable candidate for use as a brucellosis vaccine for humans.

Cattle vaccine strain 19: This strain is able to induce protective immunity in cattle. However, although strain 19 (also known as S19) is of low virulence for cattle, vaccination of pregnant cows can still result in abortions. A less frequent adverse consequence of strain 19 vaccination is the development of an arthropathy associated with *Brucella* antigen-containing immune complexes (but not live organisms) in the affected joints.

Strain 19 is known to be pathogenic for human beings. In addition, this strain was isolated through laboratory selection procedures, and its genetic make up is not understood. Therefore, strain 19 is also not considered a suitable candidate for use as a brucellosis vaccine for humans.

Sheep/goat vaccine strain Rev1: Rev1 vaccine is a live, attenuated *B. melitensis* strain that stimulates protection against infection with *B. melitensis* in sheep and goats and also protects rams against infection with *B. ovis*. Depending on the dose administered during pregnancy, abortions will occur with variable frequency. In cattle, Rev1 gives better protection than strain 19. However, strain Rev1 is also not considered safe as a human vaccine because its genetic makeup is not known, it is pathogenic for human beings, and it is resistant to the antibiotic streptomycin.

SUMMARY OF THE INVENTION

The invention provides compositions and methods for treating and preventing Brucellosis. The methods involve eliciting an immune response to pathogenic, virulent bacteria of the genus *Brucella* by administering a composition comprising attenuated, recombinant *Brucella* strains that exhibit a deficiency in carboxy-terminal protease (CtpA) activity. The compositions may be used as a vaccine in mammals including without limitation swine, reindeer, cattle and humans. In a preferred embodiment, the attenuated *Brucella* strain is a *Brucella suis* strain in which a portion of the CtpA gene has been deleted.

It is an object of this invention to provide an attenuated, recombinant *Brucella* strain with a deficiency in carboxyl-terminal processing protease (CtpA) activity. In one embodiment, the attenuated, recombinant *Brucella* strain is of the species *Brucella suis*. In some embodiments, the CtpA deficiency is caused by deletion of at least a portion of a gene encoding CtpA in the attenuated, recombinant *Brucella* strain. In one embodiment, the attenuated, recombinant *Brucella* is 1330ΔctpA. In further embodiments, the attenuated, recombinant *Brucella* strain is *Brucella abortus, Brucella suis, Brucella melitensis, Brucella neotomae, Brucella canis*, or *Brucella ovis*; and the mammal may be a human, swine, cattle or reindeer.

The invention also provides a method for eliciting an immune response to a *Brucella* species in a mammal, or treating or preventing Brucellosis in a mammal, including vaccinating a mammal against Brucellosis. The method comprises the step of administering to the mammal in a quantity sufficient to elicit an immune response, an attenuated, recombinant *Brucella* strain with a deficiency in carboxyl-terminal processing protease (CtpA) activity. The attenuated, recombinant *Brucella* strain may be of the species *Brucella suis*, and the CtpA deficiency may be caused by deletion of at least a portion of a gene encoding CtpA in the attenuated, recombinant *Brucella* strain. In one embodiment, the attenuated, recombinant *Brucella* strain is 1330ΔctpA. The *Brucella* species may be *Brucella abortus, Brucella suis, Brucella melitensis, Brucella neotomae, Brucella canis*, or *Brucella ovis*, and the mammal may be human, swine, cattle or reindeer.

The invention further provides a composition for eliciting an immune response to *Brucella* species in a mammal. The composition comprises an attenuated, recombinant *Brucella* strain with a deficiency in carboxyl-terminal processing protease (CtpA) activity and, a physiologically suitable carrier. The attenuated, recombinant *Brucella* strain may be of the species *Brucella suis*, and the CtpA deficiency may be caused by deletion of at least a portion of a gene encoding CtpA in the attenuated, recombinant *Brucella* strain. In one embodiment, the attenuated, recombinant *Brucella* strain is 1330ΔctpA. Further, the *Brucella* species may be *Brucella abortus, Brucella suis, Brucella melitensis, Brucella neotomae, Brucella canis*, or *Brucella ovis*, and the mammal may be humans, swine, cattle or reindeer.

The invention further provides a gene having a nucleotide sequence selected from SEQ ID NO: 1, SEQ ID NO: 3 and SEQ ID NO: 4.

The invention also provides a method of detecting exposure of a mammal to *Brucella* species. The method comprises the steps of obtaining a biological sample from the mammal, and amplifying nucleic acid in the biological sample by polymerase chain reaction using primers specific for SEQ ID NO: 1 or SEQ ID NO: 3.

In another preferred embodiment, the invention provides an attenuated, recombinant *Brucella* strain with a deficiency in tail-specific protease (TspA) (a homologue of carboxyl-terminal processing protease) activity, and the deficiency is caused by a deletion in the TspA gene of *Brucella melitensis*. (TspA is a homologue of CtpA.) In one embodiment of the invention, and the attenuated, recombinant *Brucella* is 16MΔtspA The invention further provides a method for eliciting an immune response to a *Brucella* species in a mammal, or for treating or preventing Brucellosis in a mammal, including vaccinating a mammal against Brucellosis. The method comprises the step of administering to the mammal in a quantity sufficient to elicit an immune response, an attenuated, recombinant *Brucella* strain with a deficiency in tail specific protease activity, in which the *Brucella* strain is *Brucella melitensis*, and the deficiency is caused by a deletion in TspA. In one embodiment of the method, the attenuated, recombinant *Brucella* strain is 16MΔtspA, and the mammal is of a type selected from the group consisting of humans, sheep, goats, dogs, swine, cattle and reindeer.

The invention further provides a composition for eliciting an immune response to *Brucella* species in a mammal. The composition comprises an attenuated, recombinant *Brucella* strain with a deficiency in tail-specific protease (TspA) (a homologue of carboxyl-terminal processing protease) activity, in which the attenuated, recombinant *Brucella* strain is of the species *Brucella melitensis* and the is caused by a deletion in TspA. The composition further includes a physiologically suitable carrier. In one embodiment, the attenuated, recombinant *Brucella* strain is 16MδtspA.

The invention further provides a gene having a nucleotide sequence selected from SEQ ID NO: 7, SEQ ID NO: 9 and SEQ ID NO: 11.

The invention further provides a method of detecting exposure of a mammal to *Brucella* species. The method comprises the steps of 1) obtaining a biological sample from a mammal, and 2) amplifying nucleic acid in the biological sample by polymerase chain reaction using primers specific for SEQ ID NO: 7 or SEQ ID NO: 9.

BRIEF DESCRIPTION OF THE DRAWINGS

FIG. 1. Nucleotide (SEQ ID NO: 1) and amino acid (SEQ ID NO: 2) sequences of CtpA gene of *Brucella suis*.

FIG. 2. Sequence of the 471 nucleotides that were deleted from CtpA (SEQ ID NO: 3).

FIG. 3. Nucleotide sequence of 1330ΔctpA (SEQ ID NO: 4).

FIG. 5A: Growth of strains in regular LB media.

FIGS. 12A and B. A, Nucleotide sequence encoding *Brucella melitensis* TspA (SEQ ID NO: 7); B, amino acid sequence of *Brucella melitensis* TspA (SEQ ID NO: 8).

FIG. 13. Protein sequence comparison for *Brucella melitensis* TspA and other proteins. The deduced amino acid sequences of parts of the CtpA proteins and periplasmic proteins of *A. tumefaciens* (Agrobac) (GenBank accession no. NP_355704.1; SEQ ID NO: 14), *Bartonella quintana* (Bartone) (GenBank accession no. Q44879; SEQ ID NO: 15), *Bradyrhizobium japonicum* (Bradyrh) (GenBank accession no. NP_771462.1; SEQ ID NO: 16), *Brucella melitensis* (Brucell) (GenBank accession no.NP_539132.1; SEQ ID NO: 17), *Mesorhizobium loti* (Mesorhi) (GenBank accession no NP_104979.1; SEQ ID NO: 18), *Rhodopseudomonas palustris* (Rhodops) (GenBank accession no. ZP_00009772.1; SEQ ID NO: 19), and *Sinorhizobium meliloti* (Sinorhi) (GenBank accession no. NP_387272.1; SEQ ID NO: 20) were compared. The ClustalV (PAM250) program of DNASTAR was used to align the sequences. The numbers on the left are the positions of the amino acid residues in the proteins. The shaded amino acids are identical in all proteins. Amino acids shown to be essential for enzymatic activity in *Synechocystis* sp. Strain PCC 6803 and *B. burgdorferi* strain B31 are indicated by solid circles.

FIGS. 14A, B and C.A, Nucleotide sequence encoding *Brucella melitensis* deletion mutant 16MΔtspA; (SEQ ID NO: 9) B, amino acid sequence of *Brucella melitensis* deletion mutant 16MΔtspA (SEQ ID NO: 10); C, nucleotide sequence that was deleted from the tspA gene (SEQ ID NO: 11).

DETAILED DESCRIPTION OF THE PREFERRED EMBODIMENTS OF THE INVENTION

Figure 4:
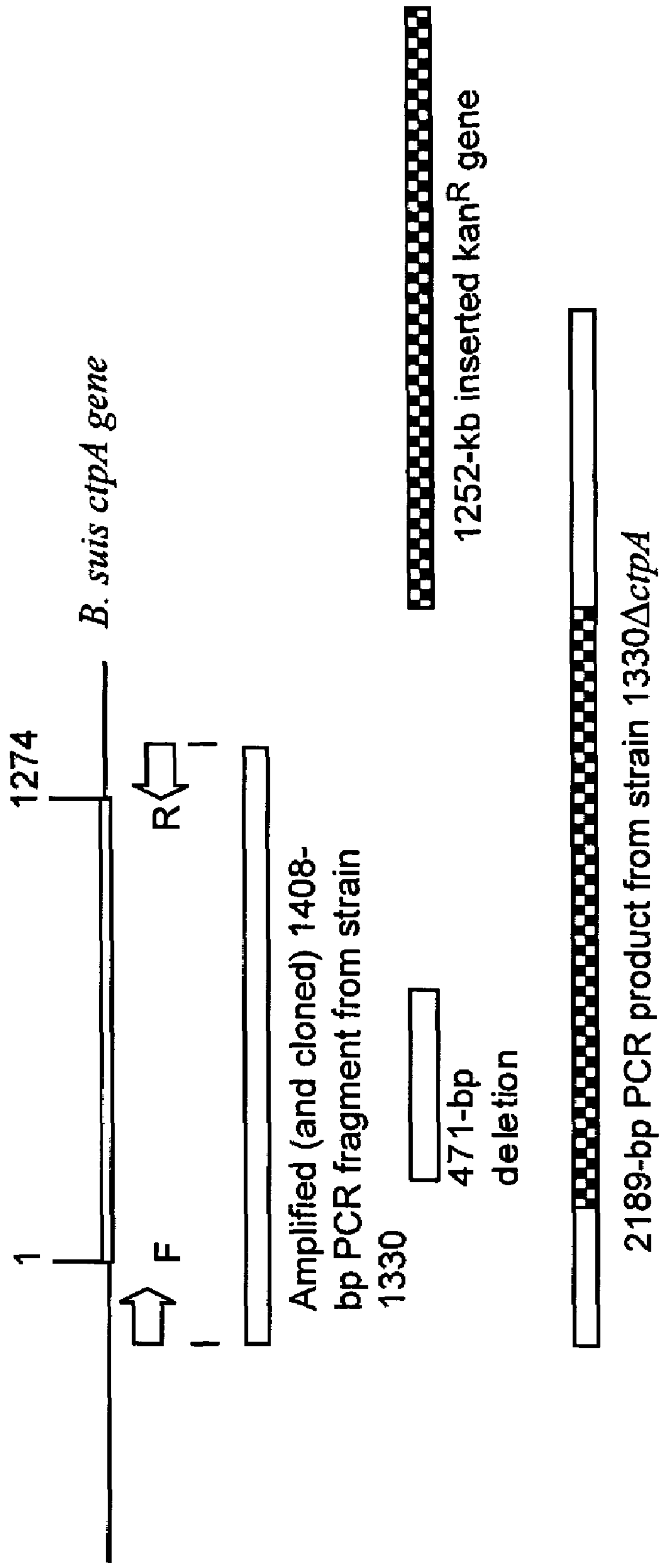
FIG. 4. Physical map of the insert of pGEMΔctpAK suicide vector. Solid line indicates the length and location of the ctpA gene. Solid-unfilled arrows indicate the locations of primers used to PCR amplify a portion of the ctpA gene. Solid-fill block indicates the gene fragment amplified by PCR. Dotted rectangle indicates the region deleted by mutagenesis. The checked solid block indicates the inserted $kan^r$ gene.

The present invention provides compositions and methods for preventing or treating Brucellosis in mammals. The compositions elicit an immune response against virulent, pathogenic *Brucella* species, and thus may be used as vaccines. The compositions comprise at least one attenuated recombinant *Brucella* bacterial strain in which there is a deficiency in carboxyl-terminal protease (CtpA) activity. CtpA activity may be encoded by a ctpA gene (as in *Brucella suis*). Alternatively, CtpA activity may be encoded by a homologue with carboxyl-terminal protease activity designated as tail-specific protease (such as the tspA gene of *Brucella melitensis*). By "deficiency" we mean that CtpA activity is partially or totally absent in the bacterium. For example, the gene encoding CtpA activity may be partially or totally deleted from the *Brucella* bacteria, e.g. by genetic engineering techniques as described herein. Due to the use of such genetic engineering techniques, the genetic makeup of the attenuated strain is fully known, an advantage for a vaccine composition. Alternatively, the gene encoding CtpA (e.g. CtpA or TspA) may be altered in some other manner that inactivates the gene, or greatly reduces its activity, e.g. by the introduction of mutations within the gene by genetic engineering, thereby reducing or eliminating the function of the gene and/or of the CtpA protein encoded by the gene, by preventing transcription or translation of the gene, etc. In any case, whether by deletion or by some other mutation, the result is that CtpA activity within the *Brucella* bacteria is modified so as to be non-existent or greatly reduced. By "greatly reduced" we mean that the modification results in a reduction in activity (compared to CtpA activity in wild type cells) of at least about 50-100%, preferably about 75-100%, and most preferably from about 90-100%. This reduction in CtpA activity may be due, for example, to mutations that are introduced into the CtpA gene to cause a severe reduction in the amount of CtpA that is produced in the cell, or to cause the form of CtpA that is produced by the mutated gene to be greatly reduced in activity or to be non-active. Those of skill in the art are well acquainted with procedures for assaying the level of activity of CtpA in *Brucella* bacteria, and methods for the comparison of levels of enzyme activity between wild type and attenuated bacteria are also known (see, for example, methods described in the Examples section herein). Enzyme activity may be measured directly, or may be inferred by measurement of some other observable trait, e.g. growth rate, sensitivity to temperature, medium conditions, etc., or by a combination of both. Further, genetic changes in the bacteria may be detected/confirmed by techniques familiar to those of skill in genetic analyses, as also described herein (e.g. polymerase chain reaction (PCR) of bacterial genetic material with suitable primers).

*Brucella* strains that display such a deficiency in CtpA activity are "attenuated", that is the bacteria that are used in the composition are living and able to reproduce but compared with the infectious strains, they are less capable of surviving in animal or human hosts, and incapable or less capable of causing disease in hosts. The level of attenuation of a strain is determined using mouse experimental models. In this work, mice are injected with the strains, and at different time intervals (1, 3, 5, 7 and 9 weeks after injection), injected mice are sacrificed, their spleens are isolated and crushed, spleen content is plated on growth media plates, and incubated for 3-5 days at 37° C. at the presence of carbon-dioxide. Each cell of *Brucella* present in a spleen is expected to form a colony (colony forming unit or CFU) on plates after 3-5 days of incubation. If the injected strain is attenuated, its presence in the spleen never increases, but gradually declines with time and eventually disappears completely from the spleen. If the presence of a strain in spleen declines to about 100-600 CFU in 5-7 weeks, and disappears completely in 6-9 weeks after injection, it can be considered sufficiently attenuated or safe to be a vaccine. On the contrary, if a strain is infectious (virulent), its presence in spleens increases to about 1,000,000 CFU one week after injection and remains at a constant level of approximately 3000 CFU for more than 9 weeks after injection. Those of skill in the art are acquainted with procedures for growing attenuated *Brucella* species for the production of compositions for use as vaccines, for example, those that are outlined in the Examples section that is included herein.

The *Brucella* species or strain that is modified for use in the practice of the present invention (i.e. the species or strain which is genetically manipulated to produce or derive the recombinant, attenuated *Brucella* bacteria) may be any suitable *Brucella* species or strain. Examples include but are not limited to *Brucella abortus, Brucella canis, Brucella melitensis, Brucella neotomae* and *Brucella ovis, Brucella suis*, and various strains thereof. In a preferred embodiment of the invention, the attenuated *Brucella* bacteria are derived from *Brucella suis*. In addition, in one embodiment of the invention, the recombinant, attenuated *Brucella suis* has a deletion in the CtpA gene. In a preferred embodiment of the invention, the attenuated *Brucella suis* strain is recombinant strain1330ΔctpA. 1330ΔctpA is derived from *Brucella suis* and has a 471 base pair deletion in the ctpA gene. The nucleotide sequence of the ctpA gene (SEQ ID NO: 1) and the corresponding amino acid sequence (SEQ ID NO: 2) are given in FIG. 1. FIG. 2 depicts the 471 basepairs that are deleted and FIG. 3 (SEQ ID NO: 3) shows the nucleotide sequence of the CtpA gene after deletion of the 471 base pairs (SEQ ID NO: 4). However, those of skill in the art will recognize that it is not necessary to delete precisely this 471 basepair segment of the gene in order to generate an attenuated *Brucella* strain for use in the practice of the present invention. For example, more of the gene (e.g. up to 100% of the nucleotide sequences encoding the CtpA gene) may be deleted. Thus, in one embodiment, at least the indicated 471 base pair region is deleted. Alternatively, somewhat less extensive deletions may be employed, or deletions in other regions of the gene may be made, or deletions that overlap the 471 base pair region may be made, so long as the resulting *Brucella* bacteria are attenuated and can be used to elicit an immune response against at least one virulent *Brucella* species, and preferably provide protection against infection by a virulent *Brucella* species, in at least one mammal of interest.

In another preferred embodiment, the *Brucella* species is *Brucella melitensis* and the gene that encodes carboxy-terminal processing activity (also known as tail-specific protease activity) is the tspA gene, a homologue of the ctpA gene in *Brucella suis*. A preferred example of this embodiment is the case in which 471-base pair region is deleted from the tspA gene, to form the attenuated *Brucella melitensis* strain 16MΔtspA. The nucleotidesequence of TspA from *Brucella melitensis* (SEQ ID NO:7) is given in FIG. 12A, and the amino acid sequence (SEQ ID NO: 8) is given in FIG. 12B. The deleted forms of TspA present in the attenuated *Brucella melitensis* 16MΔtspA are depicted in FIG. 13A (nucleotide, SEQ ID NO: 9) and B (amino acid, SEQ ID NO: 10), as is the deleted nucleotide sequence (SEQ ID NO: 11, FIG. 13C).

In some embodiments, a suitable section (or all) of the ctpA gene is deleted from the *Brucella* chromosome. Alternatively, a suitable section of the ctpA gene may be replaced by a different nucleotide sequence, e.g. by a sequence which facilitates selection of deletions mutants such as an antibiotic resistance gene, or a non-antibiotic selection marker such as sacB or leuB. Techniques for performing such replacements are known, and include the technique of allelic exchange, as utilized and described herein.

In the practice of this invention, it is desirable to either delete or otherwise disable (gene replacement, etc.) the CtpA sequence in a *Brucella* strain such that antibody titer to the strain can be raised but where the attenuated strain is deficient in CtpA activity.

The invention further provides the genetic sequence of the ctpA gene of *Brucella suis*, as depicted in FIG. 1, as well as some exemplary sequences of a gene with a deletion. These sequences might be used for transfecting an organism to incorporate a gene encoding CtpA, as a probe to identify organisms which harbor genes encoding CtpA, as well as to identify related genes in other species based on homology and other factors, as well as for other applications. The ctpA gene may also find application for use in combination with other genes of interest where carboxyl terminal protease activity is desired. Furthermore, the transfected proteins from these sequences may have similar applications.

Those of skill in the art will recognize that many variants of the sequence may exist or be constructed which would also function in the practice of the present invention. For example, with respect to amino acid sequences, variants may exist or be constructed which display: conservative amino acid substitutions; non-conservative amino acid substitutions; truncation by, for example, deletion of amino acids at the amino or carboxy terminus, or internally within the molecule; or by addition of amino acids at the amino or carboxy terminus, or internally within the molecule (e.g. the addition of a histidine tag for purposes of facilitating protein isolation, the substitution of residues to alter solubility properties, the replacement of residues which comprise protease cleavage sites to eliminate cleavage and increase stability, the addition or elimination of glycosylation sites, and the like, or for any other reason). Such variants may be naturally occurring (e.g. as a result of natural variations between species or between individuals); or they may be purposefully introduced (e.g. in a laboratory setting using genetic engineering techniques). All such variants of the sequences disclosed herein are intended to be encompassed by the teaching of the present invention, provided the sequence displays sufficient identity to the described sequences. Preferably, identity will be in the range of about 50 to 100%, and more preferably in the range of about 75 to 100%, and most preferably in the range of about 80 to 100% of the disclosed sequences. The identity is with reference to the portion of the amino acid sequence that corresponds to the original antigen sequence, i.e. not including additional elements that might be added, such as those described below for chimeric antigens. Further, all sequences which hybridize to the depicted sequence under stringent hybridization conditions are also encompassed.

The present invention provides compositions for use in eliciting an immune response, and which may be utilized as a vaccine against Brucellosis. By "eliciting an immune response" we mean that the composition stimulates synthesis of specific antibodies against the attenuated, recombinant *Brucella* strain at a titer of from about 1 to about $5\times10^6$ or greater. In some embodiments, the titer is at least in the range of about 100 to about 1000 (or more), as measured by techniques that are known to those of skill in the art, for example, by $^3$H thymidine incorporation or by Enzyme Linked Immunosorbent Assay (ELISA). In a preferred embodiment, the titer is measured by ELISA and the antibody titer is about $3.4\times10^2$ to about $4.3\times10^2$. Further, the antibodies that are produced cross-react with at least one other pathogenic, virulent *Brucella* species or strain, against which it is desired to raise an immune response.

The compositions of the present invention include substantially purified attenuated, recombinant *Brucella* bacteria with a deficiency in CtpA activity, and a pharmacologically suitable carrier. The preparation of such compositions for use as vaccines is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients that are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. In addition, the composition may contain other adjuvants. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of active ingredient (i.e. the attenuated *Brucella* strain) in the formulations may vary. However, in general, the amount will be from about 1-99% of the total composition. The vaccine preparations of the present invention may further comprise an adjuvant, suitable examples of which include but are not limited to Seppic, Quil A, Alhydrogel, etc.

The present invention provides not only compositions, but also methods for their use to elicit an immune response. By "elicit an immune response", we mean that administration of the composition causes the synthesis of specific antibodies at a titer in the range of from about 1 to about $1\times10^6$ or greater. Preferably, the titer is from about 10,000 to about $1\times10^6$ or more, and most preferably, the titer is greater than $1\times10^6$ as measured, e.g. by $^3$H thymidine incorporation. The methods involve administering a composition comprising attenuated *Brucella* strains with a deficiency in CtpA activity in a pharmacologically acceptable carrier to a mammal. The vaccine preparations of the present invention may be administered by any of the many suitable means which are well known to those of skill in the art, including but not limited to by injection (e.g. subcutaneous or intramuscular), orally, intranasally, by ingestion of a food product containing the antigen, etc. In preferred embodiments, the mode of administration is subcutaneous or intramuscular.

The methods of the present invention are directed to eliciting an immune response in a mammal. In some embodiments, the mammal is an animal such as sheep, goats, dogs, swine, reindeer, and cattle (either domestic or feral). In another embodiment of the invention, the mammal is a human. Where the disease of Brucellosis is involved, those of skill in the art will recognize that many strains of *Brucella* infect more than one species of mammal. Thus, a composition for vaccinating mammals against *Brucella* need not be specific for the species being vaccinated so much as efficacious against particular *Brucella* strains, since a strain can infect several species. The compositions of the present invention may be used to vaccinate mammals of any species, so long as they are infected with or are at risk for being infected with a strain or species of *Brucella* to which the immune response elicited by the compositions is relevant, i.e. in which the immune response elicited by the compositions is effective against treating or preventing disease symptoms that would otherwise be caused by the *Brucella* strain/species. Those of skill in the art are well versed in procedures for determining the efficacy of a composition to elicit an immune response to *Brucella* bacteria, for example, those that are discussed in the Examples section herein. In general, in order for a composition to be considered effective as a vaccine, the following criteria are used:

(1) Attenuated (as described above)

(2) Induce immune responses (as described above)

(3) Induce protection in animals against infection (challenge) with the pathogenic (virulent) strain of *Brucella*—in determining this aspect, groups of mice are injected (vaccinated) intraperitoneally with either saline, or the vaccine strain (i.e. strain 1330ΔctpA). About eight weeks after vaccination, all mice are injected (challenged) intraperitoneally with pathogenic (virulent) strains of *Brucella* (i.e., *B. abortus* strain 2308, *B. melitensis* strain 16M, or *B. suis* strain 1330). Two weeks after challenge, mice are sacrificed, and the presence of pathogenic *Brucella* in spleens will be determined, as described previously. In mice injected with saline, immune responses are not developed and therefore, the challenged virulent *Brucella* strains (2308, 16M or 1330) are expected to retain and multiply. Therefore, from spleens of those mice (injected with saline) 100,000 to 1000,000 or more CFU of challenged *Brucella* can be recovered. On the contrary, of those mice injected with the vaccine strain, immune responses are expected to develop, and as a result, most of the challenged *Brucella* are expected to be lysed (destroyed). From spleens of these mice (injected with vaccine) 0 to 600 CFU of challenged *Brucella* can be recovered. In a preferred embodiment of the invention, the composition is active in eliciting an immune response against *Brucella* species that include but are not limited to *Brucella abortus, Brucella suis, Brucella melitensis*, and *Brucella ovis*.

In addition, the compositions of the present invention may be used either prophylactically to prevent a mammal from contracting Brucellosis, or after the fact to treat a known (or suspected) infection in order to ameliorate symptoms of the disease.

The invention also provides two methods of detecting *Brucella* infection. In particular, the method is useful for differentiating infectious, virulent field strains of *Brucella* from the attenuated recombinant strains of the present invention. The first method involves obtaining a suitable biological sample from a mammal (e.g. mice, swine or cattle), and carrying out polymerase chain reaction (PCR) on the sample using primers that specifically amplify the ctpA gene. By amplifying the ctpA gene of FIG. 1, *Brucella* infection or previous *Brucella* exposure (e.g. by vaccination or otherwise) may be identified. If the PCR using the biological sample amplifies a 1408 basepair size fragment, it can be concluded that the respective animal has been infected with a field isolate of *Brucella*. If the PCR amplifies a 2189 basepair size fragment, it is an indication that the respective animal has been vaccinated with the invented strain 1330ΔctpA. The second method involves obtaining a suitable biological sample from a mammal (e.g. mouse, swine or cattle), isolating the bacterium from the sample, and growing it in growth media with or without salt. If the isolated strain grows in both media (with salt or without salt), it is an indication that the respective animal has been infected with a field isolate of *Brucella*. If the isolated bacterium grows in media that contains salt but does not grow in media that does not contain salt, it indicates that the respective animal has been vaccinated with the invented strain 1330ΔctpA.

EXAMPLES

Example 1

Animal brucellosis is a disease affecting various domestic and wild life species, resulting from infection with bacteria belonging to the genus *Brucella* (Corbel and Brinley Morgan, 1984). Brucellosis is a zoonotic disease and human infection is normally acquired either through consumption of contaminated dairy and meat products or by contact with infected animal secretions (Acha and Szyfres, 1980). *Brucella* species are facultative intracellular pathogens that enter the host via mucosal surfaces and are able to survive inside macrophages. The primary strategy for survival in macrophages appears to be inhibition of phagosome-lysosome fusion (Arenas et al., 2000; Baldwin and Winter, 1994; Naroeni et al., 2001). Localization and survival within autophagosome-like compartments associated with the rough endoplasmic reticulum has also been demonstrated in placental trophoblasts and other non-professional phagocytes (Anderson et al., 1986; Pizarro-Cerda et al., 1998). Molecular characterization of this survival process is important because it would provide additional guidance for the development of measures for prevention and control of *Brucella* and perhaps other intracellular pathogens. As the result of annotating the *B. suis* genome (Paulsen et al., 2002), putative virulence genes in *B. suis* are being identified by looking for virulence homologs that have been reported in other pathogens.

It is well known that many proteins destined for extracytoplasmic locations are initially synthesized as precursor forms and processed into mature forms by proteolytic cleavage to remove short peptide sequences, either near the amino terminus or near the carboxyl terminus of such proteins. The endoproteases responsible for cleaving of amino-terminal peptides are called amino-terminal processing proteases and have been identified and studied in a number of systems. During recent years, a relatively new class of endoproteases with carboxyl-terminal processing activities has been described in various bacteria and organellar systems including cyanobacteria, chloroplasts, and *E. coli* (Keiler and Sauer, 1998; Pakrasi, 1998; Satoh, 1998; Silber et al., 1992; Keiler, et al., 1996). These carboxyl-terminal proteases (Ctp) from cyanobacteria, *E. coli* and green plants share significant sequence similarities (Inagaki et al., 1996; Oelmüller et al., 1996). However, none of them exhibits sequence homology with other protease classes with well-defined mechanisms of action. Ctps are serine proteases that utilize a Ser/Lys catalytic dyad instead of the well-known Ser/His/Asp catalytic triad (Paetzel and Dalbey, 1997).

The enzymes involved in synthesis of the bacterial cell wall are named as penicillin binding proteins (PBPs). This name has been given to these enzymes because b-Lactam antibiotics, including penicillin, bind covalently and irreversibly to these enzymes and inhibit the synthesis of the peptidoglycan layer (Waxman and Strominger, 1983). In *E. coli*, eight PBPs have been identified. Among them, PBP 3 is believed to be involved in polar cap murein synthesis/cell division (Yousif et al., 1985). In *E. coli*, the bulk of the PBP 3 molecule, except for the N-terminal membrane anchor region, protrudes into the periplasmic space, where it acts on murein (Bowler and Spratt, 1989). Amino acid sequence analysis of precursor and mature forms of PBP 3 (Nagasawa et al., 1989) revealed that cleavage of eleven C-terminal residues is responsible for the maturation of PBP 3 protein. The C-terminal protease Prc has been identified as responsible for cleavage of the C-terminal 11 amino acid residues from the PBP 3 precursor. The Prc protein resides on the outer side of the cytoplasmic membrane (Hara et al., 1991). The *E. coli* mutant JE7304, developed by Hara et al., (1989) by deleting the prc gene encoding Prc protein was defective in the C-terminal processing of PBP 3. This mutant showed thermo-sensitive growth on a salt-free L-agar plate, suggesting that the prc gene is involved in some essential cellular process, which may or may not be related to the cell division function of PBP 3 (Hara et al., 1991). The prc function thus seemed to be involved in protection of the cell from thermal and osmotic stresses. Loss of Prc function also resulted in leakage of periplasmic proteins including RNase I and alkaline phosphatase (Hara et al., 1991). The leaky phenotype of the prc mutant has been attributed to the impairment of the structural integrity of the outer membrane, which could lead to sensitivity to osmotic stress (Hara et al., 1991).

The ctpA gene is 1274-bp long and is located between 1768433 and 1769707-bp on chromosome I of the *B. suis* genome. The predicted molecular mass of CtpA is 45.2-kDa. The protein encoded by this gene shares 31% homology with Prc protein of *E. coli* and up to 77% homology with the Ctps of other bacteria. Based on this homology, it was hypothesized that the protein encoded by ctpA was a C-terminal protease that could play a significant role in determining the virulence of *B. suis*. It is herein reported that a *B. suis* strain with a defective ctpA gene exhibits salt-sensitive growth exactly as the Prc-deficient *E. coli* did. In addition, this strain produces smaller colonies on enriched agar plates, and exhibits slow growth in enriched growth media and reduced persistence in mice and mouse macrophages.

Materials and Methods

Bacterial strains, plasmids, and reagents. *B. abortus* strain 2308, *B. melitensis* strain 16M, and *B. suis* strains 1330 and VTRS1 were obtained from our culture collection. *E. coli* strain Top10 (Invitrogen Life Technologies, Carlsbad, Calif.) was used for producing plasmid constructs. *E. coli* Prc mutant strain JE7929 was a gift. *E. coli* were grown in Luria Bertani (LB) broth or on LB agar (Difco Laboratories, Sparks, Md.). Brucellae were grown in LB broth with or without sodium chloride at 30, 37 or 42° C. to determine whether growth was osmo-sensitive and/or thermo-sensitive. For all other assays, Brucellae were grown either in trypticase soy broth (TSB) or on trypticase soy agar (TSA) plates (Difco) at 37° C. as previously described (Schurig et al., 1991). The plasmids used in this study are listed in Table 1. Bacteria containing plasmids were grown in the presence of ampicillin or kanamycin at 100-μg/ml concentration (Table 1).

All experiments with live Brucellae were performed in a Biosafety Level 3 facility at the Infectious Disease Unit of the Virginia-Maryland Regional College of Veterinary Medicine.

TABLE 1

Description of the plasmids and bacterial strains used in this study

| Name | Description | Source or reference |
|---|---|---|
| Plasmids | | |
| pCR2.1 | TA cloning vector, 3.9-kb; $Amp^r$ | Invitrogen |
| pCRctpA | pCR2.1 with 1.4-kb insert containing the *B. suis* ctpA gene; $Amp^r$ | This study |
| pGEM-3Z | Cloning vector, 2.74-kb, $Amp^r$ | Promega |
| pGMEctpA | pGEM-3Z with a 1.4-kb insert containing the *B. suis* ctpA gene from pCRctpA; $Amp^r$ | This study |
| pUC4K | Cloning vector, 3.9-kb, $Kan^r$, $Amp^r$ | |
| pGEMctpAK | PGEMctp with 0.5-kb BclI fragment deleted and blunt ended and a 1.3-kb SalI-cut and blunt-ended $Kan^r$ cassette from pUC4K ligated, $Kan^r$, $Amp^r$ | This study |
| pBBR4MCS | Broad-host range vector; $Cm^r$ | Kovach et al., 1994 |
| pBBctpA | pBBR4MCS with a 1.4-kb insert containing the *B. suis* ctpA gene from pCRctpA; $Amp^r$ | This study |
| Bacteria | | |
| *Escherichia coli* | | |
| Top 10 | F-mcrAΔ(mrr-hsdRMS-mcrBC) Φ80lacZΔM15ΔlacX74deoR recA1araD139Δ(ara-leu)7697 galUgalKrpsL (StrR) endA1 nupG | Invitrogen |
| JE7929 | Prc mutant | Fraipont et al., 1994 |
| *B. abortus* 2308 | Wild-type, smooth strain | G. G. Schurig |
| *B. melitensis* 16M | Wild-type, smooth strain | G. G. Schurig |
| *B. suis* 1330 | Wild-type, smooth strain | G. G. Schurig |
| 1330ΔctpA | ctpA deleted mutant of 1330, $Kan^r$ | This study |
| 1330ΔctpA[pBBctpA] | Strain 1330 containing pBBctpA, $Kan^r$, $Amp^r$ | This study |
| VTRS1 | wboA deletion mutant of *B. suis* | Winter (1996) |

Recombinant DNA methods. Genomic DNA was isolated from *B. suis* strain 1330 using a Qiagen Blood and tissue DNA kit (Qiagen Inc., Valencia, Calif.). Plasmid DNA was isolated using plasmid mini or midi prep purification kits (Qiagen). Restriction digests, Klenow reactions, and ligations of DNA were performed as described elsewhere (Sambrook et al., 2001). Restriction enzymes, Klenow fragment and T4 DNA ligase enzyme were purchased from Promega Corporation (Madison, Wis.). Ligated plasmid DNA was transferred to *E. coli* Top10 cells by heat shock transformation, as per manufacturer's guidelines (Invitrogen). Purified plasmid DNA was electroporated into *B. suis* with a BTX ECM-600 electroporator (BTX, San Diego, Calif.), as described previously (McQuiston et al., 1995).

DNA sequence analysis. The nucleotide sequence of ctpA gene was analyzed with DNASTAR software (DNASTAR, Inc., Madison, Wis.). Sequence similarity searches of the EMBL/GenBank/DDBJ databases were performed using BLAST software (Altschul et al., 1990) at the National Center for Biotechnology Information (Bethesda, Md.).

Mutation of the *B. suis* ctpA gene by allelic exchange. A 1408-bp region including a major portion of the ctpA gene was amplified via PCR using the genomic DNA of *B. suis* (FIG. 4). A primer pair consisting of a forward primer (5 ' GGGGTACCGTGGTGGACTGA 3 ') (SEQ ID NO: 5) and a reverse primer (5 ' GGCTGCAGTC-CCGCGTTTTTGTCTT 3 ') (SEQ ID NO: 6) (Ransom Hill Bioscience, Inc., Ramona, Calif) were designed based on the nucleotide sequence (GenBank accession no. NC_004310). The *B. suis* genomic sequence 89 to 78-bp upstream from ATG starting codon of ctpA gene was used to design the forward primer, whereas the sequence 14 to 37-bp downstream from the stop codon of ctpA was used to design the reverse primer (FIG. 4). A restriction site was engineered into each primer (KpnI in the forward primer, and PstI in the reverse primer, shown in bold case in the primer sequences). PCR amplification was performed in an Omni Gene thermocycler (Hybaid, Franklin, Mass.) at 95° C. for 5 min, followed by 35 cycles that each included 1 min of denaturation at 95° C., 1 min of annealing at 59.7° C., and 3 min of extension at 72° C. The amplified gene fragment was cloned into the pCR2.1 vector of the TA cloning system (Invitrogen) to produce plasmid pCRctpA. Competent *E. coli* Top10 cells (Invitrogen) were transformed with the ligation mixture, and the colonies carrying the recombinant plasmid were picked from TSA plates containing ampicillin (100 µg/ml), as per the manufacturer's guidelines. From this plasmid, the ctpA gene was isolated by KpnI and PstI digestion and cloned into the same sites of plasmid pGEM-3Z (Promega). The resulting 4.2-kb plasmid was designated as pGEMctpA. Competent *E. coli* Top10 cells (Invitrogen) were transformed with the ligation mixture, and the colonies carrying the recombinant plasmid were picked from TSA plates containing ampicillin (100 µg/ml). The suicide vector pGEMctpAK was constructed as follows: the plasmid pGEMctpA was digested with BclI to delete a 471-bp region from ctpA gene. The BclI sites on the 3.7-kb plasmid were filled in by reaction with Klenow enzyme and ligated to the 1.3-kb SalI fragment of pUC4K (also blunt ended) containing the Tn903 npt gene (Ried and Colmer, 1987), which confers kanamycin resistance ($Kan^R$) to *B. suis*. The resulting suicide vector was designated pGEMctpAK. Competent *E. coli* Top10 cells (Invitrogen) were transformed with the ligation mixture, and the colonies carrying the recombinant plasmid were picked from TSA plates containing kanamycin (100 μg/ml).

One microgram of pGEMctpAK was used to electroporate *B. suis* strain 1330; several colonies of strain 1330 were obtained from a TSA plate containing kanamycin (100 μg/ml). These colonies were streaked on TSA plate containing ampicillin (100 μg/ml) to determine if a single- or double-crossover event had occurred. Three of the colonies did not grow on ampicillin containing plates suggesting that a double cross-over event had occurred, whereas the rest of the colonies grew on ampicillin containing plates suggesting that a single cross-over event had occurred. PCR with the primers used for amplifying the ctpA gene (as described above) confirmed that a double-crossover event had taken place in all three transformants. Cells were harvested from *B. suis* strains, boiled for 30 min, and centrifuged for 15 min. The supernatant was used for PCR using the forward and the reverse primers (FIG. 4). Strain 1330 amplified a 1408-bp fragment whereas strain 1330ΔctpA amplified a 2189-bp fragment. (data not shown). One of these strains was chosen for further analyses and designated 1330ΔctpA.

Complementation of ctpA gene activity in mutant 1330ΔctpA. The 1.4-kb DNA fragment containing *B. suis* ctpA gene was isolated by SacI and XbaI digestion of plasmid pCRctpA and was cloned into same sites of broad-host range vector pBBR4MCS (Kovach et al., 1994). The resulting plasmid was designated as pBBctpA. One microgram of pBBctpA was used to electroporate *B. suis* strain 1330ΔctpA; several colonies of strain 1330ΔctpA were picked from a TSA plate containing ampicillin (100 μg/ml). Six of the colonies were tested for growth in salt-free LB media (details below). One of the colonies that grew well in this media was chosen for further analyses and designated as 1330ΔctpA[pBBctpA].

Complementation of prc gene activity in Prc-deficient *E. coli.* One microgram of pBBctpA was used to electroporate the Prc mutant *E. coli* strain JE7929; several colonies of strain JE7929 were picked from a TSA plate containing ampicillin (100 μg/ml). Ten of the colonies were tested for growth in salt-free LB media (details to follow).

Growth rates of *B. suis* strains in regular or salt-free media at different temperatures. Salt-free LB media was prepared by mixing bactotryptone and yeast in water per manufacturer's instruction (Difco), but omitting sodium chloride. Single colonies of strains 1330, 1330ΔctpA, and 1330ΔctpA [pBBctpA] were grown at 37° C. for 24 hours to stationary phase in 10 ml of TSB. The cells were pelleted in two equal aliquots by centrifugation. One pellet was resuspended in 1 ml of regular LB broth and used to inoculate 25 ml of regular LB broth in a Klett side-arm flask to 12 to 16 Klett units. The other pellet was resuspended in salt-free LB media and used to inoculate 25 ml of salt-free LB broth in a Klett flask to 8 to 16 Klett units. Cultures were grown at 30, 37, or 42° C. at 180 rpm; Klett readings were recorded every two hours in a Klett Sumerson photometer.

Acid precipitation and denaturing gel electrophoresis of secreted proteins. Strains 1330, 1330ΔctpA and 1330ΔctpA [pBBctpA] were grown in 25 ml LB broth to stationary phase (to 339, 179 and 288 Klett units, respectively). The culture was centrifuged at 2000×G for 15 min, and the cell free culture medium was collected. Trichloroacetic acid (TCA) was added to the medium at 5% of final volume and incubated at 4° C. overnight. The acidified medium was centrifuged at 10000×g for 15 min to collect the protein precipitate. The insoluble material was resuspended in Laemmli sample buffer (Sigma Chemical Co., St. Louis, Mo.), boiled for 20 min and electrophoresed on 10% SDS/PAGE gels according to standard procedures (Laemmli, 1970). Gels containing the separated proteins were either stained with Coomassie brilliant blue G (Sigma Chemical Co.) or used for Western blot analysis.

Western blotting. Western blotting was performed as previously described (Vemulapalli et al., 1998). Briefly, proteins separated by SDS-PAGE were transferred to a nitrocellulose membrane by using a Trans-blot semidry system (Bio-Rad Laboratories, Hercules, Calif.). The membranes were blocked with a solution of 1.5% non-fat milk powder plus 1.5% bovine serum albumin. For analysis of TCA insoluble proteins, the membranes were incubated with goat anti-heat killed *B. abortus* polyclonal serum (Goat-48) for 24 hours and subsequently developed with rabbit anti-goat IgG (whole molecule) conjugated with horseradish peroxidase (Sigma Chemical Co).

Phenotypic characterization of *B. suis* strains. Recombinant colonies were analyzed for their rough or smooth phenotype by crystal violet staining as described previously (Alton, et al., 1975; White and Wilson, 1951). Briefly, crystal violet staining solution was added to colonies grown on TSA plates. After two minutes, the solution was poured off and the colonies were observed to determine if they retained the stain (rough phenotype) or not (smooth phenotype).

Cell morphology *B. suis* strains. The wild type and the CtpA-deficient *B. suis* strains were grown in media with or without salt, and the cells were used for a Gram-staining. The stained specimens were observed using a light microscope at 100× magnification.

Preparation of *B. suis* inoculum stocks. TSA plates were inoculated with single colonies of *B. suis* strains. After four days of incubation at 37° C. in $CO_2$, the cells were scooped/harvested from plates, washed with PBS, resuspended in 20% glycerol, and saved at −80° C. The number of viable cells was determined after culturing dilutions of the cell suspensions on TSB.

Persistence of recombinant *B. suis* strains in J774 macrophages. J774 macrophage cells were seeded at a density of $5\times10^5$/ml in Dulbecco's modified essential medium (DMEM) (Sigma-Aldrich) into 24-well tissue culture dishes and cultured until confluent. The tissue culture medium was removed, 200 μl ($10^8$ cells) of the bacterial suspension in PBS was added, and the cells were incubated at 37° C. for four hours. The suspension above the cell monolayer was removed, and the cells were washed three times with PBS. One milliliter of DMEM containing 25 μg of gentamicin/ml was added, and the cells were incubated for 48 hours at 37° C. At various time points (0, 4, 24 and 48 hours of incubation), the growth medium was removed, the cells were washed with PBS, and 500 μl of 0.25% sodium deoxycholate was added to the cells, which were lysed by aspiration. After 5 minutes the lysate was diluted in PBS, and the number of viable cells was determined after growth at 37° C. for 72 h on TSA. Triplicate samples were taken at all time points, and the assay was repeated two times.

Survival of recombinant *B. suis* strains in mice. Six-week-old female BALB/c mice (Charles River Laboratories, Wilmington, Mass.) were allowed 1 week of acclimatization. Groups of 7 or 8 mice each were intraperitoneally injected with either $1\text{-}2\times10^5$ CFU of *B. suis* strains 1330, 1330ΔctpA, or VTRS1. Mice were sacrificed at 6 weeks after inoculation and the *Brucella* CFU per spleen determined as described previously (Schurig et al., 1991). Briefly, spleens were collected and homogenized in TSB. Serial dilutions of each spleen's homogenates were plated on TSA plates. The number of CFU that appeared on plates was determined after four days of incubation.

In order to determine the clearance of strains in different time intervals, groups of 25 mice were injected with $0.9\text{-}1.1\times10^4$ CFU of *B. suis* strains 1330 or 1330ΔctpA. Groups of five mice injected with each strain were sacrificed at 1, 3, 5, 7 and 9 weeks after inoculation and the *Brucella* CFU per spleen determined as described above.

ELISA. *B. suis* wild type strain 1330 cells were harvested and killed by boiling for 30 minutes, resuspended at 1:20 in carbonate buffer (pH 9.6) and used to coat the wells of polystyrene plates (100 μl/well; Nunc-Immuno plate with a MaxiSorp surface). After overnight incubation at 4° C., the plates were washed three times in wash buffer (Tris-buffered saline [TBS] at pH 7.4, 0.05% Tween 20) and the diluted mouse serum samples (1:100 dilution in PBS) were added to the wells (100 μl/well). Each serum sample was tested in duplicate wells. The plates were incubated for 2 h at room temperature and washed three times, and isotype-specific goat anti-mouse reagents (Sigma, St. Louis, Mo.) diluted at 1:1,000 in PBS were added to the wells (100 μl/well). After 30 min of incubation at room temperature, the plates were washed three times, and rabbit anti-goat IgG (Sigma) diluted at 1:5,000 in washing buffer (100 μl/well) was added. After 15 min of incubation at room temperature, the plates were washed three times, and 100 μl of substrate solution (TMB Microwell peroxidase substrate; Kirkegaard & Perry Laboratories, Gaithersburg, Md.) was added to each well. After 10 min of incubation at room temperature, the enzyme reaction was stopped by adding 100 μl of stop solution (0.185M sulfuric acid), and the $A_{450}$ was recorded with a microplate reader (Molecular Devices, Sunnyvale, Calif.).

Protective efficacy of *B. suis* mutant 1330ΔctpA. Six-week-old female BALB/c mice (The Jackson Laboratory, Bar Harbor, Me.) were allowed 1 week of acclimatization. Groups of 7 mice each were intraperitoneally injected with PBS, strain 1330ΔctpA or strain VTRS1. Two doses of strains 1330ΔctpA or VTRS1 were used in vaccination, i.e., a high dose, which was similar to the dose used in clearance study and the low dose, which was 1 $\log_{10}$ CFU lower than the above dose. Eight weeks post-inoculation, mice were intraperitoneally challenged with $4.8\times10^4$ CFU of wild type, virulent *B. suis* strain 1330. Two weeks post-challenge, mice were sacrificed and the *Brucella* CFU per spleen determined as described above.

In a separate trial, six-week-old female BALB/c mice (The Jackson Laboratory, Bar Harbor, Me.) were allowed 1 week of acclimatization. Ten of these mice were intraperitoneally injected with PBS, and another 12 mice were inoculated with $2.1\times10^5$ CFU of strain 1330ΔctpA. Six weeks post-inoculation, five mice injected with PBS and six mice inoculated with strain 1330ΔctpA were intraperitoneally challenged with $3.2\times10^3$ CFU of wild type, virulent *B. abortus* strain 2308. The other five mice injected with PBS and the six mice inoculated with strain 1330ΔctpA were challenged with $1.4\times10^5$ CFU of wild type, virulent *B. melitensis* strain 16M. Two weeks post-challenge, mice were sacrificed and the *Brucella* CFU per spleen determined as described above.

Data analyses. Results from the clearance study, ELISA and protection study were analyzed using the Microsoft Excel 2001 program (Microsoft Corporation).

Results

Nucleotide sequence of ctpA. At the amino acid level, ctpA gene shared 99% identity with the tail-specific protease of *B. melitensis*. Additionally, it showed up to 77% identity with carboxyl-terminal proteases of a number of bacterial species including *Bartonella Quintana, Mesorhizobium loti, Sinorhizobium meliloti* and, *Agrobacterium tumefaciens*, and up to 61% identity with a periplasmic protease of other bacteria including *Rhodopseudomonas palustris, Rhodobacter sphaeroides*, and *Magnetospirillum magnetotacticum* (Table 2).

TABLE 2

Amino acid level identity of *B. suis* Cxtp protein to the protein sequences in GenBank

| Bacterial species | Protein | Identity to *B. suis* CtpA (%) | GenBank Accession # |
|---|---|---|---|
| *B. melitensis* | Tail-specific proteinase | 99 | NP_539132.1 |
| *Mesorhizobium loti* | Carboxyl-terminal protease | 77 | NP_104979.1 |
| *Bartonella quintana* | Carboxyl-terminal protease | 72 | Q44879 |
| *Agrobacterium tumefaciens* | Carboxyl-terminal protease | 71 | NP_355704.1 |
| *Sinorhizobium meliloti* | Carboxyl-terminal protease | 71 | NP_387272.1 |
| *Bradyrhizobium japonicum* | Carboxyl-terminal protease | 59 | NP_771462.1 |
| *Pseudomonas* species | Carboxyl-terminal protease | 52 | NP_747159.1 |
| *Escherichai coli* | Carboxyl-terminal protease | 31 | D00674.1 |
| *Rhodopseudomonas palustris* | Periplasmic protease | 61 | ZP_00009772.1 |
| *Rhodobacter sphaeroides* | Periplasmic protease | 61 | ZP_00007601.1 |
| *Magnetospirillum magnetotacticum* | Periplasmic protease | 53 | ZP_00054906.1 |
| *Azotobacter vinelandii* | Periplasmic protease | 50 | ZP_00089764.1 |
| *Microbulbifer degradans* | Periplasmic protease | 50 | ZP_00065626.1 |

Genomic characterization of CtpA-deficient *B. suis* strain. The primers used to amplify the ctpA gene yielded a 1408-bp product from wild type *B. suis* strain 1330, and a 2189-bp product from strain 1330ΔctpA (FIG. 4). These results indicated that due to double-crossover event, a 471-bp region was deleted from ctpA gene, and the 1252-bp $Kan^R$ was inserted at the deletion site of strain 1330 genome. A PCR assay with this primer pair produced a 1408-bp band not only from wild type *B. suis*, but also from *B. abortus, B. canis* and *B. melitensis* (data not shown).

Figure 5A:
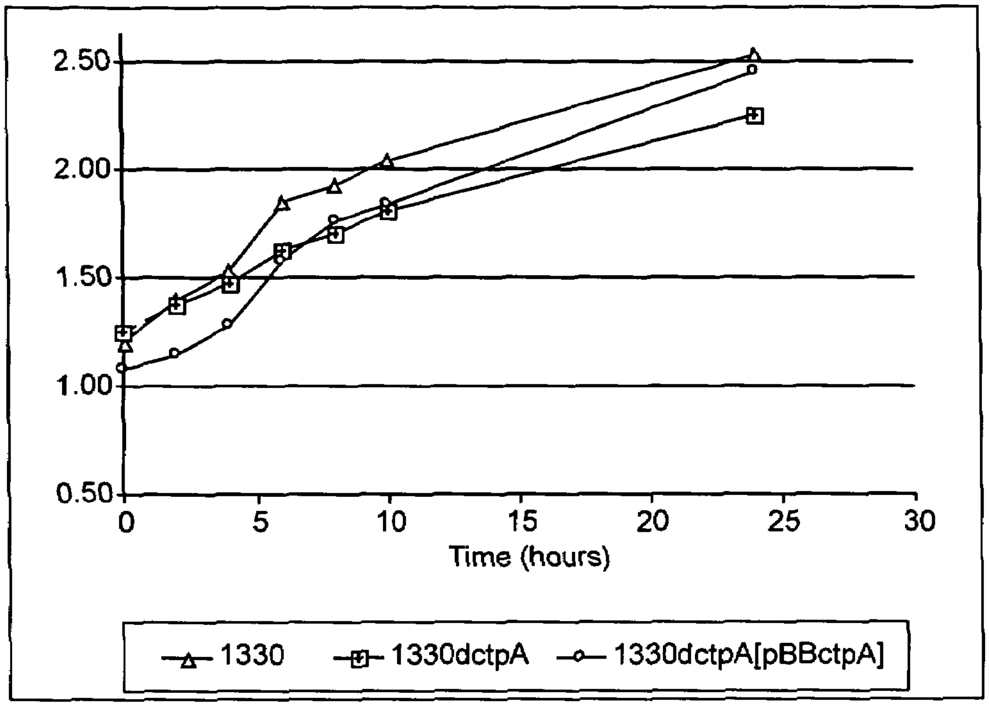
FIGS. 5A and B. Growth of *B. suis* strains. Single colonies of strains 1330, 1330ΔctpA, and 1330ΔctpA[pBBctpA] were grown overnight in TSB for 48 hours. The cells were pelletted in two equal aliquots by centrifugation. One pellet was resuspended in 1 ml of regular LB broth and used to inoculate 25 ml regular LB broth in Klett side-arm flask to 12 to 16 Klett units. The other pellet was resuspended in salt-free LB media and used to inoculate 25 ml salt-free LB broth in Klett flask to 8 to 16 Klett units. All cultures were grown at 42° C. at 180 rpm. Klett readings were recorded every two hours in a Klett Sumerson calorimeter.
Figure 5B:
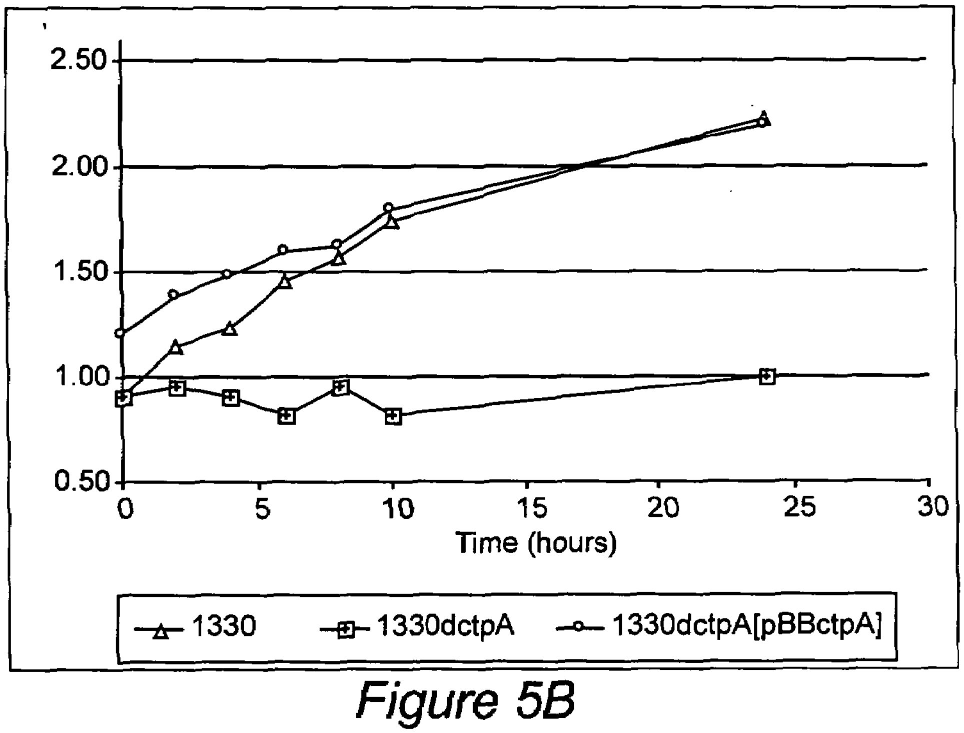
FIG. 5B: Growth of strains in salt-free LB media.

Growth rates of recombinant *B. suis* strains. The Prc-deficient *E. coli* strain exhibited salt-sensitive and thermo-sensitive growth (Hara et al., 1991). We investigate if the CtpA-deficient *B. suis* strain exhibits similar growth patterns. After three days of growth on regular TSA plates, colonies of strain 1330ΔctpA appeared approximately one third to half the size of the colonies of strain 1330 (data not shown). In regular LB broth, strain 1330ΔctpA grew approximately 50% slower than strain 1330 did (FIG. 5A) and exhibited no growth when incubated in salt-free LB broth (FIG. 5B). The growth rates of wild type versus mutant strains did not differ as a function of temperature, i.e., wild type and mutant strains grew at approximately similar rates at 30, 37 or 42° C. (data not shown). Colonies of strain 1330ΔctpA complemented with ctpA appeared equal in size to those of strain 1330 on TSA plates (data not shown). The growth rate of the complemented ΔctpA strain in regular or salt-free LB media was similar to the wild type strain 1330 (FIGS. 5A and 5B).

Complementation of CtpA and Prc activity in CtpA- or Prc-deficient strains. The absence of growth in salt-free media of strain 1330ΔctpA was reverted when the ctpA gene was introduced into this strain (resulting strain 1330ΔctpA [pBBΔctpA]). However, the salt sensitive growth of Prc-deficient *E. coli* strain JE7929 could not be reverted when *B. suis* ctpA gene was introduced into this strain.

Any leakage of periplasmic proteins. In Prc-deficient *E. coli* strain, significant amounts of RNase I and periplasmic alkaline phosphatase were leaked into the culture media (Hara et al. 1991). In order to find out if a similar phenomenon takes place in the CtpA-deficient *B. suis*, we precipitated the protein culture supernatant with acid, and used in SDS/PAGE and Western assays. In either assay, no significant differences were observed between the wild type strain 1330 and the CtpA-deficient strain 1330ΔctpA. No visible protein bands were seen on Western immunoblots with hyper immune anti-*Brucella* goat serum (data not shown), indicating that disruption in ctpA gene may not cause proteins to leak out of cells at significant level.

Phenotypic characterization of recombinant strains. We studied if the mutations in the ctpA gene made any effect on the proteins involved in lipopolysaccharide transport by assessing possible alterations in smooth phenotype. Similar to strain 1330, strain 1330ΔctpA did not retain crystal violet stain, indicating that both these strains possess a smooth phenotype (Table 3). In contrast, rough colonies of strain VTRS1 (Winter et al, 1996) retained crystal violet stain, confirming that these staining results were being correctly interpreted.

Cell morphology. Hara et al., (1991) reported that the Prc-deficient *E. coli* strain acquired a filamentous cell morphology when this strain was introduced into the salt-deficient growth media. We examined if a similar phenomenon takes place in the CtpA-deficient *B. suis*. Gram-staining results revealed that the CtpA-deficient strain did not produce a filamentous phenotype when it was grown in salt-deficient media (data not shown). However, we did not attempt to observe if any other morphological changes occurred, i.e., size of cells, or deformation of cells.

TABLE 3

*B. suis* strains - genes interrupted by mutation, phenotype, and clearance from mouse macrophage J774 cell lines. J774 cells were inoculated with *B. suis* strains. The recovery of strains 24 and 48 hours post-inoculation was determined.

| | | | Recovery of *Brucellae* from macrophages ($log_{10}$ CFU/well) | |
|---|---|---|---|---|
| Strain | Gene interrupted by knockout mutagenesis | Phenotype[a] | 24-hours of incubation | 48-hours of incubation |
| 1330 (wild) | — | Smooth | 5.37 ± 0.78 | 5.29 ± 0.34 |
| 1330ΔctpA | carboxyl-terminal protease (ctpA) | Smooth | 2.28 ± 0.21 | 5.01 ± 0.15 |
| VTRS1 | mannoseyltransferase (wboA) | Rough | — | — |

[a]Assessed with crystal violet colony staining

Persistence of *B. suis* strains in J774 macrophages. To study the attenuation characteristics of ΔctpA *B. suis* strain, the persistence of this strain in J774 mouse macrophage cells was studied (Table 3). At 24 and 48 hours post-inoculation, respectively 5.37 and 5.29 $log_{10}$ CFU of live *Brucella* were recovered from strain 1330, and 2.28 and 5.01 $log_{10}$ CFU were recovered from strain 1330ΔctpA. This reflects 3.09 and 0.28 $log_{10}$ decline of persistence of strain 1330ΔctpA compared with strain 1330, indicating that mutation in ctpA gene makes *B. suis* less persistent in J774 macrophages.

Survival in mice of the *B. suis* strains. To study the attenuation characteristics of ΔctpA *B. suis* strain, BALB/c mice were intraperitoneally inoculated with 5.0-5.3 $log_{10}$ CFU, and spleen CFU were determined 6 weeks postinoculation (Table 4). The virulent wild type strain 1330 persisted in mice for more than 6 weeks with only 0.83 $log_{10}$ CFU decline, whereas, strain 1330ΔctpA declined by 3.21 $log_{10}$ CFU during the same period. In comparison, splenic recovery of attenuated, rough *B. suis* strain VTRS1 declined 2.92 $log_{10}$ CFU.

TABLE 4

Clearance from mouse spleens of *B. suis* strains. Six-weeks old BALB/c mice were intraperitoneally inoculated with 5.0-5.3 $log_{10}$ CFU, and spleen CFU were determined 6 weeks postinoculation.

| Strain | Injected dosage ($log_{10}$ CFU/mouse) | CFU 6 weeks after inoculation (Mean + SE $log_{10}$/spleen) | Spleen size* |
|---|---|---|---|
| 1330 (wild) | 5.24 | 4.41 ± 0.18 | Enlarged |
| 1330ΔctpA | 5.25 | 2.04 ± 0.89[a] | Normal |
| VTRS1 | 4.97 | 2.05 ± 1.08[b] | Normal |

Figure 6:
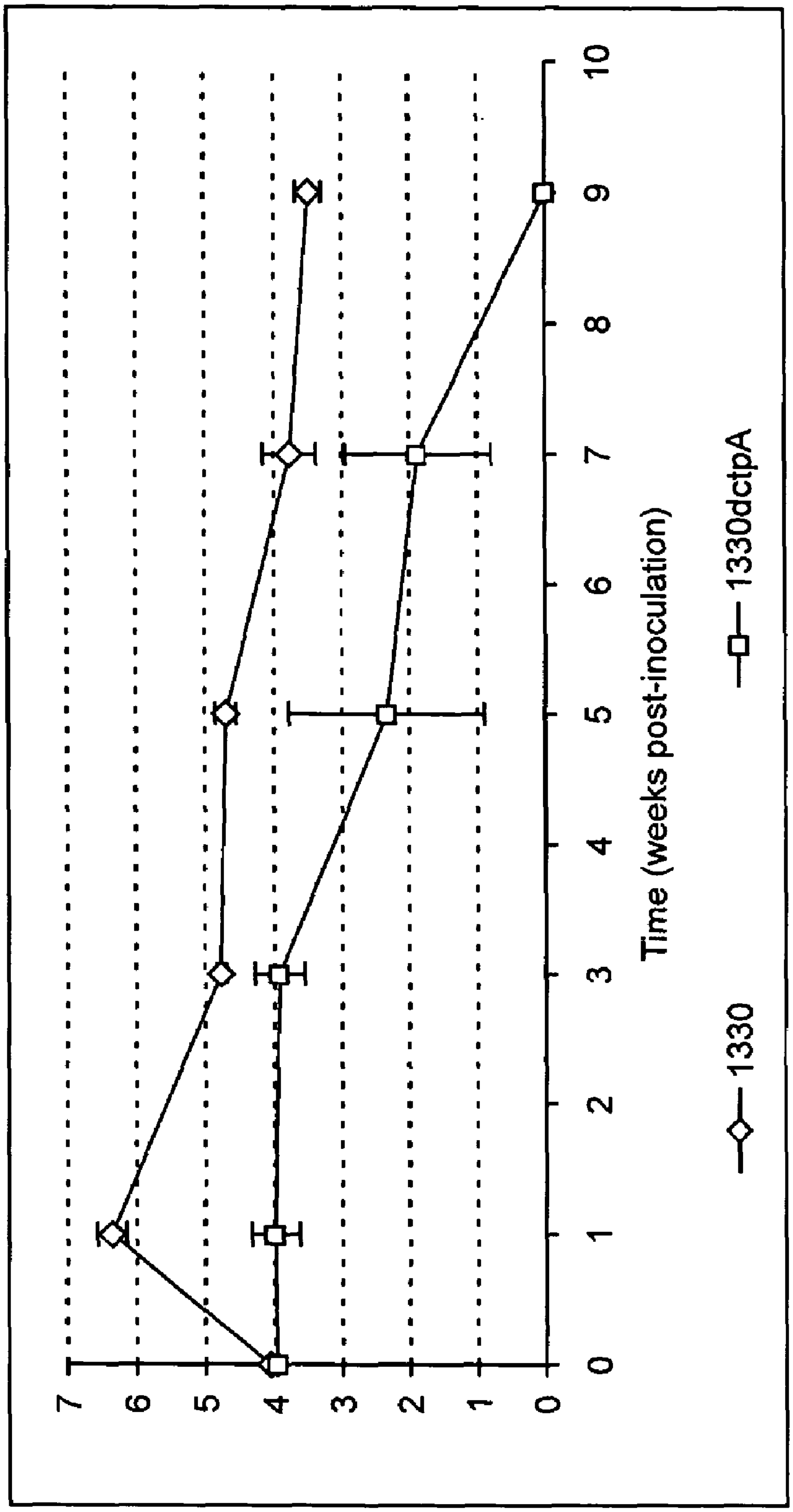
FIG. 6. Splenic clearance of *B. suis* strains in bi-weekly intervals. Groups of 25 mice each were intraperitoneally inoculated with 4.0-4.1 $\log_{10}$ CFU of strains 1330 or 1330ΔctpA and the splenic CFU counts were determined 1, 3, 5, 7, or 9 weeks post-inoculation.

*Spleen size of mice that were not infected with any bacteria was considered normal.
[a]Completely cleared in one out of eight mice
[b]Completely cleared in one out of seven mice In a separate trial, the splenic clearance of strains was estimated in every two-week intervals. In this work, mice were intraperitoneally inoculated with 4.0-4.1 $log_{10}$ CFU of strains 1330 or 1330ΔctpA, and spleen CFU were determined 1, 3, 5, 7, and 9 weeks post-inoculation (FIG. 6). One week after inoculation, the average splenic recovery of the strain 1330ΔctpA remained 4.0 $\log_{10}$ CFU, while it was 2.1 $\log_{10}$ CFU higher in the strain 1330. The persistence of the strain 1330ΔctpA declined faster than that of the strain 1330. Nine weeks post-inoculation, the CtpA-deficient strain cleared from spleens but strain 1330 was still present. It is noted that the SD values for the CptA mutant at 5 and 7 week post-inoculation (FIG. 6) were quite large because this strain had been completely cleared from the spleen of at least one mouse (i.e. 0 CFU).

Figure 7:
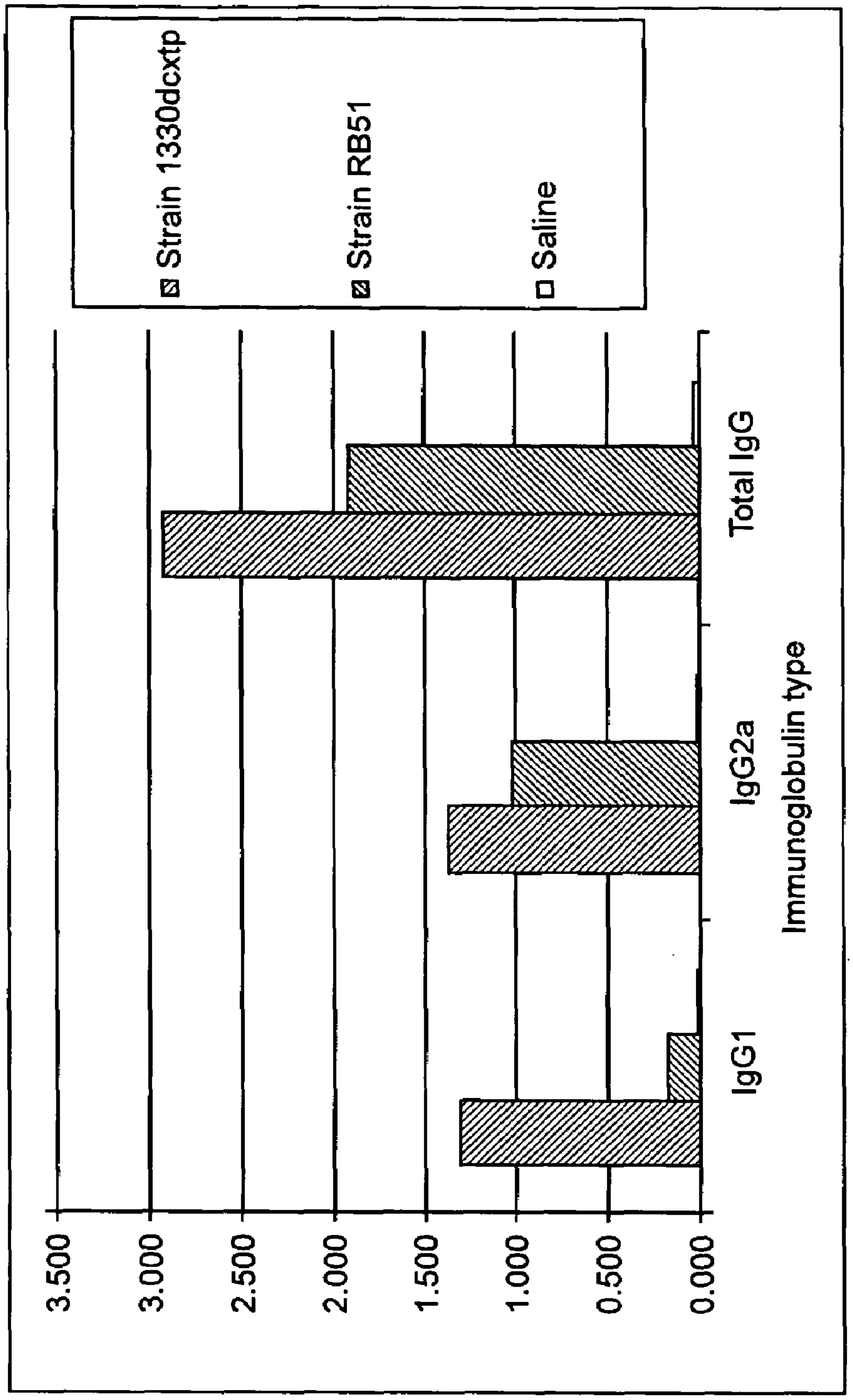
FIG. 7. ELISA detection of IgG1, IgG2a and total IgG antibodies in serum of mice vaccinated with strain 1330ΔctpA or inoculated with saline alone. Sera collected from eight mice of each group at 6 weeks post-vaccination were diluted 1/100 and assayed for the presence of specific antibodies. Sera collected from mice vaccinated with strain RB51 (obtained from A. Contreras, Virginia Tech) were used as a control. Results are shown as the mean of $OD_{450}$ of the color developed.

Induction of immune responses in mice. Specific antibody responses of the vaccinated mice were determined by ELISA (FIG. 7). Mice injected with saline produced negligible amounts of IgG1 or IgG2a recognizing *B. suis* antigens. Compared to the sera from mice vaccinated with *B. abortus* strain RB51 (obtained from A. Contreras, Virginia Tech), sera from mice vaccinated with strain 1330ΔctpA contained about seven fold greater IgG1 (P<0.001). Nevertheless, sera from 1330ΔctpA-vaccinated mice contained only slightly higher IgG2a levels than sera from RB51-vaccinated mice (P<0.01).

TABLE 5

Protection induced by recombinant *B. suis* strains against challenge with *B. suis* virulent strain 1330. Six weeks old BALB/c mice were injected with PBS or *B. suis* strains as shown. Six weeks post-injection, the mice were challenged with 4.7 $\text{Log}_{10}$ CFU of *B. suis* strain 1330. Spleen CFU were determined two weeks post-challenge.

| Vaccine strain | Dose injected $\log_{10}$ CFU | Recovery of strain 1330 from spleens $\log_{10}$ CFU | Units of protection $\log_{10}$ CFU | Spleen size* |
|---|---|---|---|---|
| PBS | — | 5.90 ± 0.24 | — | Larger than normal |
| VTRSI | Low dose 4.20 | 5.91 ± 0.54 | −0.01 | Larger than normal |
| | High dose 5.20 | 4.64 ± 0.39 | 1.26 | Normal |
| 1330ΔctpA | Low dose 4.34 | 2.70 ± 0.55 | 3.20 | Normal |
| | High dose 5.34 | 2.15 ± 0.96 | 3.75 | Normal |

*Spleen size of mice that were not infected with any bacteria was considered normal.

TABLE 6

Protection induced by recombinant *B. suis* strain 1330ΔctpA against challenge with *B. abortus* virulent strain 2308 and *B. melitensis* virulent strain 16M. Six weeks old BALB/c mice were injected with PBS or *B. suis* strain 1330ΔctpA as shown. Six weeks post-injection, the mice were challenged with *B. abortus* strain 2308 or *B. melitensis* strain 16M, and spleen CFU were determined two weeks post-challenge.

| Inoculation | Dose injected $\log_{10}$ CFU/mouse | Challenge strain | Challenge dose $\log_{10}$ CFU/mouse | Recovery of challenge strains from spleens $\log_{10}$ CFU/mouse | Units of protection $\log_{10}$ CFU/mouse |
|---|---|---|---|---|---|
| PBS | — | 2308 | 3.51 | 5.03 ± 0.07 | 4.71 |
| 1330ΔctpA | 5.332 | 2308 | 3.51 | 0.32 ± 0.78[a] | |
| PBS | — | 16M | 5.14 | 5.62 ± 0.29 | 0.37 |
| 1330ΔctpA | 5.32 | 16M | 5.14 | 5.25 ± 0.31 | |

[a]Completely cleared in five out of six mice

Protective efficacy of attenuated *B. suis* strains. Mice immunized with 4.34 and 5.34 $\log_{10}$ CFU of strain 1330ΔctpA demonstrated 3.20 and 3.75 $\log_{10}$ units of protection, respectively (Table 5). All colonies harvested from spleens of mice injected with this strain were sensitive to kanamycin, indicating that they all were from the challenge strain 1330 (kanS), as opposed to the vaccine strain 1330ΔctpA (kanR). In comparison, strain VTRS1 provided no protection when mice were vaccinated with 4.20 $\log_{10}$ CFU, but provided 1.26 $\log_{10}$ CFU protection when vaccinated with 5.20 $\log_{10}$ CFU dose. Nearly one-quarter of the colonies harvested from mice immunized with 5.20 $\log_{10}$ CFU of strain VTRS1 were resistant to kanamycin indicating that the VTRS1 dose had not been completely cleared from the spleens in 10 weeks. In a separate trial, it was shown that immunization with strain 1330ΔctpA induced 4.71 and 0.37 $\log_{10}$ CFU units of protection against challenge with strains 2308 and 16M, respectively (Table 6).

Discussion

The deduced amino acid sequence from ctpA gene showed substantial homology with the Ctps of a number of bacterial species. In addition, this deduced amino acid sequence showed considerable homology with the periplasmic proteases of other related bacterial species. The *B. suis* CtpA showed 31% homology at the amino acid level to Prc protein identified as carboxyl-terminal processing protease for PBP 3 of *E. coli* (Hara et al., 1991; Silber et al., 1992). Cell fractionation studies had indicated that Prc is localized in the periplasmic space of *E. coli* (Hara et al., 1991). Based on the greater homology between bacterial Ctps and periplasmic proteases we believe that these two protein groups are the same, even though they had been named differently. It is possible that *B. suis* CtpA is involved in carboxyl-terminal processing protease activities and is located in the periplasmic space of the cell. This possibility awaits further experimental confirmation.

Strains 1330ΔctpA and 1330 possessed a smooth phenotype. Apparently, the mutation of ctpA gene does not haveimpact on the transport of O-side chain to the outer membrane. Again this observation is consistent with CtpA affecting the processing of proteins as opposed to carbohydrates. Strain 1330ΔctpA produced relatively smaller colonies on TSA plates, and exhibited slower growth in regular growth media suggesting that the function of CtpA is important for the growth and cell division of *B. suis*. Zero growth of strain 1330ΔctpA in salt-free media suggests that ctpA function involves either directly or indirectly protection of the cell from osmotic stresses. Hara et al., (1991) observed that Prc-deficient *E. coli* did not grow in salt-free media. Apparently, in *E. coli* and in *B. suis* respectively, Prc and CtpA functions are dispensable for growth in a normal osmolar milieu. The reduced growth in salt-free media exhibited by CtpA-deficient mutant mimics that seen for the Prc-deficient mutant of *E. coli* (Hara et al., 1991) and further suggests that the *B. suis* CtpA is a protease. Prc-deficient *E. coli* grew in salt-free media at low temperatures (30° C.) but not at high temperatures (42° C.) exhibiting temperature dependency. In contrast, CtpA-deficient *B. suis* strain did not grow at any temperature when it was introduced into salt-free media, indicating that CtpA in *Brucella* does not have a temperature dependency.

Hara et al. (1991) reported that when the Prc-deficient *E. coli* cells were introduced into the salt-free media, those cells exhibited a filamentous phenotype. These workers attributed this phenomenon to the interruption of the processing/maturation of PBP 3 protein in Prc-deficient strain. The present work shows that the cells of the CtpA-deficient *B. suis* did not exhibit a filamentous shape when they were introduced into the salt-free growth media. This result suggests that CtpA may not be involved in the processing of PBP 3 of *B. suis*. However, this possibility awaits further experimental confirmation.

Colonies produced by strain 1330ΔctpA complemented with the ctpA gene were similar in size to those produced by wild type strain 1330. Additionally, the growth pattern of this strain was similar to that of strain 1330. These results indicate that complementation of ctpA gene restored the CtpA activity of mutant 1330ΔctpA. These results further suggest that the phenotype of strain 1330ΔctpA is the result of a specific mutation in ctpA and not a polar effect.

Hara et al., (1991) reported that disruption of prc gene of *E. coli* resulted in leakage of proteins from cells. However, the mutation in ctpA gene of *B. suis* did not cause any leakage of proteins, suggesting that this mutation may not affect the integrity of the cell wall.

When the ctpA gene was introduced into Prc-deficient *E. coli*, its growth in salt-free media could not be restored. This may be due to significant structural differences between the CtpA and Prc proteins. These proteins shared only 31% homology at the amino acid level.

Overall, the Prc and CtpA protein appear to regulate the salt-sensitive growth of *E. coli* and *B. suis*. However, unlike that of Prc, the activity of CtpA is not dispensable at different growth temperatures. Additionally, it is apparent that, contrary to Prc, CtpA is not involved in processing of the PBP that regulates murein synthesis/cell division, or retention of periplasmic proteins like RNaseI or alkaline phosphatase.

When grown in J774 macrophages, the persistence of strain 1330ΔctpA declined significantly after 24 hours of incubation, indicating that CptA is important for survival of *B. suis*, particular against early killing by macrophages and neutrophils. The clearance studies in mice revealed that one week after inoculation, significantly lower numbers of strain 1330ΔctpA were recovered than strain 1330. Nine weeks after inoculation, strain 1330ΔctpA was cleared completely from mouse spleens whereas strain 1330 was still present. These findings indicate that mutation in the ctpA gene makes *B. suis* attenuated. Overall, the slow growth of this mutant strain in enriched media, and its low persistence in mice and mouse macrophages suggest that it has a diminished capacity for extracellular and intracellular growth.

*Brucella* species are intracellular pathogens, and therefore, cell-mediated immune (CMI) responses are critically important in preventing brucellosis (Pavlov et al., 1982; Zhan et al., 1993; Murphy et al., 2001). Cattle brucellosis vaccine *B. abortus* strain RB51 induces preferentially Th1 type associated CMI responses and protects cattle against *Brucella* infections (Vemulapalli et al., 2000a; Vemulapalli et al., 2000 b). In vaccinated mice, strain 1330ΔctpA produced IgG2a at a slightly higher level than did strain RB51. In addition, unlike strain RB51, strain 1330ΔctpA also induced a greater level of IgG1. Overall, the IgG1 and IgG2a antibody responses induced by strain 1330ΔctpA appear more balanced than those induced by strain RB51.

In the protection study, all colonies harvested from mice vaccinated with strain 1330ΔctpA were sensitive to kanamycin indicating that this strain has been completely cleared from mouse spleens during the 10-week immunization period. Strain 1330ΔctpA induced excellent protection against challenge with *B. suis* strain 1330, and the level of protection increased slightly with an increased vaccine dose. The protection induced by strain 1330ΔctpA was much greater than that induced by rough *B. suis* strain VTRS1. The superior protection against 1330 challenge by the strain 1330ΔctpA compared with that elicited by strain VTRS1 can be attributed to two reasons: (A) Strain 1330ΔctpA being a smooth strain may be inducing antibody responses to O-side chain. This is likely to reflect published literature suggesting that the specific humoral and cellular responses to the O-side chain are important in producing good protection (Araya et al., 1989; Araya and Winter, 1990; Corbel, 1997). (B) Strains 1330 and 1330ΔctpA belong to biovar-1 whereas, VTRS1 belongs to biovar-4. Apparently, a biovar-4 vaccine is not as efficient as a biovar-1 vaccine against challenge with biovar-1 challenge. Within a single species of *Brucella* (e.g. *Brucella suis*) different groups exhibiting expression of different antigens (protein types of sugar types) are described as "biovars". For instance, *Brucella suis* biovar-1 and biovar-4 cause brucellosis in swine in other animals. The bacteria in these two groups share many similarities, but they differ to some degree in terms of the expression of specific antigens.

Strain 1330ΔctpA also induced excellent protection against challenge with *B. abortus* strain 2308, indicating that this strain is effective in providing protection against challenge with heterologous *Brucella* species. Nevertheless, strain 1330ΔctpA did not induce satisfactory protection against challenge with *B. melitensis* strain 16M. The less protective efficacy of strain 1330ΔctpA against 16M challenge may be attributable to the structural differences of O-side chain between *B. melitensis* and *B. suis*. Recent work has revealed that monoclonal antibodies to *B. abortus* O-side chain (Bru-38) do not recognize the O-side chain of *B. melitensis*, suggesting that the O-side chain of other *Brucella* species may not induce protection against *B. melitensis* challenge (unpublished data).

As a vaccine candidate, strain 1330ΔctpA possesses a number of advantages over the other brucellosis vaccines. The currently used vaccine candidates, *B. abortus* strains RB51 (Schurig et al., 1991), S19 (Nicoletti, 1990), and *B. melitensis* strain Rev1 (Alton et al., 1967), were developed through laboratory selection procedures, and therefore, their genetic makeups are not known. Even though they induce substantial protection against brucellosis in animals, vaccination with strains S19 (Manthei and Beckett) or Rev1 (Blasco and Bardenstein) sometimes result in abortion. Strains S19 (Young 1983) and Rev1 (Blasco, and Diaz, 1993; Young 1983) are pathogenic to humans. Strain RB51 is resistant to the antibiotic rifampicin, one of the very few antibiotics available for treatment of brucellosis in humans (Joint FAO/WHO, 1986). In contrast, strain 1330ΔctpA was developed by knockout mutagenesis and its genetic make up is well defined. Further, it induces excellent protection against challenge with *B. abortus* strain 2308 or *B. suis* strain 1330.

Example 2

Electron Microscopy Studies

Figure 8:
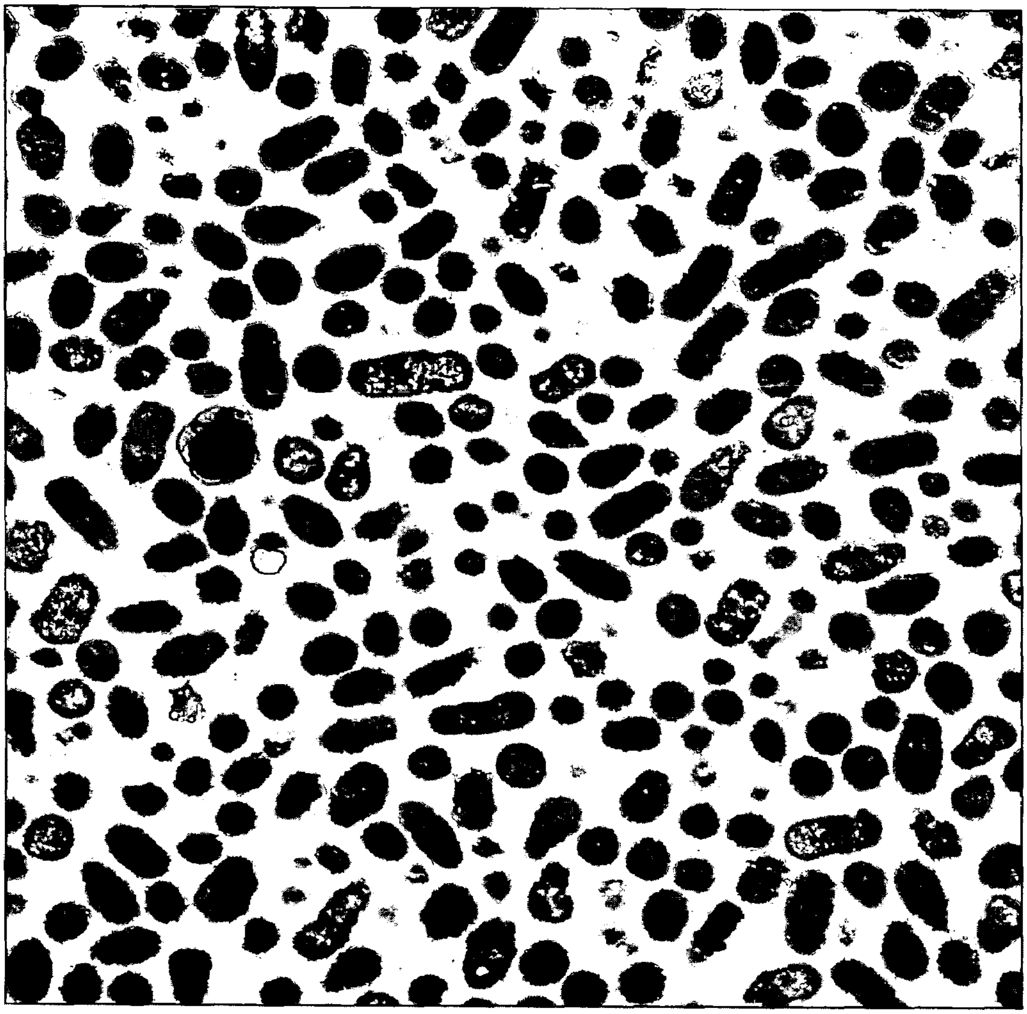
FIG. 8. Cell morphology of strain 1330 grown in LB media with salt, determined by scanning electron microscopy. The cells possessed the native coccobacillus shape of *Brucella*. Additionally, the cells revealed the typical ultrastructure of Gram negative bacteria, namely, the outer membrane, periplasmic space, and cytoplasmic membrane. The magnification was ×10,000.
Figure 9:
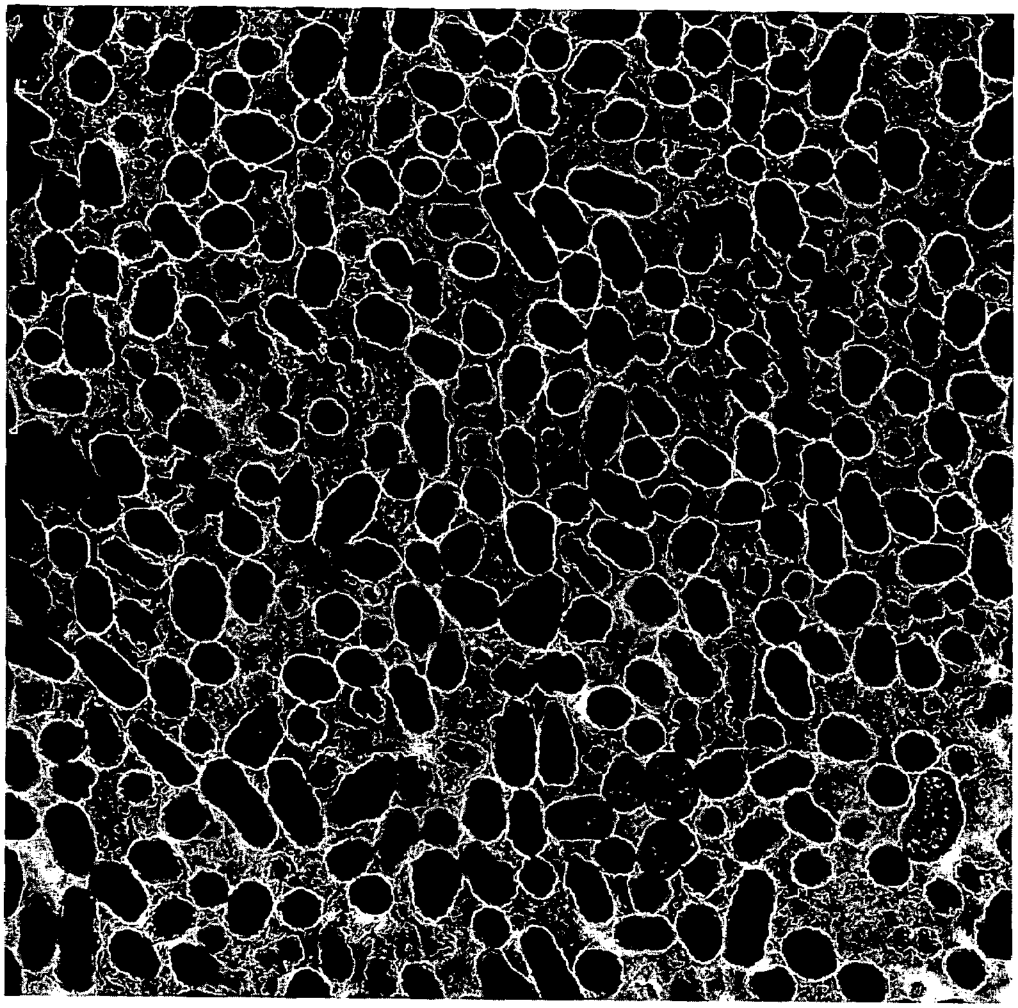
FIG. 9. Cell morphology of strain 1330 grown in LB media without salt, determined by scanning electron microscopy. The cells possessed the native coccobacillus shape of *Brucella*, and typical ultrastructure of Gram negative bacteria. A significant difference cannot be seen in cell morphology of strain 1330, when salt is present or absent in growth media. The magnification was ×10,000.

When observed with the electron microscope, wild type *Brucella suis* (strain 1330) cells possessed their native coccobacillus cell morphology. No difference in cell morphology was seen between strain 1330 cells grown in growth media with salt (FIG. 8) or without salt (FIG. 9). Additionally, these cells possessed the typical ultrastructure of *Brucella* cells, namely, the outer membrane, periplasmic space, and cytoplasmic membrane.

Figure 10:
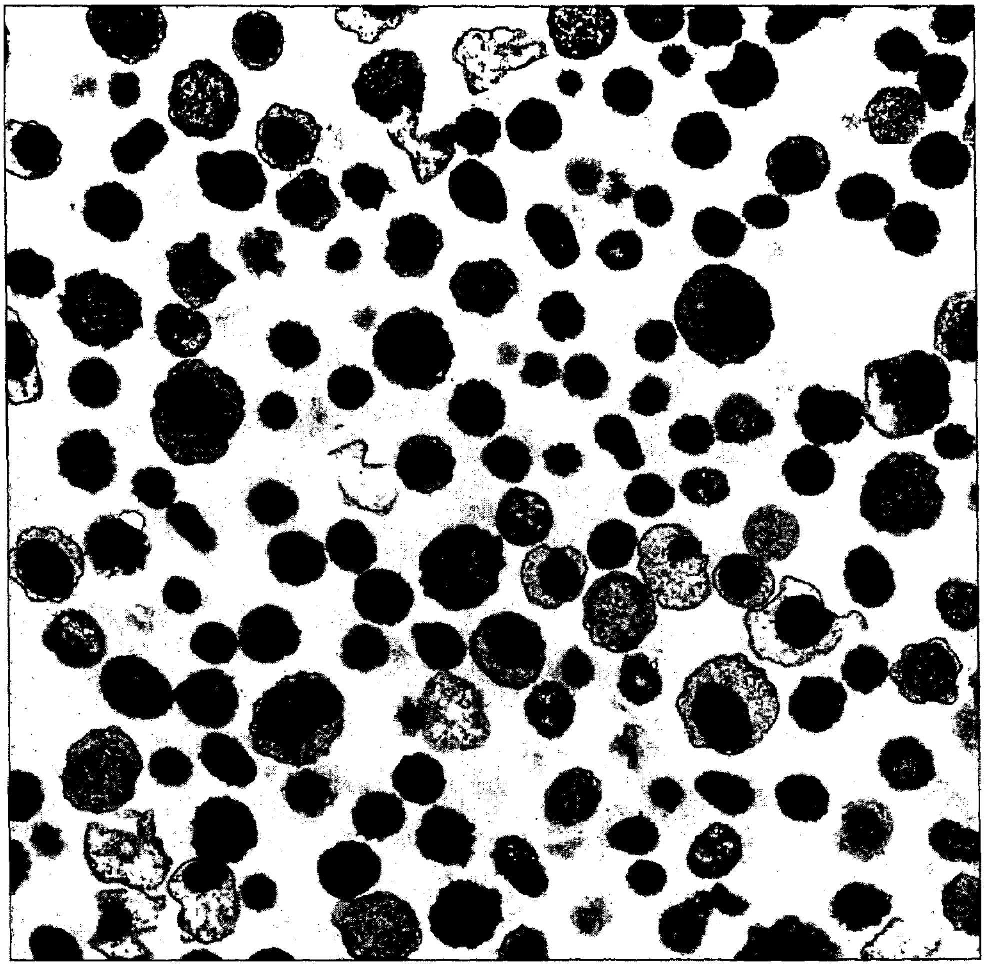
FIG. 10. Cell morphology of strain 1330ΔctpA grown in LB media with salt, determined by scanning electron microscopy. The cells acquired a spherical shape instead of its native coccobacillus shape of *Brucella*. The cell diameter apparently increased slightly. Additionally, the cells partially lost the typical ultrastructure of Gram negative bacteria. The outer membrane apparently separated from some of the cells. However, the integrity of the rest of the cell was not changed. The magnification was ×10,000.
Figure 11:
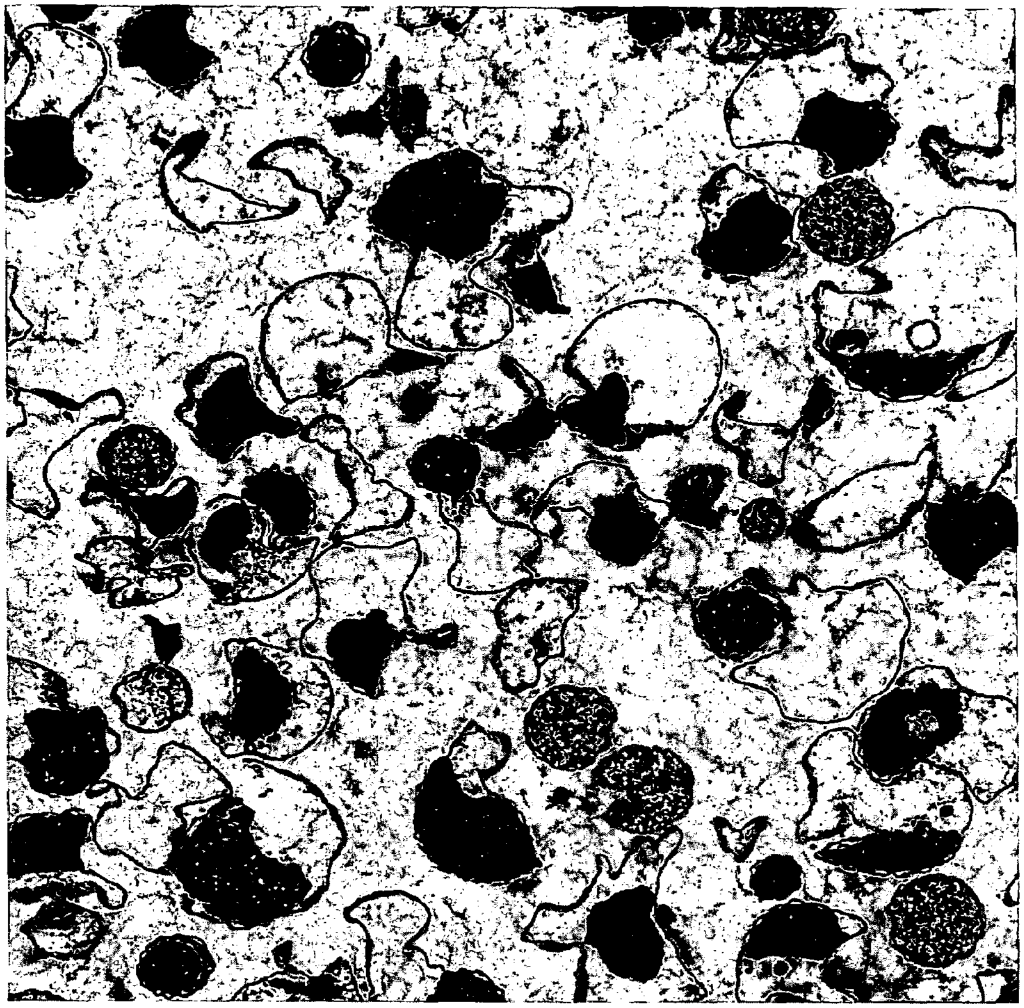
FIG. 11. Cell morphology of strain 1330ΔctpA grown in LB media without salt, determined by scanning electron microscopy. The cells lost their native coccobacillus shape of *Brucella*. Additionally, the cells lost the typical ultrastructure of Gram negative bacteria. The outermembrane dissociated from cells. The integrity of the cell was changed. The magnification was ×10,000.

However, the invented strain 1330 ctpA exhibited a spherical cell morphology when grown in media with salt. The cell diameter also appeared to be increased slightly. The outer membrane was partially separated from some of the cells (FIG. 10). When grown in media without salt, the membrane dissociated from the rest of the cell, and the cell morphology was significantly altered (FIG. 11).

In other bacteria (i.e., *Escherichia coli* and *Bacillus subtilis*), when the expression or processing of Penicillin-Binding Proteins-1 and -2 (PBP-1 and PBP-2) is inhibited, the cells are known to acquire a spherical cell morphology, and the cell diameter increases. Accordingly, it is likely that in the invented strain 1330 ctpA, the expression or processing of PBP-1 and/or PBP-2 has been altered due to mutation of the CtpA protein.

Further, in other bacteria, PBP enzymes are involved in synthesis of the cell wall peptidoglycan layer. Therefore, the dissociation of the cell membrane from the rest of the cell and the loss of cell integrity of strain 1330 ctpA is likely attributable to alteration of the functions of PBP-1 and PBP-2 enzymes due to mutation of the ctpA gene.

REFERENCES FOR EXAMPLES 1 AND 2

Acha, P., and B. Szyfres. 1980. Zoonoses and communicable diseases common to man and animals, p.28-45. In Pan American Health Organization, Washington, D.C.

Alton, G. G., L. M. Jones, and D. E. Pietz. 1975. Laboratory techniques in Brucellosis. World Health Organization monograph series no. 55. In World Health Organization, Geneva, Switzerland.

Altschul, S., W. Gish, W. Miller, E. Myers and D. Lipman. 1990. Basic local alignment search tool. *J. Mol. Biol.* 215:403-410.

Anderson, T. D., N. F. Cheville, and V. P. Meador. 1986. Pathogenesis of placentitis in the goat inoculated with *Brucella abortus*. II. Ultrastructural studies. Vet. Pathol. 23:227-239.

Araya, L. N., and A. J. Winter. 1990. Comparative protection of mice against virulent and attenuated strains of *Brucella abortus* by passive transfer of immune T cells or serum. Infect. Immun. 58:254-256.

Araya, L. N., P. H. Elzer, G. E. Rowe, F. M. Enright, and A. J. Winter. 1989. Temporal development of protective cell-mediated and humoral immunity in BALB/c mice infected with *Brucella abortus*. J. Immunol. 143:3330-3337.

Arenas, G. N., A. S. Staskevich, A. Aballay, and L. S. Mayorga. 2000. Intracellular trafficking of *Brucella abortus* in J774 macrophages. Infect. Immun. 68:4255-4263.

Baldwin, C. L., and A. J. Winter. 1994. Macrophages and *Brucella*. Immunol. Ser. 60:363-380.

Chung, S., and D. A. Bryant. 1992. p 69-72. In N. Murata (ed.), Research in Photosynthesis, vol. I.

Corbel, M. J. 1997. Brucellosis: an overview. Emerg. Infect. Dis. 3:213-221.

Corbel, M. J., and W. J. Brinley Morgan. 1984. Genus *Brucella* Meyer and Shaw 1920, 173 AL. p. 377-390. In N. R. Krieg and J. G. Holt (ed.), Bergey's Manual of Systematic Bacteriology, vol. 1. Williams and Wilkins, Baltimore.

Dalbey, R. E., and G. von Heijne. 1992. Signal peptidases in prokaryotes and eukaryotes—a new protease family. Trends Biochem. Sci. 17:474-478.

Francis M. S., and C. J. Thomas. 1997. f1 Mutants in the CtpA copper transporting P-type ATPase reduce virulence of *Listeria monocytogenes*. Microbial Pathogenesis 22:67-78.

Hara, H., Y. Yamamoto, A. Higashitani, H. Suzuki, and Y. Nishimura. 1991. Cloning, mapping, and characterization of the *Escherichia coli* prc gene, which is involved in C-terminal processing of penicillin-binding protein 3. J. Bacteriol. 173:4799-4813.

Inagaki, N., Y. Yamamoto, H. Mori, and K. Satoh. 1996. Carboxyl-terminal processing protease for the D1 precursor protein: cloning and sequencing of the spinach cDNA. Plant Mol. Biol. 30:39-50.

Islam, M. R., J. H Grubb, and W. S. Sly. 1993. C-terminal processing of human beta-glucuronidase. The propeptide is required for full expression of catalytic activity, intracellular retention, and proper phosphorylation J. Biol. Chem. 268:22627-22633

Jimenez de Bagues, M. P., C. M. Martin, and J. M. Blasco. 1992. An ELISA with *Brucella* lipopolysaccharide antigen for the diagnosis of *B. melitensis* infection in sheep and for the evaluation of serological responses following subcutaneous or conjunctival *B. melitensis* strain Rev 1 vaccination. Vet Microbiol. 30:233-241.

Keiler, K. C., and R. T. Sauer. 1998. p. 460-461 In A. J. Barrett, N. D. Rawlings, and J. F. Woessner (ed.), Handbook of Proteolytic Enzymes, Academic Press, London.

Keiler, K. C., P. R. H. Waller, and R. T. Sauer. 1996. Role of a peptide tagging system in degradation of proteins synthesized from damaged messenger RNA. Science 271: 990-993.

Kovach, M. E., R. W. Phillips, P. H. Elzer, R. M. Roop II, and K. M. Peterson. 1994. pBBR1 MCS: a broad-host range cloning vector. BioTechniques 16:800-802.

Laemmli, U. K. 1970. Cleavage of structural proteins during the assembly of the head of bacteriophage T4. Nature 227:680-685.

McQuiston, J. R., G. G. Schurig, N. Sriranganathan, and S. M. Boyle. 1995. Transformation of *Brucella* species with suicide and broad host-range plasmids. Methods Mol. Biol. 47:143-148.

Menon, N. K., J. Robbins, M. D. Vartanian, D. Patil, H. D. Peck, A. L. Menon, R. L. Robson, and A. E. Przybyla. 1993. Carboxy-terminal processing of the large subunit of [NiFe] hydrogenases. FEBS Lett. 331:91-95.

Murphy, E. A., J. Sathiyaseelan, M. A. Parent, B. Zou and C. L. Baldwin. 2001. Interferon-gamma is crucial for surviving a *Brucella abortus* infection in both resistant C57 BL/6 and susceptible BABB/c mice. Immunology 103: 511-518.

Naroeni, A., N. Jouy, S. Ouahrani-Bettache, J. P. Liautard, and F. Porte. 2001. *Brucella suis*—impaired specific recognition of phagosomes by lysosomes due to phagosomal membrane modifications. Infect. Immun. 69:486-493.

National Academy Press. 1977. *Brucellosis research: an evaluation*. p. 61-77. In Report of the subcommittee on Brucellosis research. National Academy Press, Washington, D.C.

Oelmüller, R., R. G. Herrmann, and H. B. Pakrasi. 1996. Molecular studies of CtpA, the carboxyl-terminal processing protease for the D1 protein of the photosystem II reaction center in higher plants. J. Biol. Chem. 271: 21848-21856.

Paetzel, M. and R. E. Dalbey. 1997. Catalytic hydroxyl/amine dyads within serine proteases. Trends Biochem. Sci. 22:28-31.

Pakrasi, H. B. 1998. p. 462-463. In A. J. Barrett, N. D. Rawlings, and J. F. Woessner (ed.), Handbook of Proteolytic Enzymes, Academic Press, London.

Paulsen, I. T., R. Seshadri, K. E. Nelson, J. A. Eisen and S. M. Boyle. 2002. The *Brucella suis* genome reveals fundamental similarities between animal and plant pathogens and symbionts. PNAS 99:13148-13153.

Pavlov, H., M. Hogarth, I. F. C. McKenzie and C. Cheers. 1982. In vivo and in vitro effects of monoclonal antibody to Ly antigen on immunity to infection. Cell. Immunol. 71:127-138.

Pizarro-Cerda, J., S. Meresse, R. G. Parton, G. van der Goot, A. Sola-Landa, I. Lopez-Goni, E. Moreno, and J. P. Gorvel. 1998. *Brucella abortus* transits through the autophagic pathway and replicates in the endoplasmic reticulum of nonprofessional phagocytes. Infect. Immun. 66:5711-5724.

Ried, J. L., and A. Colmer. 1987. An npt-sacB-sacR cartridge for constructing directed, unmarked mutations in gram-negative bacteria by marker exchange-eviction mutagenesis. Gene. 57:239-246.

Sambrook, J., E. F. Fritsch and T. Maniatis. 1989. Molecular cloning: a laboratory manual, 2 nd ed. Cold Spring Harbor Laboratory Press, Cold Spring Harbor, N.Y.

Satoh, K. 1998. p. 463-464. In A. J. Barrett, N. D. Rawlings, and J. F. Woessner (ed.), Handbook of Proteolytic Enzymes, Academic Press, London.

Schurig, G. G., R. M. Roop, T. Bagchi, S. M. Boyle, D. Buhrman, and N. Sriranganathan. 1991. Biological properties of RB51: a stable rough strain of *Brucella abortus*. Vet. Microbiol. 28:171-188.

Silber, K. R., K. C. Keiler, and R. T. Sauer. 1992. Tsp: a tail-specific protease that selectively degrades proteins with nonpolar C termini. Proc. Natl. Acad. Sci. U. S. A. 89:295-299.

Theroux, S. J., T. E. Redlinger, R. C. Fuller, and S. J. Robinson. 1990. Gene encoding the 5.7-kilodalton chlorosome protein of Chloroflexus aurantiacus: regulated message levels and a predicted carboxy-terminal protein extension. J. Bacteriol. 172:4497-504.

Vemulapalli, R., A. J. Duncan, S. M. Boyle, N. Sriranganathan, T. E. Toth, and G. G. Schurig. 1998. Cloning and sequencing of yajC and secD homologs of *Brucella abortus* and demonstration of immune responses to YajC in mice vaccinated with *B. abortus* RB51. Infect. Immun. 66:5684-5691.

Vemulapalli R., Y. He, L. S. Buccolo, S. M. Boyle, N. Sriranganathan, G. G. Schurig. 2000a. Complementation of *Brucella abortus* RB51 with a functional wboA gene results in O-antigen synthesis and enhanced vaccine efficacy but no change in rough phenotype and attenuation. Infect. Immun. 68:3927-3932.

Vemulapalli R., Y. He, S. Cravero, S. M. Boyle, N. Sriranganathan, and G. G. Schurig. 2000b. Overexpression of protective antigen as a novel approach to enhance vaccine efficacy of *Brucella abortus* strain RB51. Infect. Immun. 68:3286-3289.

White, P. G., and J. B. Wilson. 1951. Differentiation of smooth and nonsmooth colonies of *Brucellae*. J. Bacteriol. 61:239-240.

Winter, A. J., G. G. Schurig, S. M. Boyle, N. Sriranganathan, J. S. Bevins, F. M. Enright, P. H. Elzer, and J. D. Kope. 1996. Protection of BALB/c mice against homologous and heterologous species of *Brucella* by rough strain vaccines derived from *Brucella melitensis* and *Brucella suis* biovar 4. Am. J. Vet. Res. 57:677-683

Yamamoto, Y., N. Inagaki, and K. Satoh. 2001. Overexpression and characterization of carboxyl-terminal processing protease for precursor D1 protein: regulation of enzyme-substrate interaction by molecular environments. J. Biol. Chem. 276:7518-7525

Zhan, Y., J. Chang and C. Cheers. 1993. Cytokine response of, T-cell subsets from *Brucella abortus* infected mice to soluble *Brucella* proteins. Infect. Immun. 61 :2841-2847.

Example 3

The carboxyl-terminal protease (CtpA) proteins are a novel family of enzymes. The putative tail-specific protease (TspA) of *Brucella melitensis* strain 16M is a member of the CtpA family. Sequence analyses predicted that the mature TspA protein is localized in the periplasmic space. Out of total 443 amino acids of the *B. melitensis* TspA sequence, 174 amino acids are conserved among the CtpA proteins of at least six bacterial species. The Asp238, Arg240, Ser300, Glu303, and Lys325 amino acid residues of *B. melitensis* TspA sequence correspond with those amino acid residues critical for the catalytic activity of the CtpA protein of *Synechocystis* species. Among these, Ser300/Lys325 appears to be the catalytic dyad of this protein. A tspA mutant *B. melitensis* strain (16MΔtspA), generated by allelic exchange, produced smaller colonies on enriched agar plates, and exhibited zero growth in salt-free enriched medium compared to the wild type strain 16M or the complemented mutant strain 16MΔtspA[ctpA$^+$]. Western immunoblotting assays revealed that the tspA mutant up-regulated the expression of at least two proteins. Electron microscopy revealed that in contrast to the native coccobacillus shape of wild type strain, the tspA mutant possessed a spherical shape with an increased cell diameter. In the J774 mouse macrophage cell line, 24 hours after infection, the survival of the tspA mutant strain declined by approximately 1.2 $\log_{10}$ colony forming units relative to the wild type strain. These observations suggest that the TspA protein is involved in determining growth, protein expression, cell morphology, and intracellular persistence of *B. melitensis*.

Key words: *Brucella melitensis*, carboxyl-terminal protease, Tail-specific protease, morphology, protein expression, intracellular persistence.

INTRODUCTION

Brucellae are gram-negative intracellular bacterial pathogens of both humans and animals (Corbel and Brinley Morgan, 1984). Among the six recognized *Brucella* species, *Brucella melitensis* is the main etiologic agent involved in ovine and caprine brucellosis and is also the most pathogenic species for humans (Acha and Szyfres, 1980). The pathological manifestations of brucellosis are diverse and include arthritis, endocarditis and meningitis in man, whereas animal brucellosis is characterized by spontaneous abortion (Young, 1983). Molecular characterization of cellular factors involved in regulating critical cellular functions would enhance the basic knowledge about physiology of bacteria. Additionally, identifying the factors important for intracellular persistence of Brucella will aid development of live attenuated vaccines against this bacterium.

Many proteins destined for extracytoplasmic locations are initially synthesized as precursor forms and processed into mature forms by proteolytic cleavage to remove short peptide sequences, either near the amino terminus or near the carboxyl terminus of such proteins. The endoproteases responsible for cleaving of amino-terminal peptides are called amino-terminal processing proteases and have been identified and studied in a number of systems (Dalbey and Von Heijne, 1992). During recent years, a relatively new class of endoproteases with carboxyl-terminal processing activities has been described in various bacteria and organellar systems. These proteins have been designated as Carboxyl-Terminal Protease (CtpA) proteins. The CtpA proteins are serine proteases that utilize a Ser/Lys catalytic dyad instead of the well-known Ser/His/Asp catalytic triad (Paetzel and Dalbey, 1997).

As a whole CtpA proteins are not well understood. To date, the best-characterized CtpA is that from the cyanobacterium Synechocystis sp. strain PCC 6803 (Shestakov et al., 1994). This enzyme is responsible for processing of the D1 precursor polypeptide of Photosystem II (Nixon et al., 1992). The CtpA protein is also involved in D1 processing in higher plants (Takahashi et al., 1988), and green algae Scenedesmus obliquus (Trost et al., 1997). Another well-studied CtpA is the tail-specific protease (Tsp) enzyme from E. coli (Silber et al., 1992). The E. coli Tsp is responsible for cleavage of C-terminal 11 amino acid residues of precursor form of Penicillin-Binding Protein-3 (PBP-3) (Hara et al., 1991). The PBP-3 is believed to involve in determining division of rod-shaped cells in bacteria (Popham and Young, 2003). A mutant E. coli strain deficient in Tsp expression was defective in processing of PBP-3 (Hara et al., 1989, 1991), and exhibited filamentous cell morphology, in contrast to the cocco-bacillus morphology of the wild type E. coli (Hara et al., 1991). Additionally, this mutant showed thermo-sensitive growth on salt-free L-agar plates, suggesting that Tsp was involved in protection of cell from thermal and osmotic stresses (Hara et al., 1991). More recently, Tsp has been shown to recognize and degrade several aberrant proteins with nonpolar C-termini, with strongest preference for alanine, at the three C-terminal residues (Keiler et al., 1996).

A putative CtpA is present in Borrelia burgdorferi strain B31 (Ostberg et al., 2004). Inactivation of the ctpA gene encoding this protein resulted in altered expression pattern of a number of proteins. The integral outermembrane protein P13 and the hypothetical protein BB0323 were identified as the substrates for the CtpA of this bacterium (Ostberg et al., 2004). A tsp homologue that expresses a CtpA protein is present in Salmonella typhimurium. The tsp mutant S. typhimurium had a reduced survival within macrophages suggesting that this gene may play a role in virulence (Baumler et al., 1994). A CtpA protein has also been identified in Bartonella bacilliformis, but no target for this enzyme has been identified yet. The ctpA gene encoding this protease is located immediately upstream of the ialAB locus that confers the bacterium the ability to invade human erythrocytes (Mitchell et al., 1997).

The knowledge about protein processing and protein modification in Brucella is limited. We recently reported that B. suis produces a putative CtpA protein that is involved in regulating the growth, cell morphology and intracellular persistence of this bacterium (Bandara et al., 2005, in press). A homologue of genes encoding CtpA proteins, designated tspA (GenBank locus tag BMEI0214 and Gene ID:1195926) is present on B. melitensis 16M chromosome I (Paulsen et al., 2002). In the present communication we report that the tspA gene influences the salt-sensitive growth, protein expression, cell morphology and intracellular persistence of B. melitensis.

Methods

Bacterial Strains, Plasmids, and Reagents

Brucella melitensis strain 16M was obtained from our culture collection. Brucellae were grown in LB broth (Difco Laboratories, Sparks, Md.) with or without sodium chloride at 37° C. to determine whether growth was osmo-sensitive. For all other assays, brucellae were grown either in trypticase soy broth (TSB) or on trypticase soy agar (TSA) plates (Difco) at 37° C. in the presence of 5% $CO_2$ as previously described (Schurig et al., 1991). Bacteria containing plasmids were grown in presence of ampicillin or kanamycin at 100 µg/ml concentration as described below. The mouse macrophage-like cell line was J774 obtained from American Type Culture Collection (Manassas, Va.).

All experiments with live brucellae were performed in a Biosafety Level 3 facility at the Infectious Disease Unit of the Virginia-Maryland Regional College of Veterinary Medicine as per standard operating procedures approved by the Centers for Disease Control and prevention.

DNA and Protein Sequence Analyses

The nucleotide sequence of tspA gene was analyzed with DNASTAR software (DNASTAR, Inc., Madison, Wis.). The deduced protein sequence of the tspA gene was aligned with the protein sequences of other bacteria using the ClustalV (PAM250) megalign program of the DNASTAR. The sequences of proteins that were more than 59% identical to the TspA were used in this analysis. The SignalP 3.0 Server of the Technical University of Denmark located at the website at cbs.dtu.dk (Bendtsen et al., 2004) was employed to predict the presence of any signal sequence of the putative TspA protein. The destination of the TspA protein upon translation and processing was predicted using the Subloc v1.0 server of the Institute of Bioinformatics of the Tsinghua University at the website located at bioinfo.tsinhua.edu.cn.

Mutation of the B. melitensis tspA Gene by Allelic Exchange

The tspA of B. melitensis shares 99% homology at amino acids level with the ctpA gene encoding putative CtpA protein of B. suis. A suicide vector (pGEMctpAK) that we previously used to mutate the ctpA gene of B. suis (Bandara et al., 2005-in press) was used to mutate the tspA gene of B. melitensis. One microgram of pGEMctpAK was used to electroporate B. melitensis strain 16M with a BTX ECM-600 electroporator (BTX, San Diego, Calif.), as described previously (McQuiston et al., 1995); two colonies of strain 16M were obtained from a TSA plate containing kanamycin (100 µg/ml). These colonies were streaked on a TSA plate containing ampicillin (100 µg/ml) to determine if a single- or double-crossover event had occurred. Both the colonies did not grow on ampicillin containing plates suggesting that a double-crossover event had occurred in them. PCR with a primer pair (forward primer 5 '-GGGGTACCGTGGTG-GACTGA-3 ' (SEQ ID NO: 12) and reverse primer 5 '-GGCTGCAGTCCCGCGTTTTTGTCTT-3 ') (SEQ ID NO: 13) (Ransom Hill Bioscience, Inc., Ramona, Calif.) confirmed that a double-crossover event had taken place in the two transformants. One of these strains was chosen for further analyses and designated 16MΔtspA.

Complementation of tspA Gene Activity in Mutant 16MΔtspA

We had previously cloned the 1.4-kb DNA fragment containing *B. suis* ctpA gene into the broad-host range vector pBBR4MCS (Kovach et al., 1995) to produce recombinant plasmid pBBctpA (Bandara et al., 2005-in press). One microgram of pBBctpA was used to electroporate the tspA mutant *B. melitensis* strain 16MΔtspA; several colonies of strain 16MΔtspA were picked from a TSA plate containing ampicillin (100 μg/ml). One of these colonies was chosen for further analyses and designated as 16MΔtspA[ctpA$^+$].

Denaturing Gel Electrophoresis of Proteins and Western Blotting

The wild type *B. melitensis* strain 16M, the tspA mutant 16MΔtspA and the complemented tspA mutant 16MΔtspA [ctpA$^+$] were grown on TSA plates for four days to stationary growth phase. The cells were harvested from plates and resuspended in Laemmli sample buffer (Boston BioProducts Inc., Worcester, Mass.), boiled for 20 min and electrophoresed on 15% SDS/PAGE gels according to standard procedures (Laemmli, 1970). Gels containing the separated proteins were either stained with Coomassie brilliant blue G (Sigma Chemical Co.) or used for Western blot analysis. Western blotting was performed as previously described (Vemulapalli et al., 1998). Briefly, proteins separated by SDS-PAGE were transferred to a nitrocellulose membrane by using a Trans-blot semidry system (Bio-Rad Laboratories, Hercules, Calif.). For analysis of total proteins, the membranes were incubated with polyclonal serum obtained from a goat hyperimmunized with *B. abortus* strain RB51 (Goat-48) (Roop et al., 1992). After 24 hours of incubation with primary sera, the blots were developed with anti-goat IgG (whole molecule) conjugated with horseradish peroxidase (Sigma Chemical Co).

Growth Rates of *B. melitensis* Strains

Salt-free LB media was prepared by mixing bactotryptone and yeast extract in water per manufacturer's instruction (Difco), but omitting sodium chloride. Single colonies of the wild type, the tspA mutant, and the complemented tspA mutant strains were grown at 37° C. for 72 hours to stationary phase in 5 ml of TSB. The cells were harvested by centrifugation, and resuspended in distilled water. The cell suspensions were used to inoculate 15 ml of LB broth or salt-free LB broth in Klett side-arm flask to 6 to 21 Klett units. Cultures were grown at 37° C. at 200 rpm; Klett readings were recorded every two hours in a Klett-Summerson calorimeter (Klett-Summerson, New York, N.Y.).

Electron Microscopy

The wild type and the tspA mutant strains were grown in 25 ml LB broth to stationary phase. The cells were harvested by centrifugation at 2000×G for 15 min and introduced to 100 ml LB broth. The cultures were incubated overnight at 37° C. with vigorous shaking. The cells were harvested by centrifugation at 2000×G for 15 min, and fixed overnight at 4° C. in formadehyde-paraformaldehyde in cacodylate buffer (Banai et al., 2002). The samples were then processed for thin section electron microscopy as described by Banai et al., (2002). The sections were mounted on copper grids, stained with uranyl acetate and lead citrate, and examined with a JOEL 100 CX-II transmission electron microscope (Zeiss 10 C, Carl Zeiss Inc., New York, N.Y.) at 10,000× magnification.

Persistence of Recombinant *B. melitensis* Strains in Macrophages

TSA plates were inoculated with single colonies of *B. melitensis* strains. After four days of incubation at 37° C. with 5% $CO_2$, the cells were harvested from plates, washed with PBS, resuspended in 20% glycerol, and frozen at −80° C. The number of viable cells was determined after dilutions of the cell suspensions were plated on TS agar. The mouse macrophage-like cell line J774 was seeded at a density of $5\times10^5$/ml in Dulbecco's modified essential medium (DMEM) (Fisher Scientific, Atlanta, Ga.) into 24-well tissue culture dishes and cultured at 37° C. with 5% $CO_2$ until confluent. The tissue culture medium was removed, 200 μl ($2\times10^8$ cells) of the bacterial suspension in PBS was added, and the cells were incubated at 37° C. for four hours. The suspension above the cell monolayer was removed, and the cells were washed three times with PBS. One milliliter of DMEM containing 25 μg of gentamicin was added, and the cells were incubated for 24 hours at 37° C. At 0 and 24 hours of incubation, the growth medium was removed, the cells were washed with PBS, and 500 μl of 0.25% sodium deoxycholate was added to lyse the infected macrophages. After 5 minutes the lysate was diluted in PBS, and the number of viable cells was determined after growth at 37° C. for 72 h on TSA plates. Duplicate samples were taken at all time points, and the assay was repeated two times.

Data Analyses

The student t test was performed in the analysis of colony forming units (cfu) data in the macrophage study (Lyman Ott, 1988).

Results

Analysis of Nucleotide and Protein Sequence of *B. melitensis* tspA

The coding region of the tspA gene is 1329-bp long and is located between 219816 and 221144-bp on chromosome I of *B. melitensis* genome (accession number NC_003317). The nucleotide sequence of the gene (SEQ ID NO: 7) is shown in FIG. 12A. The tspA gene is located immediately upstream of the gene encoding the invasion protein A of this chromosome. Analysis of the putative TspA protein sequence predicted that it contained a 24 amino acid long signal sequence (signal peptide probability: 0.999). The predicted cleavage site of the signal sequence is located between Gly24 and Ala25 residues (maximum cleavage site probability: 0.606). The theoretical mass of the TspA was 47-kDa. However, the predicted N-terminal processing of TspA would result in a mature protein having 419 amino acids and a molecular mass of 44.6-kDa. The amino acid sequence of the full length protein (SEQ ID NO: 8) is shown in FIG. 12B. The predicted subcellular localization of TspA was periplasmic space (Reliability Index: RI=1; Expected Accuracy=63%).

At the amino acid level, tspA gene shared 99% identity with the putative CtpA of *B. suis*. Additionally, it showed up to 77% identity with the putative CtpA proteins and periplasmic proteases of a number of bacterial species including *Agrobacterium tumefaciens, Bartonella quintana, Bradyrhizobium japonicum, Magnetospirillum magnetotacticum, Mesorhizobium loti, Rhodobacter sphaeroides, Rhodopseudomonas palustris*, and *Sinorhizobium meliloti* (data not shown). Part of the report showing the alignment of *B. melitensis* TspA with the closely related CtpA proteins and periplasmic proteases is shown in FIG. 13. Some motifs were conserved in all of the species analyzed, and the number of identical amino acid residues for the species included in FIG. 13 was 174 (data not shown). The amino acid residues that correspond with the amino acids critical for catalysis function of *Synechocystis* sp. strain PCC6803 CtpA protein (Inagaki et al., 2001) are indicated in FIG. 13. These residues were conserved among all the CtpA proteins and periplasmic proteases analyzed.

Inactivation of the tspA Gene in *B. melitensis*

A tspA mutant was generated by allelic exchange. A PCR amplification (see details in Experimental procedures) produced a predicted 1.4-kb size amplicon from the wild type *B. melitensis* strain 16M and an approximately 2.2-kb product from the tspA mutant strain 16MΔtspA, indicating that due to double-crossover event, a 471-bp region was deleted from the tspA gene, and the 1.3-kb $Kan^r$ was inserted at the deletion site of strain 16M genome. The nucleic acid sequence of the deletion mutant (SEQ ID NO: 9) and the corresponding amino acid sequence (SEQ ID NO: 10) are shown in FIGS. 14A and B, respectively. The deleted nucleotide sequence is shown in FIG. 14C (SEQ ID NO: 11). A number of PCR assays using the primers specific for a variety of *B. melitensis* genes confirmed that the tspA mutant was a *brucella* (data not shown).

Comparison of the Protein Profiles of *B. melitensis* Strains

The total protein profiles of the wild type, the tspA mutant, and the complemented tspA mutant strains were investigated by using denaturing gel electrophoresis and western immunoblotting. Two protein bands (approximately 28 and 65-kDa) were shown clearly upregulated in the tspA mutant strain. Those proteins were either absent or very faint in the wild type and the complemented strains.

Growth Rates of Recombinant *B. melitensis* Strains

Figure 15A:
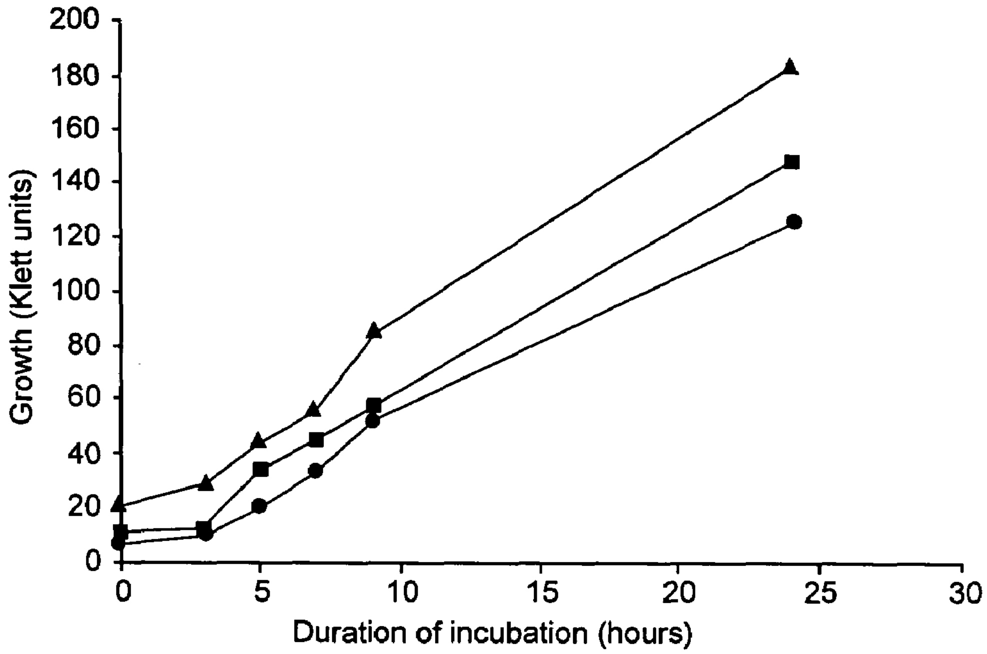
FIGS. 15A and B. Growth of *B. melitensis* strains 16M (●), 16MΔtspA (■), and 16MΔtspA[ctpA$^+$] (▲). All cultures were grown at 37° C. at 200 rpm. Changes in cell density were recorded every two hours in a Klett-Summerson colorimeter. A, Growth of strains in LB media. B, Growth of strains in salt-free LB media.
Figure 15B:
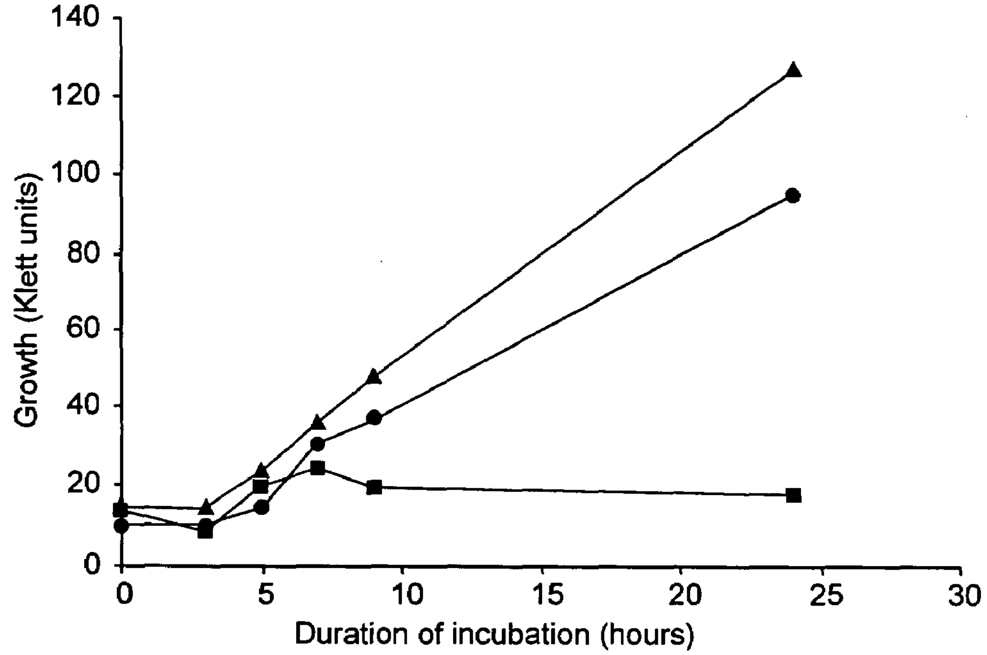

The colonies of the tspA mutant appeared approximately half the size of the colonies of the wild type after three days of growth on TSA plates (data not shown). The wild type and the tspA mutant did not differ in terms of growth rates in LB broth (FIG. 15A). However, in contrast to the wild type, the tspA mutant exhibited a zero growth in salt-free LB broth (FIG. 15B). The colonies of the complemented tspA mutant appeared equal in size to those of the wild type (data not shown). The inability of the mutant strain to grow in salt-free broth was restored when this strain was complemented by introducing the *B. suis* ctpA gene (strain 16MΔtspA[$ctpA^+$]). Additionally, the complemented strain grew at similar rates to the wild type strain in LB or salt-free LB broth (FIGS. 15A and 15B).

Cell Morphology

Figure 16A:
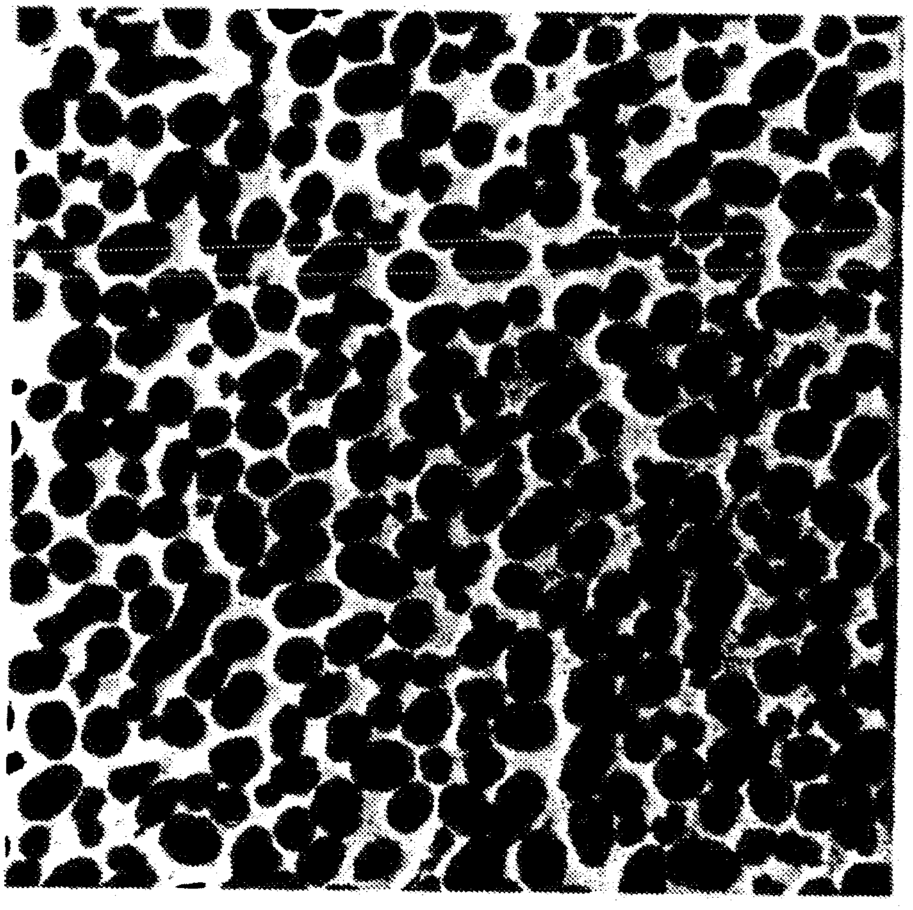
FIGS. 16A and B. The cell morphology of *B. melitensis* strains as observed by electron microscopy. The strain 16M 16 A) displayed native coccobacillus shape of *Brucella*, whereas, those from the strain 16MΔtspA (16 B) acquired a spherical shape with some cell with increased cell diameter. The 1-micron scale bar is inserted in each figure. The magnification is ×10,000.
Figure 16B:
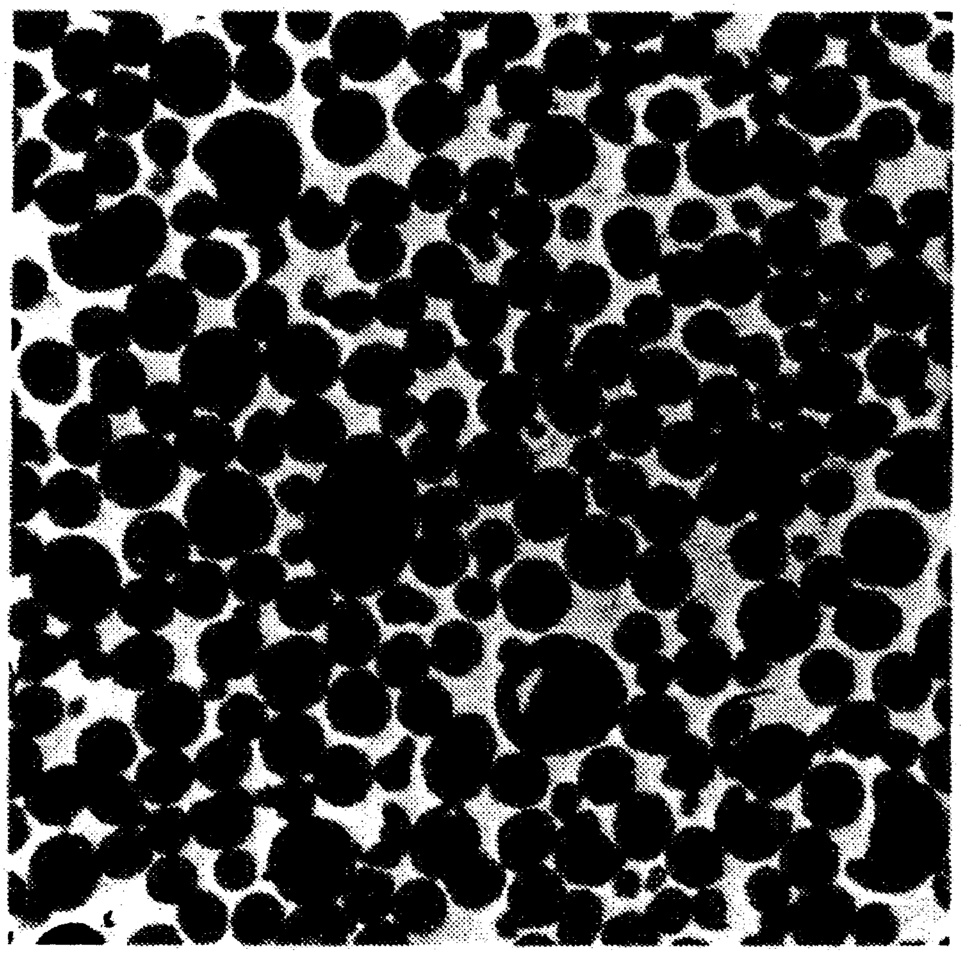

When examined by electron microscopy, the wild type strain grown in LB media displayed the native coccobacillus shape of *Brucella* (FIG. 16A). In contrast, the tspA mutant strain grown in LB media acquired a spherical shape. Additionally, some of the tspA mutant cells displayed a slightly to substantially increased cell diameter (FIG. 16B).

Persistence of *B. melitensis* Strains in J774 Macrophages

The survival of *B. melitensis* strains in J774 mouse macrophage cells was measured (Table 1). Relative to the survival of the wild type strain, that of the tspA mutant declined by 0.2 $log_{10}$ cfu at 0 hours of incubation and 1.2 $log_{10}$ cfu after 24 hours of incubation.

TABLE 1

Viability of *B. melitensis* strains in mouse macrophage J774 cells.

| | Recovery of *brucellae* from macrophages Mean ± SE $log_{10}$ cfu/well)[a] | |
|---|---|---|
| Strain | 0-hours of incubation | 24-hours of incubation |
| 16M | 5.72 ± 0.07 | 4.84 ± 0.09 |
| 16MΔtspA | 5.52 ± 0.04 | 3.65 ± 0.07 |

[a]P values for the difference between mean values were <0.07 for 0-hours of incubation and <0.005 for 24-hours of incubation Discussion Based on its greater homology and substantial alignment with the bacterial carboxyl-terminal proteases and periplasmic proteases, we speculate that the putative TspA of *B. melitensis* is a carboxyl-terminal protease. The predicted signal sequence indicates that TspA is transported across the cytoplasmic membrane and thus suggests that this enzyme functions in the periplasmic space. Other reported bacterial carboxyl-terminal proteases like Tsp of *E. coli* (Hara et al., 1991) and CtpA of *Borrelia burgdorferi* (Ostberg et al., 2004) are also believed to function in the periplasmic space. The *B. melitensis* TspA amino acid sequence shared 99% homology with the *B. suis* CtpA sequence. The published protein sequence of *B. suis* CtpA (GenBank accession number NP_698817) does not include a signal sequence. This is because when the *B. suis* genomic sequence was annotated (Paulson et al., 2002), an 18 amino acid region had been mistakenly excluded from the N-terminal end of the actual CtpA amino acid sequence.

Thus far, the CtpA proteases have been well characterized only for the cyanobacterium *Synechocystis* sp. strain PCC 6803 (Anbudurai et al., 1994; Shestakov et al., 1994), the green alga *S. obliquus* (Trost et al., 1997), higher plants (Takahashi et al., 1988), and *E. coli* (Hara et al., 1989; 1991). A recent report by Ostberg et al., (2004) has partially characterized the substrates and the pleiotropic effects of CtpA protein of *B. burgdorfei* CtpA protein. In *Synechocystis* CtpA, among the conserved amino acids, Asp-253, Arg-255, Ser-313, Glu-316 and Lys-338 are critical for the in vivo activity (Inagaki et al., 2001). The *B. burgdorferi* CtpA protein and the *E. coli* TspA protein also carry the Asp, Arg, Ser, Glu and Lys residues corresponding to those residues of *Synechocystis*. Our sequence alignment work disclosed that the *B. melitensis* TspA sequence carries residues Asp238, Arg240, Ser300, Glu303, and Lys325 that correspond with those amino acid residues of CtpA sequences of *Synechocystis, B. burgdorferi*, and *E. coli*. Liao et al., (2000) reported that in CtpA protein of eukaryotic alga *S. obliquus*, the amino acid residues Ser372 and Lys397 form the catalytic center of this enzyme. These two amino acids are located 25 amino acids apart from each other in the CtpA proteins of *Synechocystis* species, *S. obliquus, B. burgdorferi* and *E. coli*. Consistent with these observations, in the *B. melitensis* TspA protein sequence, the Ser300 and Lys325 amino acids are located exactly 25 amino acids apart from each other. Accordingly, it could be postulated that these two amino acids make the Ser/Lys catalytic dyad of *B. melitensis* TspA.

By comparing the total protein expression profiles of the wild type and the tspA mutant *B. melitensis* strains, we found that expression of a number of proteins was altered by tspA inactivation. In fact the expression of at least two protein products (one of approximately 65-kDa and another of 28-kDa) was seen up-regulated due to mutation in the tspA gene. With the used immunoblotting procedure, it was impossible to detect if the expression of any other proteins was affected due to mutation. Further work using two-dimensional gel electrophoresis is required to identify all the proteins that are affected by the tspA mutation. Ostberg et al., (2004) reported that the expression of the pore forming protein Oms28 was up-regulated when the ctpA gene encoding the CtpA protein was mutated in *B. burgdorferi*. These workers postulated the up-regulation of Oms28 protein as a result of a lack of C-terminal processing needed for regulating an inhibitor or an activator involved in modulation of Oms28 expression. Genetic complementation by introduction of a shuttle vector with the cloned ctpA gene showed restored protein expression in *B. melitensis* mutant to the normal pattern (FIG. 3). Further experimentation will be required to determine whether this is a transcriptional or a posttranslational effect.

Western immunoblotting was not sensitive enough to identify the substrates of *B. melitensis* TspA protein. The protein D1 has been identified as the substrate of CtpA of cyanobacteria (Nixon et al., 1992), green algae (Liao et al., 2000) and higher plants (Takahashi et al., 1988). The PBP-3 and aberrant proteins are the substrates of *E. coli* Tsp (Hara et al., 1991, Keiler et al., 1996). The protein P13 and the hypothetical protein BB0323 have been identified as the potential targets of *B. burgdorferi* CtpA (Ostberg et al., 2004). The substrates of CtpA proteins of *Brucella* or any other bacteria have yet to be identified.

Just like the tsp mutant *E. coli* (Hara et al., 1991) and the ctpA mutant *B. suis* (Bandara et al., 2005, in press), the tspA mutant *B. melitensis* strain exhibited a zero growth in salt-free media suggesting that TspA function is involved either directly or indirectly in protection from osmotic stresses. Electron microscopy data revealed that similar to the ctpA mutant *B. suis*, the tspA mutant *B. melitensis* strain possessed a spherical cell shape with some cells having increased cell diameter. Previous reports have shown that the *E. coli* strains deficient in penicillin-binding protein-2 (PBP-2) synthesis lacked the cell elongation pathway and grew as spherical cells because only septal synthesis was active in these strains (de Pedro et al., 2001). Similarly, a PBP-2 deficient strain of *Erwinia amylovora* displayed a large spherical phenotype, whereas its parent type counterpart displayed a rod-shaped phenotype (Milner et al., 1993). The diameter of the peptidoglycan stalk of *Caulobacter crescentus* increases when its PBP-2 homolog is inactivated (Seitz and Brun, 1998). These reports suggest that PBP-2 enzyme helps to regulate cellular diameter at the time of division. Based on these observations it can be hypothesized that the TspA protein is involved in processing of PBP-2 enzyme in *B. melitensis*, and disruption of tspA resulted in spherical shape cell with increased cell diameter.

In *Bartonella bacilliformis* genome, the gene encoding the CtpA is located immediately upstream of the gene encoding invasion associated locus A (ialA) (Mitchell and Minnick, 1997). Interestingly, in the *B. melitensis* genome, the tspA gene is located right upstream from the gene encoding the invasion protein A (locus tag BMEI0215, GeneID 1195927). Genetic complementation by introduction of a shuttle vector with the cloned tspA gene showed that the growth patterns were similar for the complemented tspA mutant and the wild type strain (FIG. 4B), and the total protein profiles were the same for the complemented strain and the wild type strain (FIG. 3). These complementation experiments confirmed that the phenotype observed after inactivation tspA gene was due to lack of expression of TspA alone and not due to a polar effect.

When introduced into macrophages, after 24 hours of incubation, the persistence of the tspA mutant strain declined significantly compared to that of the wild type strain indicating that TspA is important for survival, in particular against early killing by macrophages. Apparently, due to the change of protein expression, and due to a possible influence on protein processing, the tspA mutant cells were unable to avoid phagosome-lysosome fusion, and thereby subjected to early killing.

In summary, the tspA gene of *B. melitensis* is homologous to the genes encoding carboxyl-terminal proteases and periplasmic proteases of other bacteria. Like the ctpA gene of *B. bacilliformis*, the tspA of *B. melitensis* is located immediately upstream of the gene encoding an invasion protein. Similar to the CtpA proteins of cyanobacteria, green algae, higher plants, *E. coli*, and *B. burgdorferi*, the TspA of *B. melitensis* contains all five amino acids critical for the CtpA catalytic activity, and a potential Ser/Lys catalytic dyad. Similar to the CtpA of *B. burgdorferi*, the TspA of *B. melitensis* influences the protein expression profile. Similar to the Tsp of *E. coli* and CtpA of *B. suis*, the TspA influences salt-sensitive growth and cell morphology of *B. melitensis*. In addition, similar to the CtpA of *B. suis*, the TspA of *B. melitensis* influences the intracellular persistence of the bacterium.

REFERENCES FOR EXAMPLE 3

Acha, P., and Szyfres, B. (1980) Zoonoses and communicable diseases common to man and animals, p. 28-45. In Pan American Health Organization, Washington, D.C.

Anbudurai P. R., Mor, T. S., Ohad, I., Shestakov, S, V, and Pakrasi, H. B. (1994) The ctpA gene encodes the C-terminal processing protease for the D1 protein of the photosystem II reaction center complex. *Proc Natl Acad Sci U S A* 91:8082-8086.

Banai, M., Adams, L. G., Frey, M., Pugh, R., and Ficht, T. A. (2002) The myth of *Brucella* L-forms and possible involvement of *Brucella* penicillin binding proteins in pathogenicity. *Vet Microbiol* 90:263-279.

Bandara, A. B., Sriranganathan, N., Schurig, G. G. and Boyle, S. M. (2005) Putative Carboxyl-Terminal Protease Regulates *Brucella suis* Morphology in Culture and Persistence in Macrophages and Mice. *J Bacteriol* 187 (16) (In Press).

Baumler A. J., Kusters J. G., Stojiljkovic I., and Heffron F. (1994) *Salmonella typhimurium* loci involved in survival within macrophages. *Infect Immun* 62:1623-1630.

Bendtsen, J. D., Nielsen, H., von Heijne, G. and Brunak, S. (2004) Improved prediction of signal peptides: SignalP 3.0. *J Mol Biol* 340:783-795, Corbel, M. J., and Brinley Morgan, W. J. (1984) Genus *Brucella* Meyer and Shaw 1920, 173 AL. p. 377-390. In N. R. Krieg and J. G. Holt (ed.), Bergey's Manual of Systematic Bacteriology, vol. 1. Williams and Wilkins, Baltimore.

Dalbey, R. E., and Von Heijne, G. (1992) Signal peptidases in prokaryotes and eukaryotes—a new protease family. *Trends Biochem Sci* 17:474-478.

de Pedro, M. A., Donachie, W. D., Holtje, J. V., and Schwarz, H. (2001) Constitutive septal murein synthesis in *Escherichia coli* with impaired activity of the morphogenetic proteins RodA and penicillin-binding protein 2. *J Bacteriol* 183:4115-4126.

Hara H., Nishimura, Y., Kato, J., Suzuki, H., Nagasawa, H., Suzuki, A., and Hirota, Y. (1989) Genetic analyses of processing involving C-terminal cleavage in penicillin-binding protein 3 of *Escherichia coli. J Bacteriol* 171:5882-5889.

Hara, H., Yamamoto, Y., Higashitani, A., Suzuki, H., and Nishimura, Y. (1991) Cloning, mapping, and characterization of the *Escherichia coli* prc gene, which is involved in C-terminal processing of penicillin-binding protein 3. *J Bacteriol* 173:4799-4813.

Inagaki, N., Maitra, R., Satoh, K., Pakrasi, H. B. (2001) Amino acid residues that are critical for in vivo catalytic activity of CtpA, the carboxyl-terminal processing protease for the D1 protein of photosystem II. *J Biol Chem* 276:30099-30105.

Inagaki, N., Yamamoto, Y., Mori, H., and Satoh, K. (1996) Carboxyl-terminal processing protease for the D1 precursor protein: cloning and sequencing of the spinach cDNA. *Plant Mol Biol* 30:39-50.

Keiler, K. C., Waller, P. R. H., and Sauer, R. T. (1996) Role of a peptide tagging system in degradation of proteins synthesized from damaged messenger RNA. *Science* 271: 990-993.

Kovach, M. E., Phillips, R. W., Elzer, P. H., Roop II R. M., and Peterson, K. M. (1994) pBBR1 MCS: a broad-host range cloning vector. *Bio Techniques* 16:800-802.

Laemmli, U. K. (1970) Cleavage of structural proteins during the assembly of the head of bacteriophage T4. *Nature* 227:680-685.

Liao, D.-I., Qian, J., Chisholm, D. A., Jordan, D. B., and Diner, B. A. (2000) *Nat Struct Biol* 7:749-753.

Lyman Ott, R. (1988) An Introduction to Statistical Methods and Data Analysis. Fourth Edition. Duxbury Press. Belmont, Calif.

McQuiston, J. R., Schurig, G. G., Sriranganathan, N., and Boyle S. M. (1995) Transformation of *Brucella* species with suicide and broad host-range plasmids. *Methods Mol Bio* 47:143-148. Milner, J. S., Dymock, D., Cooper, R. M., and Roberts, I. S. (1993) Penicillin-binding proteins from *Erwinia amylovora*: mutants lacking PBP2 are avirulent. *J Bacteriol* 175:6082-6088. Mitchell S. J., and Minnick, M. F. (1997) A carboxy-terminal processing protease gene is located immediately upstream of the invasion-associated locus from *Bartonella bacilliformis. Microbiology* 143:1221-33.

Nixon P. J., Trost J. T., and Diner B. A. (1992) Role of the carboxy terminus of polypeptide D1 in the assembly of a functional wateroxidizing manganese cluster in photosystem II of the cyanobacterium *Synechocystis* sp. PCC 6803: assembly requires a free carboxyl group at C-terminal position 344. *Biochemistry* 31:1085910871.

Oelmüller, R., Herrmann, R. G. and Pakrasi, H. B. (1996) Molecular studies of CtpA, the carboxyl-terminal processing protease for the D1 protein of the photosystem II reaction center in higher plants. *J Biol Chem* 271:21848-21856.

Ostberg, Y., Carroll, J. A., Pinne, M., Krum, J. G., Rosa, P., and Bergstrom, S. (2004) Pleitropic effects of inactivating a carboxyl-terminal protease CtpA, in *Borrelia burgdorferi. J Bacteriol* 186:2074-2084.

Paetzel, M. and Dalbey, R. E. (1997) Catalytic hydroxyl/amine dyads within serine proteases. *Trends Biochem Sci* 22:28-31. Paulson, I. T., Sheshadri R., Nelson K. E. et al., (2002) The *Brucella suis* genome reveals fundamental similarities between animal and plant pathigens and symbionts. *Proc Natl Acad Sci USA* 99:13148-13153.

Popham, D. L., and Young, K. D. (2003) Role of penicillin-binding proteins in bacterial cell morphogenesis. *Current Opinion in Microbiology* 6:594-599.

Roop, R. M. 2 nd, Price, M. L., Dunn, B. E., Boyle, S. M, Sriranganathan, N., and Schurig, G. G. (1992) Molecular cloning and nucleotide sequence analysis of the gene encoding the immunoreactive *Brucella abortus* Hsp60 protein, BA60 K. *Microb Pathog* 12:47-62.

Schurig, G. G., Roop, R. M., Bagchi, T., Boyle, S. M., Buhrman, D., and Sriranganathan, N. (1991) Biological properties of RB51: a stable rough strain of *Brucella abortus. Vet Microbiol* 28:171-188.

Seitz, L. C., and Brun, Y. V. (1998) Genetic analysis of mecillinam-resistant mutants of *Caulobacter crescentus* deficient in stalk biosynthesis. *J Bacteriol* 180:5235-5239.

Shestakov, S. V., Anbudurai, P. R., Stanbekovas, G. E., Gadzhiev, A., Lind L. K., and Pakrasi, H. B. (1994) Molecular cloning and characterization of the ctpA gene encoding a carboxyl-terminal processing protease. Analysis of a spontaneous photosystem II-deficient mutant strain of the cyanobacterium *Synechocystis* sp. PCC 6803. *J Biol Chem* 269:19354-19359.

Silber, K. R., Keiler, K. C., and Sauer, R. T. (1992) Tsp: a tail-specific protease that selectively degrades proteins with nonpolar C termini. *Proc Natl Acad Sci U.S.A* 89:295-299.

Takahashi, M., Shiraishi, T., and Asada, K. (1988) COOH-terminal residues of D1 and the 44 kDa CPa-2 at spinach photosystem II core complex. *FEBS Lett* 240:6-8.

Trost, J. T., Chisholm, D. A., Jordan, D. B., and Diner, B. A. (1997) The D1 C-terminal processing protease of photosystem II from *Scenedesmus obliquus*. Protein purification and gene characterization in wild type and processing mutants. *J Biol Chem* 272:20348-20356.

Vemulapalli, R., Duncan, A. J., Boyle, S. M., Sriranganathan, N., Toth, T. E., and Schurig, G. G. (1998) Cloning and sequencing of yajC and secD homologs of *Brucella abortus* and demonstration of immune responses to YajC in mice vaccinated with *B. abortus* RB51. *Infect Immun* 66:5684-5691.

Yamamoto, Y., Inagaki, N., and Satoh, K. (2001) Overexpression and characterization of carboxyl-terminal processing protease for precursor D1 protein: regulation of enzyme-substrate interaction by molecular environments. *J Biol Chem* 276:7518-7525

Young, E. J. (1983) Human brucellosis. *Rev Infect Dis* 5:821-842.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

---

We claim:

1. An attenuated, recombinant *Brucella melitensis* strain deficient in the carboxyl-terminal proteolytic processing activity of a tail-specific protease wherein said deficiency is caused by a nucleotide sequence deletion within a tspA gene that, absent said nucleotide sequence deletion, encodes the amino acid sequence of the TspA protease set forth in SEQ ID NO:8.

2. The attenuated, recombinant *Brucella melitensis* strain of claim 1, wherein said attenuated recombinant *Brucella melitensis* strain is 16MΔtspA.

3. A method for eliciting an immune response to *Brucella melitensis* in a mammal, or treating Brucellosis in a mammal comprising administering to said mammal an attenuated, recombinant, *Brucella melitensis* strain deficient in the carboxyl-terminal proteolytic processinq activity of a tail-specific protease wherein said deficiency is caused by a nucleotide sequence deletion within a tspA gene that, absent said nucleotide sequence deletion, encodes the amino acid sequence of the TspA protease set forth in SEQ ID NO:8, wherein said attenuated, recombinant, *Brucella melitensis* strain is administered in a quantity sufficient to elicit an immune response, thereby eliciting an immune response.

4. The method of claim 3, wherein said attenuated, recombinant *Brucella melitensis* strain is 16MΔtspA.

5. The method of claim 3, wherein said mammal is selected from the group consisting of humans, sheep, goats, dogs, swine, cattle, and reindeer.

6. A composition for eliciting an immune response to *Brucella melitensis* in a mammal, comprising (i) an attenuated, recombinant, *Brucella melitensis* strain with a deficiency in the carboxypeptidase activity of a tail-specific protease, wherein said deficiency is caused by a nucleotide sequence deletion in a tspA gene that, absent said nucleotide sequence deletion, encodes the TspA carboxypeptidase having the amino acid sequence set forth in SEQ ID NO:8; and (ii) a physiologically suitable carrier.

7. The composition of claim 6, wherein said attenuated, recombinant *Brucella melitensis* strain is 16MΔtspA.

* * * * *